United States Patent
Xiao et al.

(10) Patent No.: US 12,297,446 B2
(45) Date of Patent: May 13, 2025

(54) RECOMBINANT PARVOVIRAL VECTORS AND METHOD OF MAKING AND USE THEREOF

(71) Applicant: NIKEGEN LIMITED, Sai Ying Pun (HK)

(72) Inventors: Weidong Xiao, Dresher, PA (US); Xiangping Yu, Fujian (CN)

(73) Assignee: NIKEGEN LIMITED, Sai Ying Pun (HK)

( * ) Notice: Subject to any disclaimer, the term of this patent is extended or adjusted under 35 U.S.C. 154(b) by 1008 days.

(21) Appl. No.: 17/309,154

(22) PCT Filed: Nov. 1, 2019

(86) PCT No.: PCT/US2019/059396
§ 371 (c)(1),
(2) Date: Apr. 30, 2021

(87) PCT Pub. No.: WO2020/092904
PCT Pub. Date: May 7, 2020

(65) Prior Publication Data
US 2022/0186250 A1    Jun. 16, 2022

Related U.S. Application Data

(60) Provisional application No. 62/755,144, filed on Nov. 2, 2018.

(51) Int. Cl.
*C12N 15/86* (2006.01)

(52) U.S. Cl.
CPC .... *C12N 15/86* (2013.01); *C12N 2750/14143* (2013.01); *C12N 2750/14151* (2013.01)

(58) Field of Classification Search
CPC .......... C12N 15/86; C12N 2750/14011; C12N 2750/14111
See application file for complete search history.

(56) References Cited

U.S. PATENT DOCUMENTS

| | | |
|---|---|---|
| 2002/0058341 A1 | 5/2002 | Nakai et al. |
| 2007/0166286 A1 | 7/2007 | Seed et al. |
| 2013/0252325 A1 | 9/2013 | Samulski et al. |
| 2015/0329902 A1 | 11/2015 | Hill |
| 2016/0102297 A1 | 4/2016 | Hewitt et al. |
| 2018/0298380 A1 | 10/2018 | Gao et al. |

FOREIGN PATENT DOCUMENTS

WO   2019/118806 A1   6/2019

OTHER PUBLICATIONS

Xie et al. Short DNA hairpins compromise recombinant adeno-associated virus genome homogeneity. Molecular Therapy 2017, 25;6:1363-1374. (Year: 2017).*
International Search Report and Written Opinion of PCT/US2019/059396, mailed Feb. 11, 2020.

* cited by examiner

*Primary Examiner* — Christopher M Babic
*Assistant Examiner* — Jennifer S Spence
(74) *Attorney, Agent, or Firm* — Michael Ye; Kalos Athena Wang PLLC

(57) ABSTRACT

A parvovirus vectors with a viral genome having a covalently closed end (ccePV vectors), methods for producing such vectors and DNA constructs used for producing such vectors.

11 Claims, 28 Drawing Sheets
Specification includes a Sequence Listing.

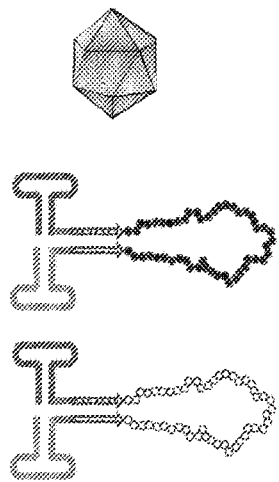
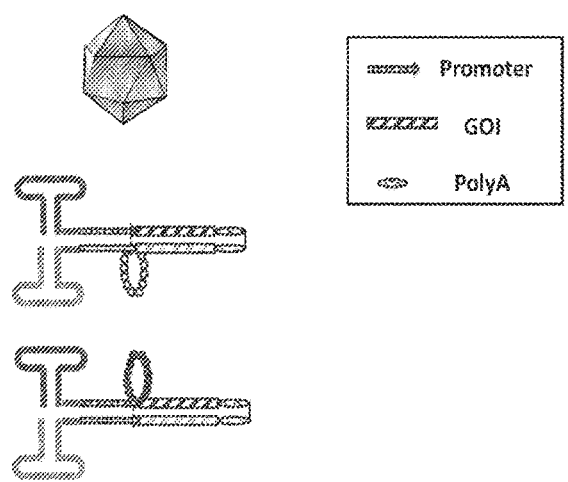
FIG. 3

FG. 17

SEQUENCE LISTING

```
<160> NUMBER OF SEQ ID NOS: 6

<210> SEQ ID NO 1
<211> LENGTH: 56
<212> TYPE: DNA
<213> ORGANISM: Artificial Sequence
<220> FEATURE:
<223> OTHER INFORMATION: Synthetic

<400> SEQUENCE: 1
tatcagcaca caattgccca ttatacgcgc gtataatgga ctattgtgtg ctgata          56

<210> SEQ ID NO 2
<211> LENGTH: 56
<212> TYPE: DNA
<213> ORGANISM: Artificial Sequence
<220> FEATURE:
<223> OTHER INFORMATION: Synthetic
```

-continued

```
<400> SEQUENCE: 2
tatcagcaca caatagtcca ttatacgcgc gtataatggg caattgtgtg ctgata          56

<210> SEQ ID NO 3
<211> LENGTH: 28
<212> TYPE: DNA
<213> ORGANISM: Artificial Sequence
<220> FEATURE:
<223> OTHER INFORMATION: Synthetic

<400> SEQUENCE: 3
gcgtataatg gactattgtg tgctgata                                         28

<210> SEQ ID NO 4
<211> LENGTH: 28
<212> TYPE: DNA
<213> ORGANISM: Artificial Sequence
<220> FEATURE:
<223> OTHER INFORMATION: Synthetic

<400> SEQUENCE: 4
tatcagcaca caattgccca ttatacgc                                         28

<210> SEQ ID NO 5
<211> LENGTH: 28
<212> TYPE: DNA
<213> ORGANISM: Artificial Sequence
<220> FEATURE:
<223> OTHER INFORMATION: Synthetic

<400> SEQUENCE: 5
gcgtataatg ggcaattgtg tgctgata                                         28

<210> SEQ ID NO 6
<211> LENGTH: 28
<212> TYPE: DNA
<213> ORGANISM: Artificial Sequence
<220> FEATURE:
<223> OTHER INFORMATION: Synthetic

<400> SEQUENCE: 6
tatcagcaca caatagtcca ttatacgc                                         28
```

RECOMBINANT PARVOVIRAL VECTORS AND METHOD OF MAKING AND USE THEREOF

RELATED APPLICATION

This application claims the priority of U.S. Provisional Application No. 62/755,144, filed on Nov. 2, 2018, which is incorporated herein by reference in its entirety.

FIELD

The present application generally relates to recombinant viral vectors and, in particular, to parvovirus vectors with a viral genome having a double-stranded region with a covalently closed end.

SUMMARY

The present application describes parvovirus vectors with a viral genome having a covalently closed end (ccePV vectors), methods for producing such vectors and DNA constructs used for producing such vectors. The vectors and methods are applicable to all gene transfer/therapy applications, such as those requiring delivery of recombinant gene expression cassettes. The ccePV vectors are highly flexible, user-friendly, and can be easily modified (via routine DNA cloning) and utilized (via standard PV vector or AAV vector technology) for various applications.

BRIEF DESCRIPTION OF THE DRAWINGS

FIG. 3, panel (A) shows an embodiment of a cceAAV containing a long non-complimentary region of single stranded (ss) DNA. Panel (B) shows another embodiment of a cceAAV containing a single stranded loop region (or bulged region) within a complementary double stranded region. The non-complementary ssDNA can include any DNA sequence, such as an aptamer/deoxyribozymes encoded sequence, a polypeptide encoded sequence, a siRNA encoded sequence, an miRNA encoded sequence, an shRNA encoding sequence, a polyadenylation signal, an insulator sequence etc. An aptamer may be stabilized through its linkage/attachment to the flanking complementary DNA sequences adjacent thereto. The ssDNA in cceAAV-LS is an efficient template for gene editing or DNA repair applications.

FIG. 6 depicts a producer cell with a stably integrated with Cas9/gRNA nuclease. In turn, the plasmid is linearized and then ligated to itself by a host cell ligase to form a template for AAV production comprising an expression cassette sequences flanked by AAV ITRs on each side as shown. Thus, the DNA fragment is modified by in vivo digestion and ligation steps occurring in the host cell environment. In some embodiments, nucleotide insertions or deletions may be engineered into the ligation site. The closed ends of cceAAV-ZL may have the same sequences or may have minor variations.

in vitro, transfected with Rep, Cap and pAd in AAV producing cells, and ligated in vivo; or (3) directly transfected in with Rep, Cap and pAd in AAV producing cells, where the starting plasmid is digested in vivo and ligated in vivo. The illustration here is for AAV produced in 293 cells using an adenovirus helper. Other packaging systems include herpes virus, vaccinia virus or baculovirus-based packaging systems that are compatible with the proposed digestion/ligation methods. The vector plasmids can also be in the host cells in stable episomal form before the digestion. This approach represents a more efficient system for scAAV production, since it employs a wild type ITR arrangement which is directly compatible for replication and packaging into parvovirus particles. In contrast, the conventional method for producing scAAVs relies on an indirect scheme of generating the template molecule from a double stranded plasmid vector or shDNA. The indirect conversion via mTR or shDNA presents a rate-limiting step in scAAV vector production. This approach can be further extended to other parvoviruses in accordance with the methods and compositions described herein.

Figure 24:
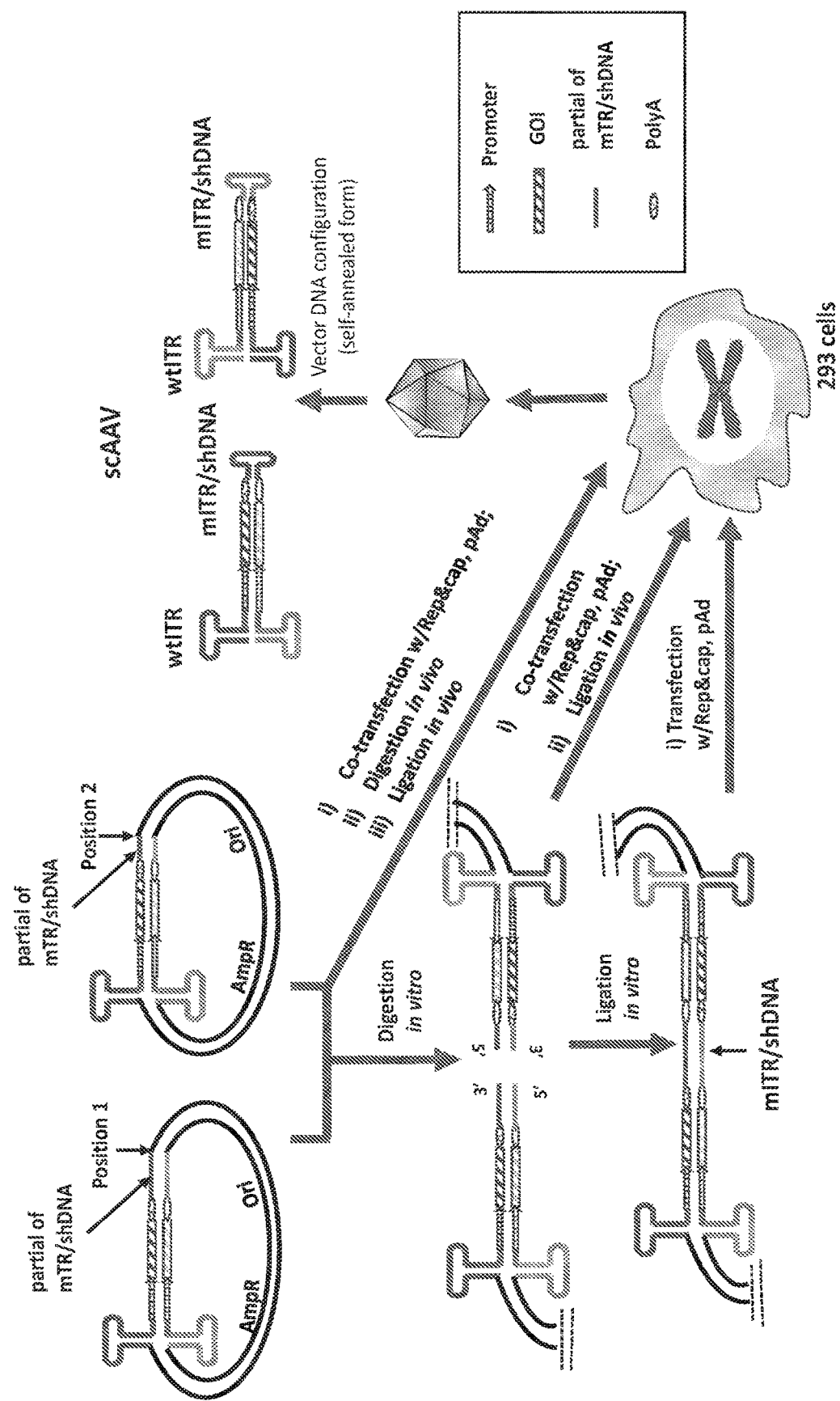

FIG. 24 illustrates an exemplary ligation strategy to produce a scAAV in the form of a mTR or shDNA closed end vector. Two starting plasmids are used, each containing an AAV ITR, whereby each plasmid is digested and ligated to form structures having a mTR or shDNA as shown. Here, the fragments are designed to avoid self-ligation, wherein the resulting fragments can be subject to three different pathways for producing the corresponding scAAV particles. The starting plasmid can be: (1) digested (i.e., linearized) in vitro, ligated in vitro and then transfected in AAV producing cells (e.g., 293, or any other cells with complementary genes supplied) transfected with Rep, Cap and pAd (with additional adenovirus helper genes not supplied in the producing cell line; (2) digested (i.e., linearized) in vitro, transfected with Rep, Cap and pAd in AAV producing cells, and ligated in vivo; or (3) directly transfected in with Rep, Cap and pAd in AAV producing cells, where the starting plasmid is digested in vivo and ligated in vivo. The illustration here is for AAV produced in 293 cells using an adenovirus helper. Other packaging systems include herpes virus, vaccinia virus or baculovirus-based packaging systems that are compatible with the proposed digestion/ligation methods. The vector plasmids can also be in the host cells in stable episomal form before the digestion. As noted above, this approach represents a more efficient system for scAAV production.

Figure 25:
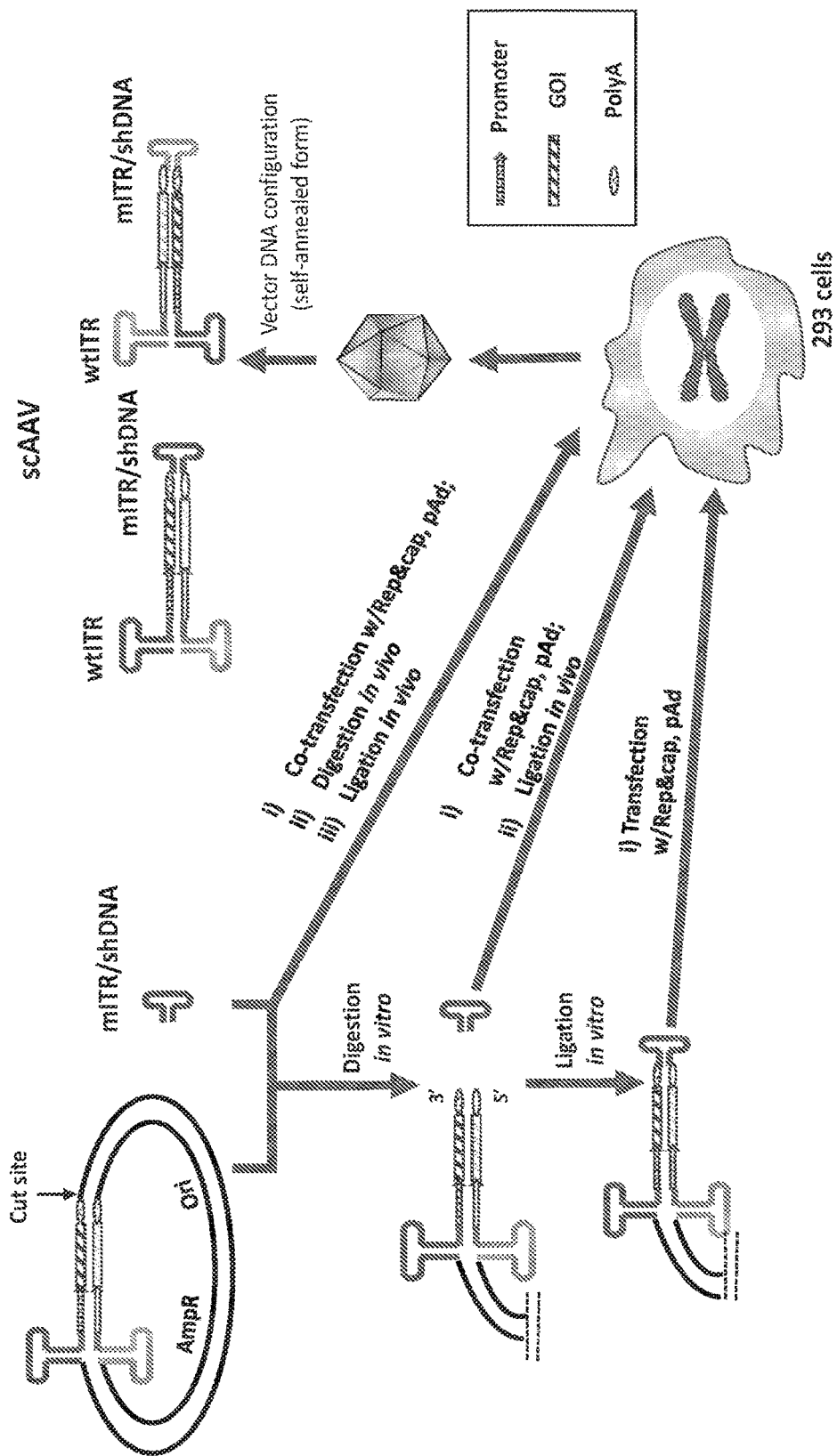

FIG. 25 illustrates an exemplary ligation strategy to produce a scAAV in the form of a mTR or shDNA closed end vector. This approach utilizes a single starting plasmid with an AAV ITR, which is digested and ligated to a synthesized adapter to form the depicted structures containing a mTR or shDNA. The fragments are designed in a way to avoid self-ligation. The synthesized adapter can include a partial or full mTR or shDNA. The resulting fragments can be subject to three different pathways for producing the corresponding scAAV particles. The starting plasmid can be: (1) digested (i.e., linearized) in vitro, ligated in vitro and then transfected in AAV producing cells (e.g., 293, or any other cells with complementary genes supplied) transfected with Rep, Cap and pAd (with additional adenovirus helper genes not supplied in the producing cell line; (2) digested (i.e., linearized) in vitro, transfected with Rep, Cap and pAd in AAV producing cells, and ligated in vivo; or (3) directly transfected in with Rep, Cap and pAd in AAV producing cells, where the starting plasmid is digested in vivo and ligated in vivo. The illustration here is for AAV produced in 293 cells using an adenovirus helper. Other packaging systems include herpes virus, vaccinia virus or baculovirus-based packaging systems that are compatible with the proposed digestion/ligation methods. The vector plasmids can also be in the host cells in stable episomal form before the digestion. As noted above, this approach represents a more efficient system for scAAV production.

Figure 26:
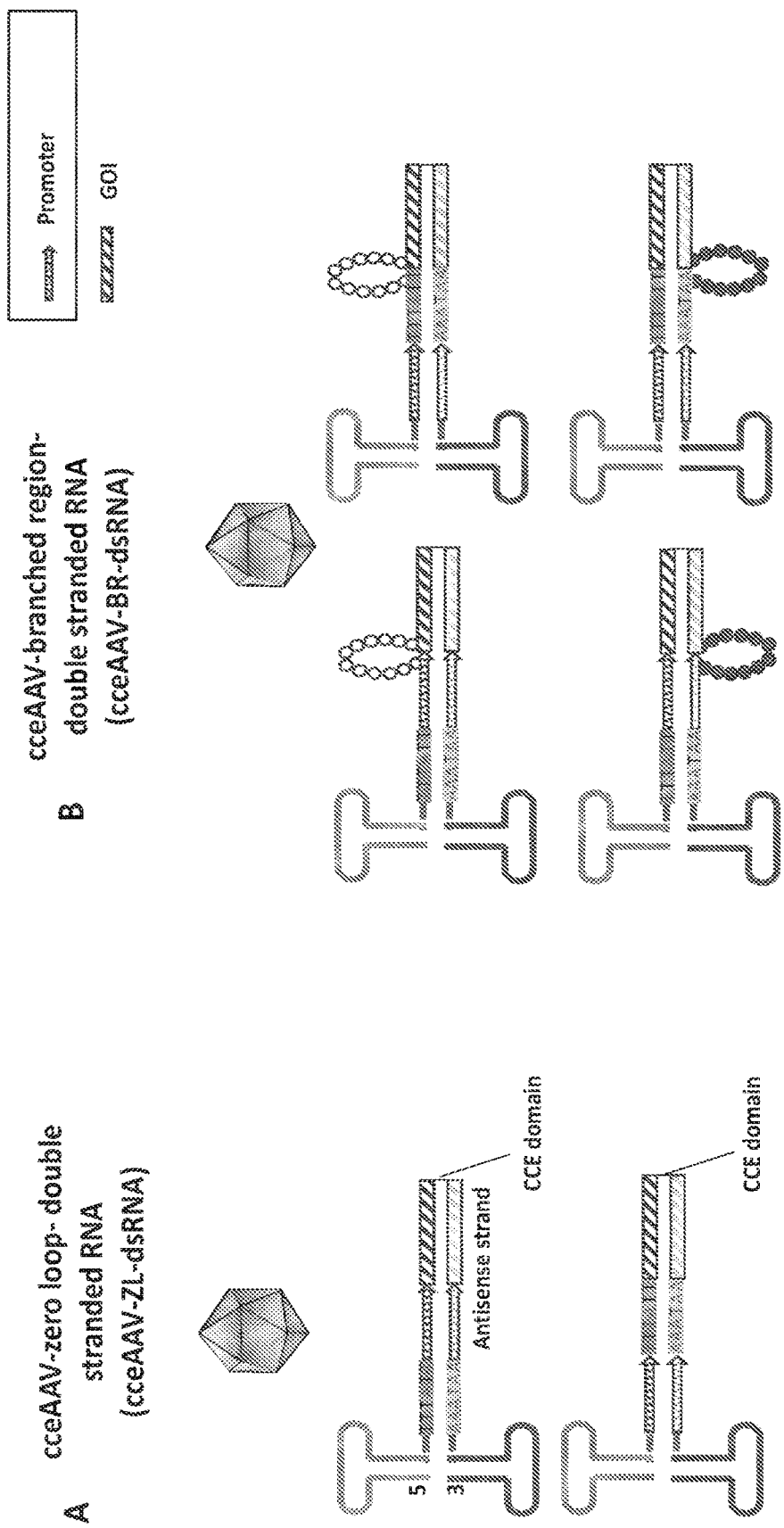

FIG. 26 illustrates exemplary cceAAVs that express double-stranded AAV RNAs with no-loop (panel A, cceAAV-ZL-dsRNA) or double-stranded AAV RNAs with branched region (panel B, cceAAV-ZL-dsRNA). The major difference is the location of transcription terminator position is in the reverse orientation when the vector is illustrated in the self-complementary configuration. The transcription terminator sites (here uses poly A as an example) are before the dsRNA region in the reverse orientation. When vectors are converted to duplex format, the overall configuration is in this order: ITR, poly A (reverse), promoter, dsRNA coding region, promoter (reverse), poly A and ITR. In some particular case, poly A or transcription terminator site can be embedded into the promoter region in the reverse orientation. If an intron is used, such as transcription terminator site may also be embedded into the intron. Poly A or transcription terminator site needs to be at any place after the complementary strand for dsRNA coding region. Panel B illustrates different configurations of dsRNA coding regions. Similar vector can be made for parvovirus vectors.

Figure 27:
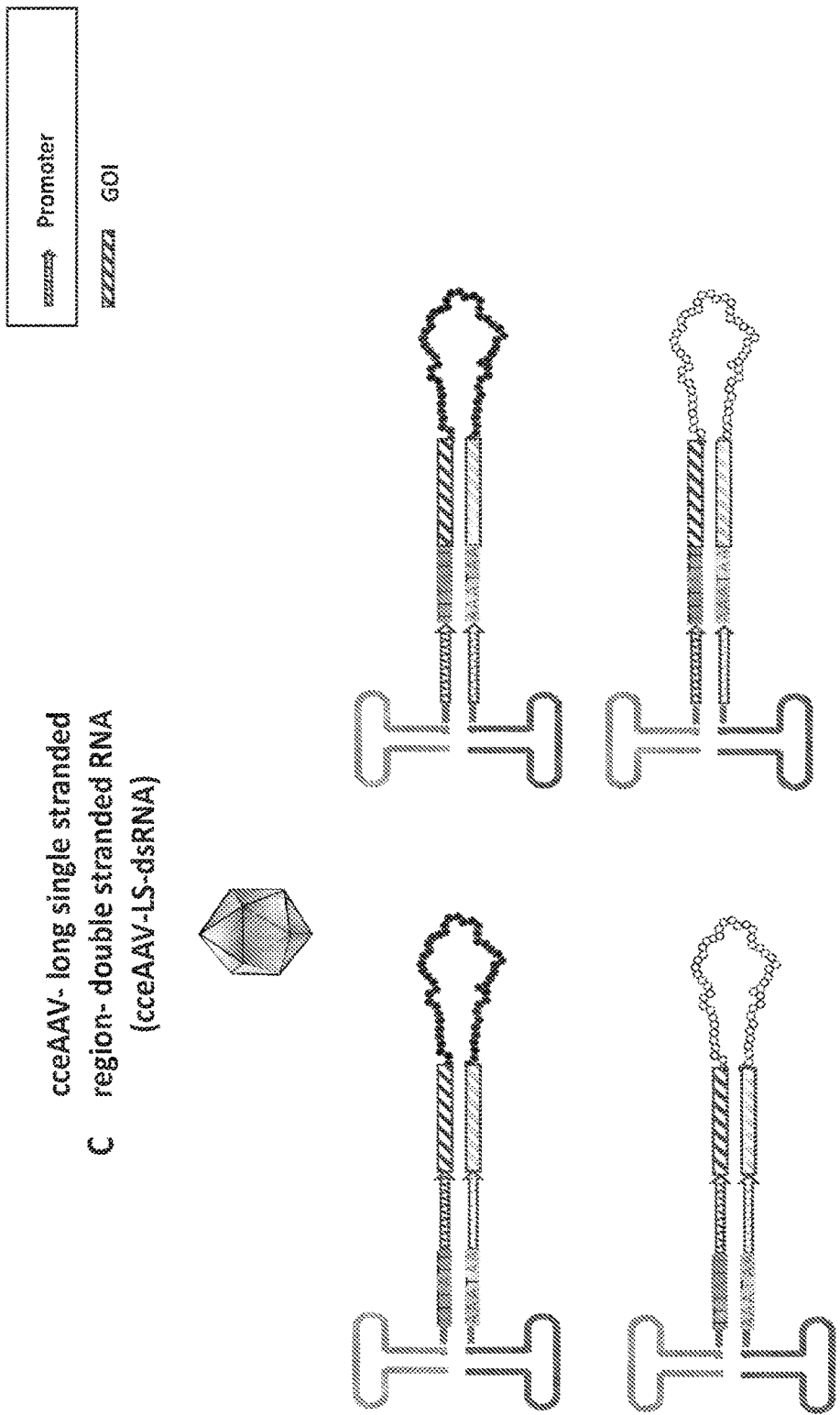

FIG. 27 illustrates exemplary cceAAVs that express double-stranded AAV RNAs with long single-stranded region (panel C).

Figure 28:
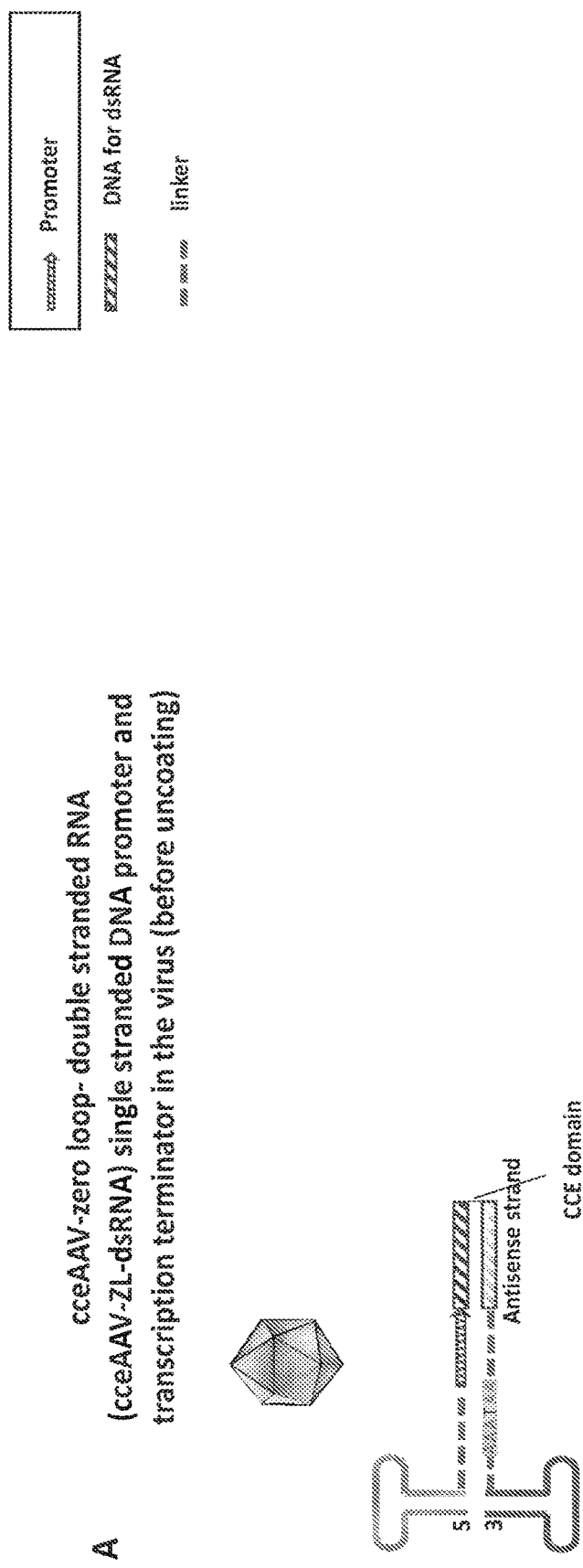

FIG. 28 illustrates exemplary cceAAVs that express double-stranded AAV RNAs with no-loop (panel A, cceAAV-ZL-dsRNA) which contains only one DNA promoter and only one transcription terminator. The capacity for dsRNA coding sequence is enhanced. This vector will not express dsRNA right away when it is uncoated. It needs a step such as second strand DNA synthesis or annealing to the other polarity of vector DNA before expressing dsRNA.

DETAILED DESCRIPTION

Definitions

As used herein, the term "parvovirus" is used with reference to any member of the Subfamily Parvovirinae, including autonomously-replicating parvoviruses and members of the Dependoparvovirus genus. Autonomously-replicating parvoviruses include members of the genera Amdoparvovirus, Aveparvovirus, Bocaparvovirus, Chapparvovirus, Copiparvovirus, Erythroparvovirus, Protoparvovirus, Tetraparvovirus. Exemplary autonomous parvoviruses include, but are not limited to, minute virus of mice (MVM), bovine parvovirus (BPV), canine parvovirus (CPV), chicken parvovirus, feline panleukopenia virus, feline parvovirus (FPV), goose parvovirus (GPV), porcine parvovirus (PPV), Bocavirus, B19 virus, rat virus (RV), H-1 virus (H-1). Other species of feline. Other autonomous parvoviruses are known to those skilled in the art. See, e.g., King A. M. Q., Adams M. J., Carstens E. B. and Lefkowitz E. J. (2012) Virus taxonomy: classification and nomenclature of viruses: Ninth Report of the International Committee on Taxonomy of Viruses. San Diego: Elsevier.).

The genus Dependoparvovirus includes the adeno-associated viruses (AAVs), including but not limited to, AAV type 1 (AAV-1), AAV type 2 (AAV-2), AAV type 3 (AAV-3), AAV type 4 (AAV-4), AAV type 5 (AAV-5), AAV type 6 (AAV-6), avian AAV, bovine AAV, canine AAV, equine AAV, ovine AAV, and the like. The parvovirus particles, capsids and genomes of the present invention are preferably from AAV.

Parvoviruses for use in the present application further include new variants from genetic engineering having further modifications in the PV capsid gene, nonstructural genes, inverted terminal repeats (ITRs), left-end hairpins (LEHs), right-end hairpins (REHs). The parvovirus vectors of the present invention are useful for the delivery of nucleic acids to cells both in vitro and in vivo. In particular, the inventive vectors may be advantageously employed to deliver or transfer nucleic acids to animal cells. Nucleic acids of interest (NAOIs) include nucleic acids encoding RNAs, peptides and proteins, preferably therapeutic (e.g., for medical or veterinary uses) or immunogenic (e.g., for vaccines) peptides or proteins. It may also provide DNA template sequences for gene editing and/or aptamers for targeted delivery.

The term "hybrid parvovirus," as used herein, refers to a parvovirus genome encapsidated within a different (i.e., another, foreign, exogenous) parvovirus capsid. Alternatively stated, the hybrid parvovirus has a parvovirus genome encapsidated within a different parvovirus capsid. As used herein, by "different" it is intended that the AAV genome is packaged within another parvovirus capsid, e.g., the parvovirus capsid is from another AAV serotype or from an autonomous parvovirus.

The term "parvovirus ITR," as used herein, refers to inverted terminal repeats from any parvovirus, which functions in supporting parovirus replication, encapsidation, rescue, integration etc. Parvovirus inverted terminal repeats (ITRs) are also referred as left-end hairpins (LEHs), right-end hairpins (REHs) when their 5' ITR and 3' ITR are different. An "AAV ITR" refers to an inverted terminal repeat flanking the AAV genome. Parvovirus ITRs and AAV ITRs can include ITRs from any parvovirus or any parvovirus serotype, and can further include ITRs with mutations that support AAV replication, encapsidation, rescue and/or integration similar to a wild type ITR.

The term "AAV serotype,' as used herein, refers to any capsids packaged with a genome with at least one AAV ITR. It include any AAV serotypes found in nature or any engineered or chemically modified capids that can packgin AAV genomes. It includes biologically or chemically modified capsids.

The terms "short hairpin DNA" and "shDNA," are used interchangeably herein with reference to a shDNA as described in US 2018/0298380.

The term "scAAV," as used herein, refers to a single stranded AAV vector containing a double-stranded region generated by the absence of a terminal resolution site (TR) from one of the ITRs of the AAV, wherein absence of the TR prevents the initiation of replication at the vector terminus where the TR is not present. A scAAV vector typically contains a wild-type (wt) AAV TR at each end and a mutated TR (mTR) in the middle, connectively joined to the AAV TRs by the double stranded region. The terms "mTR" and "mITR," are used interchangeably herein to mean a mutant inverted terminal repeat as described in U.S. Pat. No. 7,465,583.

The phrases "covalently closed end domain," "cce domain," "single stranded covalently closed end domain," and "SS-CCE domain" are used interchangeably.

The phrase "covalently closed end (cce) parvovirus," as used herein, refers to a linear parvovirus genome that is packaged into a parvovirus capsid, the parvovirus genome comprising self-complementary DNA sequences forming a pair of hairpin structures at the 5' and 3' ends, a double-stranded domain (herein referred to as the "DS domain") between the 5' and 3' ends, and a SS-CCE end. The DS domain is comprised of self-complementary sequences annealing to each other in the genomic DNA. The SS-CCE end comprises non-complementary sequences comprising a closed single stranded region connecting the annealed portions in the DS DS domain. The capsid can be from any parvovirus, including any parvovirus serotype. In preferred embodiments, the cce parvovirus (ccePV) is a cce adeno-associated virus (cceAAV).

The DNA strand in the DS domain may be perfectly complementary or partially complementary over the length of DS domain, such that the complementary sequences can anneal to one another to form stable duplex regions and may form bulged or looped structure in regions of non-complementarity. The regions of non-complementarity may include deletions or insertions in one or both DNA strands such that unique single stranded DNA region(s) may be formed following annealing of the DNA strand to itself. The resulting stem structure(s) may comprise at least 5% of the length of the DS domain. The difference between a cceAAV and a scAAV is that a cceAAV can be more broadly defined in a manner that does not require a mutant TR (mTR). The scAAV is representative of a species within a larger cceAAV genus described herein, which has a unique cce end in the form of a mutant ITR (mITR) or shDNA sequence. The method for preparing scAAV cannot produce the cceAAV vector defined here. However, the method of the present application has the further advantage of providing a more efficient means for producting scAAVs, since the new intermediate template molecules employ two fully functional ITRs, which can be more efficiently replicated in the producer cells as described above.

In linear denatured form, a cce PV or cce AAV has a 5' parvovirus left-end hairpin (LEH) or inverted terminal repeat (ITR), a DS domain, a 3' parvovirus right-end hairpin (REH) or ITR, and a non-complementary region, which accounts for the formation of looped structure in the linear non-denatured from. The 5'ITR and 3'ITR may be identical or different. The DS domain may be perfectly self-complementary or it may have some non-complementary sequences, provided that they do not preclude formation of a stable duplex comprising the DS domain formed by the single strand folding back on or annealing to itself. The homology of the DS domain should allow a stable duplex DNA to be formed in at least one region when the DNA strands in cccPV anneal to one another. The DNA strand in the DS domain may share regions of self-complementarity (or inverse complementarity, in this case) of at least, 80%, 90%, 95%, 96%, 97%, 98%, 99% or 100% over the portion of the DS domain containing annealed sequences. However, given that the DS domain can accommodate insertions or deletions relative to the self-complementary regions, including insertion or deletions of several thousand nucleotides in length, the overall level of homology from one end of the DS domain to the other can be as little as 0.10% or as much as 100%.

The term "aptamer" refers to an oligonucleotide or peptide molecule that binds to a specific target molecule. Aptamers are typically created by a selection process utilizing a large random sequence pool and have a variety of research, industrial and clinical applications. For example, aptamers can be combined with ribozymes to self-cleave in the presence of their target molecule. Moreover, natural aptamers are known to exist in riboswitches. Besides the traditional function of selectively binding a target ligand, an "aptamer" as used herein may more broadly include deoxyribozymes, including DNA enzymes, DNAzymes, and catalytic DNAs comprising DNA oligonucleotides capable of performing specific enzymatic reactions.

The term "guide RNA based nuclease" refers to a nuclease working in conjunction with a guide RNA molecule for DNA editing. The terms "guide RNA" or "gRNA" are used interchangeably with reference to RNA sequences used in DNA editing process with a guide RNA nuclease, such as Cas9.

The term "guide DNA based nuclease" refers to a structure-guided endonuclease (SGN) used in conjunction with a guide DNA molecule for DNA editing. The terms "guide DNA" or "gDNA" are used interchangeably with reference to DNA sequences used in DNA editing process with a guide DNA nuclease, such as zinc finger nucleases (ZFNs), transcription activator-like effector nuclease (TALENs), and structure guided endonucleases (SGNs), such as a fusion protein comprising the flap endonuclease 1 (FEN-1) enzyme fused to the cleavage domain of the Fok1 endonuclease.

The terms "transcription activator-like effector nuclease" and "TALEN" are used interchangeably with reference to a fusion protein comprising TAL effector DNA-binding domain fused to a DNA cleavage domain.

The term "meganuclease," as used herein, refers to an endodeoxyribonuclease characterized by a large recognition site (double-stranded DNA sequences of 12 to 40 base pairs), typically absent in a given genome. For example, the 18-base pair sequence recognized by the I-SceI meganuclease would on average require a genome twenty times the size of the human genome to be found once by chance (although sequences with a single mismatch occur about three times per human-sized genome). Meganucleases are therefore considered to be the most specific naturally occurring restriction enzymes. Among meganucleases, the LAGLIDADG family of homing endonucleases has become a valuable tool for the study of genomes and genome engineering over the past fifteen years. Meganucleases are "molecular DNA scissors" that can be used to replace, eliminate or modify sequences in a highly targeted way. By modifying their recognition sequence through protein engineering, the targeted sequence can be changed. Meganucleases are used to modify all genome types, whether bacterial, plant or animal. They open up wide avenues for innovation, particularly in the field of human health, for example the elimination of viral genetic material or the "repair" of damaged genes using gene therapy.

The terms "hairpin telomere resolvase" and "protelomerases" are used interchangeably with references to an enzyyme that promotes the formation of covalently closed hairpin ends on linear DNA molecules in certain phages, bacterial plasmids and bacterial chromosomes. Telomere resolvases are mechanistically related to tyrosine recombinases and type IB topoisomerases and are also believed to play a role in the genome plasticity that characterizes *Borrelia* species. Duplication of the DNA molecule results in replicated telomeres (rTel, also referred to as dimer junctions) that are recognized and processed in a DNA breakage and reunion reaction promoted by a hairpin telomere resolvase. The reaction products are covalently closed hairpin telomeres at both ends of linear monomeric DNA molecules. Examples of telomere resolvases include, but are not limited to, telomere resolvase from phages, such as *E. coli* phage N15, *Klebsiella oxytoca* phage φKO2, *Yersinia enterocolitica* phage PY54, and bacterial species, such as *Agrobacterium tumefaciens*, Lyme spirochete *Borrelia burgdorferi*, relapsing fever borreliae *B. hermsii*, *B. parkeri*, *B. recurrentis*, *B. turicatae*, and avian spirochete *B. anserina*.

The present application generally relates to an isolated parvovirus (PV) DNA molecule which has a covalently closed end (cce) configuration when folded back on itself, which can be packaged into a parvovirus capsid. The present application further relates to methods for producing covalently closed end parvovirus (ccePV) vectors.

Figure 1:
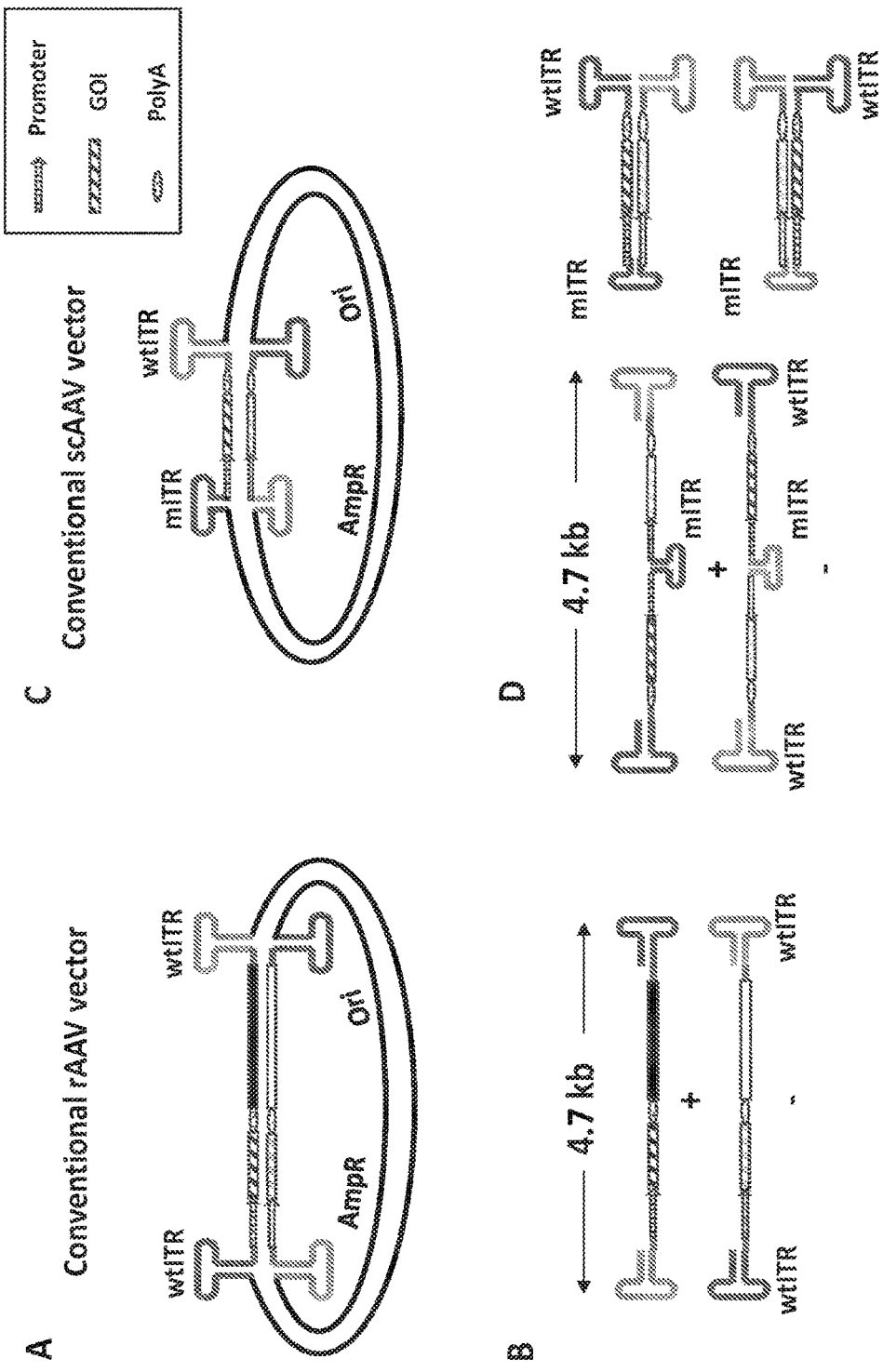
FIG. 1, panel (A) shows a conventional recombinant AAV (rAAV) vector plasmid for producing a single stranded AAV genome with wild type ITRs flanking an expression cassette encoding a gene of interest (GOI). The single stranded AAV genomes in panel (B) are packaged in AAV particles. Panel (C) shows a conventional self-complementary AAV (scAAV) vector plasmid for producing a double stranded scAAV genome formed from the single stranded precursors depicted in panel (D) (left side) that fold back or anneal to themselves via the self-complementary sequences on either side of an mITR. In this case, the single stranded vector genome includes wild-type ITRs (wtITRs) on either end. Vector genomes packaged into virus particles are shown in the right side of panel (D), which illustrates annealing of the complementary regions to form the double-stranded scAAV genomes shown. The two plasmids in panels (A) and (C) can grow stably in a bacterial host.
Figure 2:
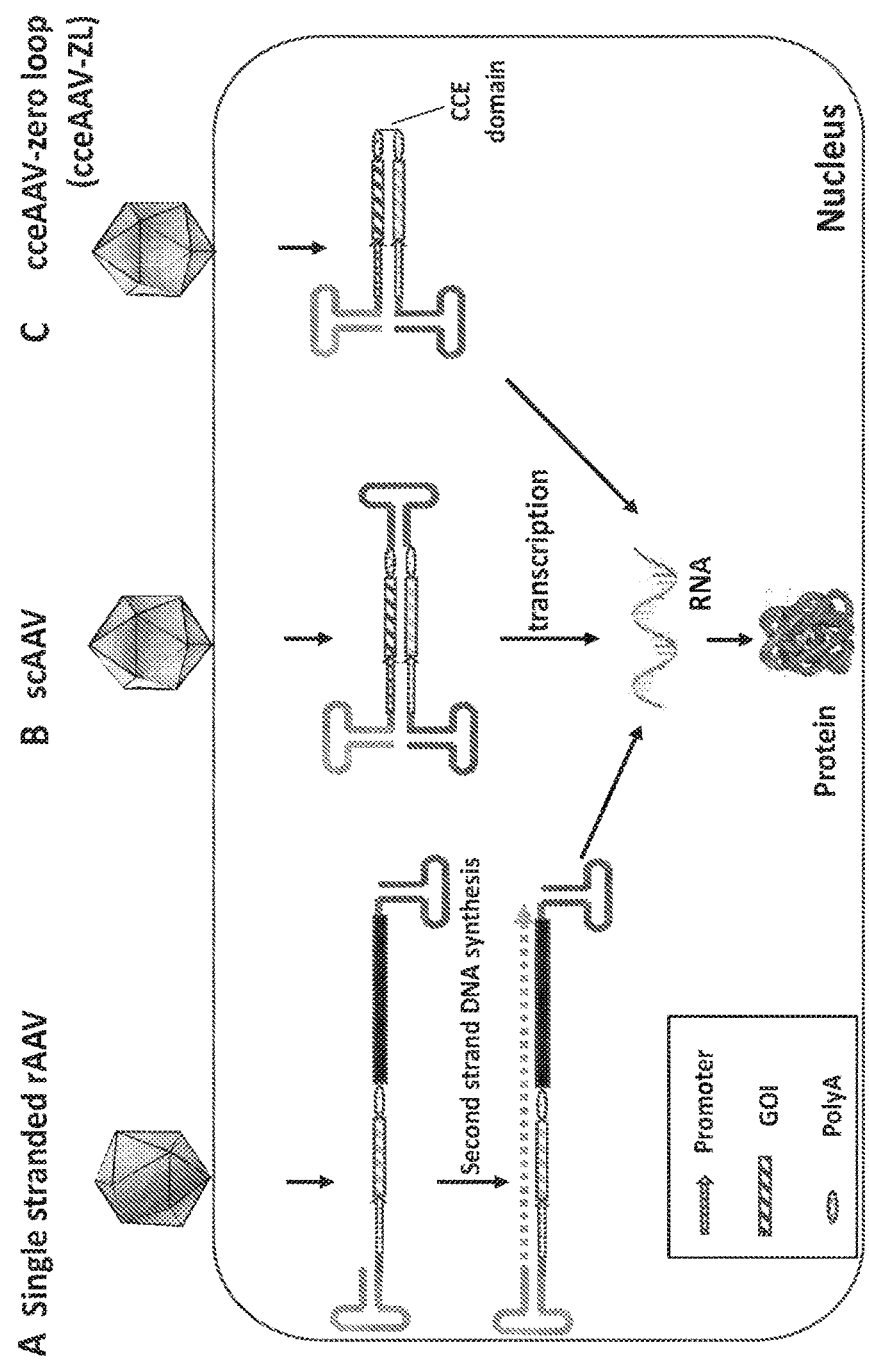
FIG. 2 shows pathways of transgene expression from different packaged AAV templates. Panel (A) shows second strand synthesis from single stranded recombinant AAV (rAAV) DNAs to form double stranded DNA templates for transgene expression; panel (B) shows an scAAV comprising a duplex DNA with a covalently closed end (CCE) domain at the 3' end, which can facilitate transcription of a transgene without the intermediate second strand synthesis step illustrated in panel (A). Panel (C) shows a cceAAV-ZL having a perfectly complementary genome, including a CCE domain, which is not an mTR or shDNA. In panel (C), the CCE domain typically includes a ssDNA region of a few nucleotides (2-5 nucleotides) to allow for a stable stem structure to be formed. Compared to a scAAV, an mTR or shDNA is not required in the cceAAV-ZL illustrated in panel (C). This allows for increased packaging capacity in cceAAV-ZL compared to otherwise identical scAAV vectors.

FIG. 1, panel (A) shows a conventional double-stranded (ds) parvovirus vector plasmid, specifically, an adeno-associated virus (AAV) vector plasmid comprising wild type ITRs flanking an expression cassette comprising a promoter operably linked to a gene of interest (GOI) and a 3' poly A signal. Replication of the ds AAV plasmid in panel (A) initially results in the formation of the single-stranded (ss) AAV DNA templates shown in panel (B), which are subsequently converted to double-stranded DNA templates for transcription/translation of the transgene sequences following second-strand synthesis as shown in FIG. 2. Panel (C) shows a conventional ds self-complementary AAV (scAAV) vector plasmid comprising a wild-type ITR (wtITR) and a mutated ITR (mITR) flanking an expression cassette comprising a comprising a promoter operably linked to a gene of interest (GOI) followed by a 3' poly A signal. Replication of the ds scAAV plasmid in panel (C) initially results in the formation of the single-stranded (ss) scAAV DNA templates shown in panel (D), which fold back over on themselves to form the double-stranded DNA templates depicted on the right side of panel (D), which provide templates for transcription/translation of the transgene sequences within. The two plasmids in panels (A) and (C) can grow stably in a bacterial host.

FIG. 2 shows transcription-translation pathways for transgene expression from different AAV particles and their corresponding DNA templates. The AAV particles are packaged with single-stranded DNA genomes, similar to those depicted in FIG. 1, panels (B) and (D). Conventional recombinant AAV genomes are single-stranded DNA templates undergo a second strand DNA synthesis step to form double-stranded DNA templates for DNA replication and transgene expression. FIG. 2, panel (A) shows conversion of the ss DNAs to ds DNAs by the second strand synthesis step. Panel (B) shows a scAAV comprising a duplex DNA with a covalently closed end (CCE) domain at the 3' end, which can facilitate transcription of a transgene without the intermediate second strand synthesis step illustrated in panel (A). Since the genome in the scAAV particle is perfectly self-complementary, it folds back on itself forming a mutant ITR (mITR) at the closed end as shown in FIG. 2, panel (B) Thus, the CCE domain in panel (B) is in the form of a mITR. In certain scAAV variants, the closed cce end includes shDNA sequences (not shown). Panel (C) shows an exemplary cceAAV according to one embodiment of the present application, cceAAV-zero loop (ZL). The particular structure in panel (C) also has a CCE domain and a perfectly self-complementary genome that folds back on itself forming a double-stranded AAV containing a pair of ITRs at the 5' end, a double stranded domain (DS domain) and a CCE domain as shown in FIG. 2, panel (C). In this case, however, the CCE domain is not a mITR or shDNA. Instead, the CCE domain in cceAAV-ZL is designed without the need for a mTR or shDNA, which would reduce the efficiency of AAV (and/or PV) production. The cce end in panel (C) appears to contain flush ends at the position where the DS domain end. However, because of spatial steric hindrance in forming the duplex, the single stranded loop includes at least 2 nucleotides.

Unlike a scAAV, the CCE domain in the ccePV or cceAAV vectors of the present application does not require e.g., an mITR or shDNA. This allows for increased packaging capacity in cceAAV-ZL compared to otherwise identical scAAV vectors, but also provides for a number of advantages over scAAV vectors as further described below. A ccePV or cceAAV genome can be divided into four elements, a 5'end ITR (or LEH/REH), a double stranded DNA domain ("DS domain"), a 3' ITR (or LEH/REH), and optionally one or more non-complementary regions forming single stranded loop regions. More particularly, the DS domain and its complementary DNA strand can have any degree of homology and may include deletions and insertions, thereby allowing for the formation of a broad range of ccePV or cceAAV molecules with different structural configurations.

By way of example, FIG. 3, panel (A) shows an embodiment of a cceAAV containing a much longer non-complimentary region of single stranded (ss) DNA than in the cceAAV-ZL vector depicted in FIG. 2, panel (C). FIG. 3, panel (B) shows an exemplary embodiment of another cceAAV containing a single stranded loop region (or bulged region) within a complementary double stranded region. The non-complementary ss DNA can include any DNA sequence, such as an aptamer/DNAzyme encoded sequence, a polypeptide encoded sequence, an miRNA encoded sequence, an shRNA encoding sequence, a polyadenylation signal, or an insulator sequence etc. An aptamer/DNAzyme may be stabilized through its linkage/attachment to the flanking complementary DNA sequences adjacent thereto. Advantageously, the single stranded DNA in ccePV-LS or cceAAV-LS provides an efficient template for gene editing or DNA repair applications.

In one aspect, a covalently closed end parvovirus (ccePV) comprises a cce PV DNA packaged in a PV capsid. Following infection, second-strand synthesis is not necessary for transgene transcription. This is even more advantageous for parvoirus vector that only packages one polarity of vectors. The ccePV genome comprises (1) a double stranded (DS) domain with a first strand having a 3' end and a 5' end, and a second strand having a 3' end and a 5' end, (2) a 3' end parvovirus ITR linked to the 3' end of the first strand, and (3) a 5' end parvovirus ITR linked to the 5' end of the second strand, and (4) a covalently closed end (cce) domain that covalently links the 5' end of the first strand to the 3' end of the second strand. The CCE domain can be any sequence when the parvovirus is not an AAV.

The present application includes further embodiments having a bulged region in the DS domain or a long loop segment with an mTR or shDNA in the cce ends or the CCE domain. Such vector constructs cannot be produced using existing methodologies known in the art, such special molecules/vector are not possible with prior art.

The cce capsid and cce genome of the present application can be derived from the same parvovirus or from different parvoviruses. In some embodiments, the cce capsid and cce genome of the present application are derived from the same parvovirus and same serotype (e.g., AAV2-based capsid and AAV2-based viral genome). In some embodiments, the cce capsid and cce genome of the present application are derived from the same parvovirus, but different serotypes (e.g., AAV2-based capsid and AAV8-based viral genome). In some embodiments, the cce capsid and cce genome of the present application are derived from different parvoviruses (e.g., AAV2-based capsid and B19-based viral genome). In some embodiments, the cce capsid is an AAV capsid and the cce genome is a recombinant AAV genome comprising AAV ITRs.

DS Domain and CCE Domain

In some embodiments, the first strand and the second strand of the DS domain of the parvovirus of the present application are 100% complementary to each other, and the CCE domain consists of a single-stranded DNA of 0-50 nucleotides (cceAAV-ZL). In some other embodiments, the CCE domain consists of a single-stranded DNA of 0-5, 0-10, 0-15, 0-20, 0-25, 0-30, 0-35, 0-40, 0-45, 5-10, 5-15, 5-20, 5-25, 5-30, 5-35, 5-40, 5-45, 5-50, 10-15, 10-20, 10-25, 10-30, 10-35, 10-40, 10-45, 10-50, 15-20, 15-25, 15-30, 15-35, 15-40, 15-45, 15-50, 20-25, 20-30, 20-35, 20-40, 20-45, 20-50, 25-30, 25-35, 25-40, 25-45, 25-50, 30-35, 30-40, 30-45, 30-50, 35-40, 35-45, 35-50, 40-45, 40-50, or 45-50 nucleotides.

In some embodiments, the first strand and the second strand of the DS domain of the parvovirus of the present application are 100% complementary to each other, and the CCE domain is dominated by single-stranded DNA (dominated=>50%) (cceAAV-LS). In some embodiments, the CCE domain comprises a DNA aptamer/DNAzyme. In some other embodiments, the CCE domain consists of a single-stranded DNA of 51-60, 51-75, 51-100, 51-200, 51-500, 51-700, 51-1000, 51-2000, 51-3000, 51-4000, 60-75, 60-100, 60-200, 60-500, 60-700, 60-1000, 60-2000, 60-3000, 60-4000, 75-100, 75-200, 75-500, 75-700, 75-1000, 75-2000, 75-3000, 75-4000, 100-200, 100-500, 100-700, 100-1000, 100-2000, 100-3000, 100-4000, 200-500, 200-700, 200-1000, 200-2000, 200-3000, 200-4000, 500-700, 500-1000, 500-2000, 500-3000, 500-4000, 700-1000, 700-2000, 700-3000, 700-4000, 1000-2000, 1000-3000, 1000-4000, 2000-3000, 2000-4000, or 3000-4000 nucleotides.

In some embodiments, the first strand and the second strand of the DS domain of the parvovirus of the present application are not 100% complementary to each other but have a degree of homology allowing for the formation of stable duplex in one or more regions when the strands fold back on each other. In some embodiments, the first strand and the second strand of the DS domain share a sequence identity of at least 20%, 30%, 40%, 50%, 60%, 80%, 90% or 95%.

In some embodiments, the first strand in the DS domain of the parvovirus of the present application has one or more regions that are complementary to the second strand, and one or more regions that are not complementary to the second strand (cceAAV-BR). In some embodiments, the one or more regions that are not complementary to the second strand comprise a shDNA or DNA aptamer.

In some embodiments, the second strand in the DS domain of the parvovirus of the present application has two or more regions that are complementary to the first strand, and one or more regions that are not complementary to the first strand (ccePV-BR). In some embodiments, the one or more regions that are not complementary to the first strand comprise a shDNA or DNA aptamer.

In some embodiments, one or both of the first and second strands in the DS domain contain deletions or insertions relative to the other strand. Such deletions or insertions allow the formation of a bulged or looped DNA region in the DS domain. In some embodiments, the bulged DNA region contains a shDNA sequence or a DNA aptamer. In some embodiments, multiple bulged or looped DNA regions can be formed. A bulged DNA region may be one or more nucleotides and up to one or more kilobases in length provided that it does not adversely exceed (along with the other DNA sequences) the packaging capacity of the ccePV vector. In some embodiments, the bulged DNA sequence can fold into a DNA aptamer. The double-stranded region in the DS domain helps to stabilize the DNA aptamer. In some embodiments, the bulged DNA comprises regions that are complementary to each other and form a double-stranded stem in the bulged DNA region. In some embodiments, the single-stranded DNA sequence in the bulged DNA region in the DS domain or the single-stranded DNA sequence in the CCE domain is used as a template for gene editing, DNA repair or DNA recombination. In some embodiments, the bulged region is at least 2, 3 or 4 nucleotides in length.

In some embodiments, the DS domain encodes a protein. In some embodiments the DS domain encodes an inhibitory RNA (iRNA) product, such as a shRNA or a micro-RNA (miRNA). In some embodiments, the DS domain comprises one or more expression cassettes, each independently ranging in size from about 0.2 kb to about 3 kb, and adding up to a total size of no more than 4 kb.

ITRs

The 5' end ITR and the 3' end ITR may be identical or different. In linear denatured form, the 5'end ITR is located at the 5' end of the cce genome and the 3' end ITR is located at the 3' end of the cce genome.

In some embodiments, one of the ITR can support DNA replication but lose the function for initiation package. This will allow one polarity of vectors to be produced, which will be necessary when the annealing of plus and minus polarity of vectors is undesirable.

cceDNA Generation

The vector DNA for cceDNA is generated through a ligation reaction or protelomerase reaction. The ligation reactions can be carried out in vivo or in vitro. There is a difference between a ligation for typical subcloning and the ligation here. The ligation here generates the template molecules for cce vector DNA are typically not stable in bacteria. Therefore, the in vitro ligation products are used for production directly. Alternatively, the in vitro ligated products can be amplified further using PCR or LAMP amplification before they are used for vector production. In addition, the digestion can be carried out in vivo (host cells) and utilize host enzyme for ligation and subsequently carry out vector production.

Structural Advantages of the ccePV of the Present Application

As described above, when DNA strands in a ccePV template are folded/annealed to one another, the CCE parvovirus genome of the present application contains a double-stranded domain (DS domain) with a parvovirus ITR/LEH/REH upstream of the DS domain and a covalently closed end downstream of DS domain. The genome of the ccePV vector of the present application can have any nucleotides in the CCE domain, and can accommodate any length from 0 nucleotides to the length allowable, based on the size/packaging constraints characteristic of the particular parvovirus vector (excluding the length of the ITRs and DS domain). Furthermore, the ccePV of the present application does not require 100% complementarity in the DS domain and allows branched DNA sequences at any point in the DS domain.

In the case of cceAAV, the genome of the cceAAV vector of the present application is not limited to a mTR or shDNA and can accommodate a wide range of insertions within the CCE domain. The elimination of the mTR or shDNA sequence in the CCE domain increases the effective packaging capacity and improves vector quality by eliminating inefficient conversion of viral genome by mTR or shRNA, which can lead to contamination of the plasmid sequences. Furthermore, the cceAAV of the present application does not require 100% complementarity in the DS domain and allows branched DNA sequences at any point in the DS domain.

Functional Advantages of the ccePV of the Present Application

Figure 14:
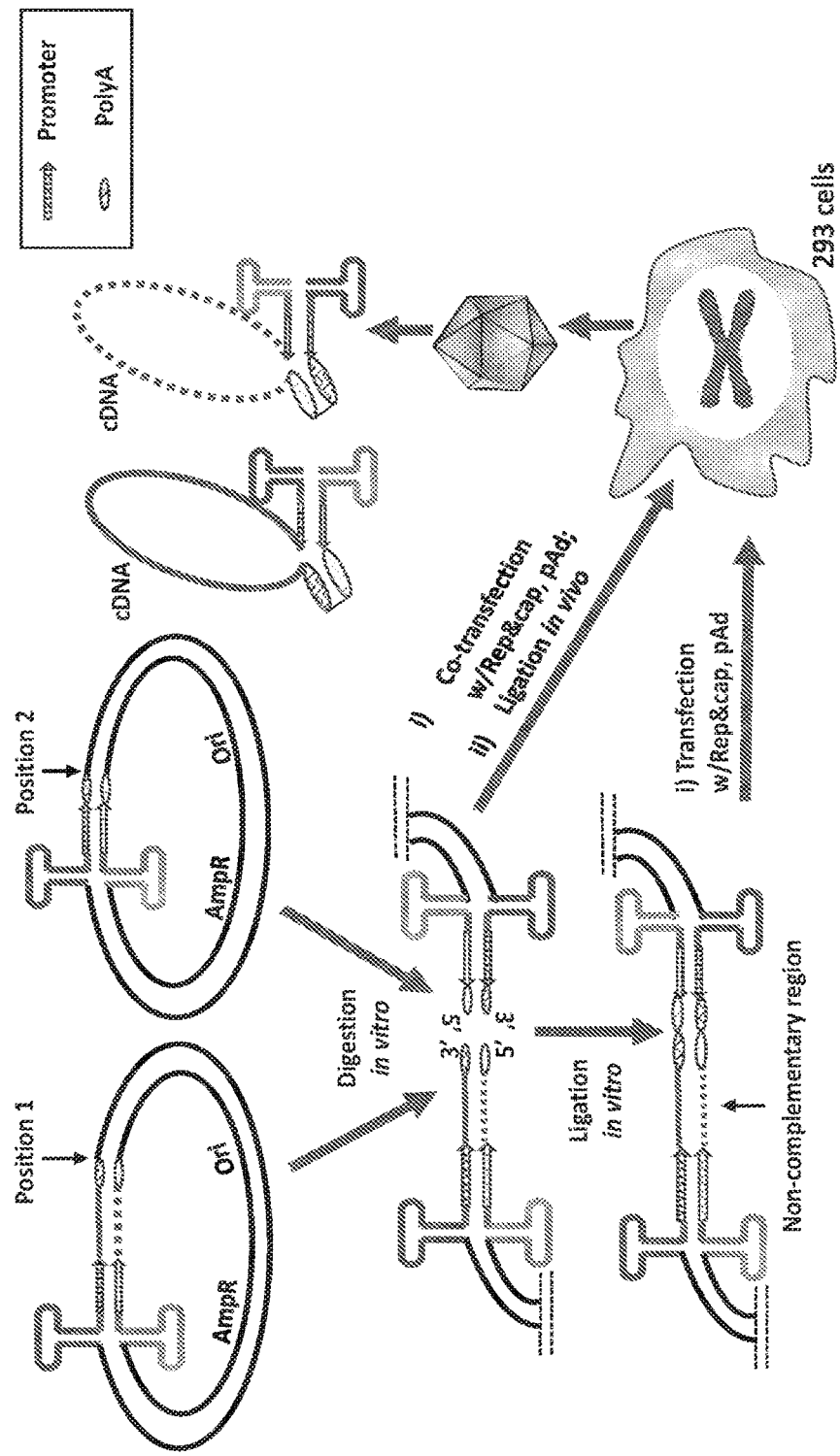
FIG. 14 illustrates an exemplary digestion-ligation strategy to produce a cceAAV vector for extra packaging capacity, based on the general approach outlined in FIG. 13. Two different starting plasmids are utilized. A first plasmid (i.e., left-most plasmid shown) containing an AAV ITR upstream of an expression cassette comprising a promoter, cDNA and poly A site (all poly A sites in this application can be a transcription terminator if a pol III promoter is used) is cut at position 1 with an enzyme 3' of the poly A site, while a second plasmid (i.e., the right-most plasmid) containing an AAV ITR upstream of an expression cassette comprising a promoter, cDNA and poly A site is cut at position 2 with an enzyme 3' of the poly A site. The plasmids can be: (1) digested in vitro, ligated in vitro, and then co-transfected with Rep, Cap, and pAd into AAV producer cells; (2) digested in vitro, and transfected into AAV producer cells, where the digested plasmids are ligated in vivo, or (3) the plasmids can be directly transfected with Rep, Cap, and pAd into AAV producer cells for in vivo digestion and in vivo ligation (not shown). The structures formed thereof comprise two different AAV genomes (top right), each comprising a non-complementary loop region corresponding to a cDNA, both of which are packaged into AAV particles. However, only one of the genomes (plus strand) is capable of expressing the cDNA right after released from the AAV capsids. The AAV plus genomes formed thereof have a configuration of duplex DNA region with full promoter activity driving expression of the single-stranded cDNA region. In contrast, the negative strand can only express the cDNA after the conversion of the ssDNA genome to become a duplex form. Inclusion of the poly A in the second plasmid prevents the production of antisense DNA that could reduce transgene expression when the AAV genome undergoes second strand DNA synthesis. Alternatively, or in addition, a DNA insulator sequence may be incorporated to further reduce this outcome and effectively segregate the transcription units from one another. This can be important, since the self-complementary region includes enhancer sequences, which can function in opposite orientation as well. Non-symmetric digestion can be employed using seamless cloning or other directional cloning techniques to eliminate undesired self-ligation, which may instead lead to the formation of symmetrical ligation products from the first or second plasmids.
Figure 15:
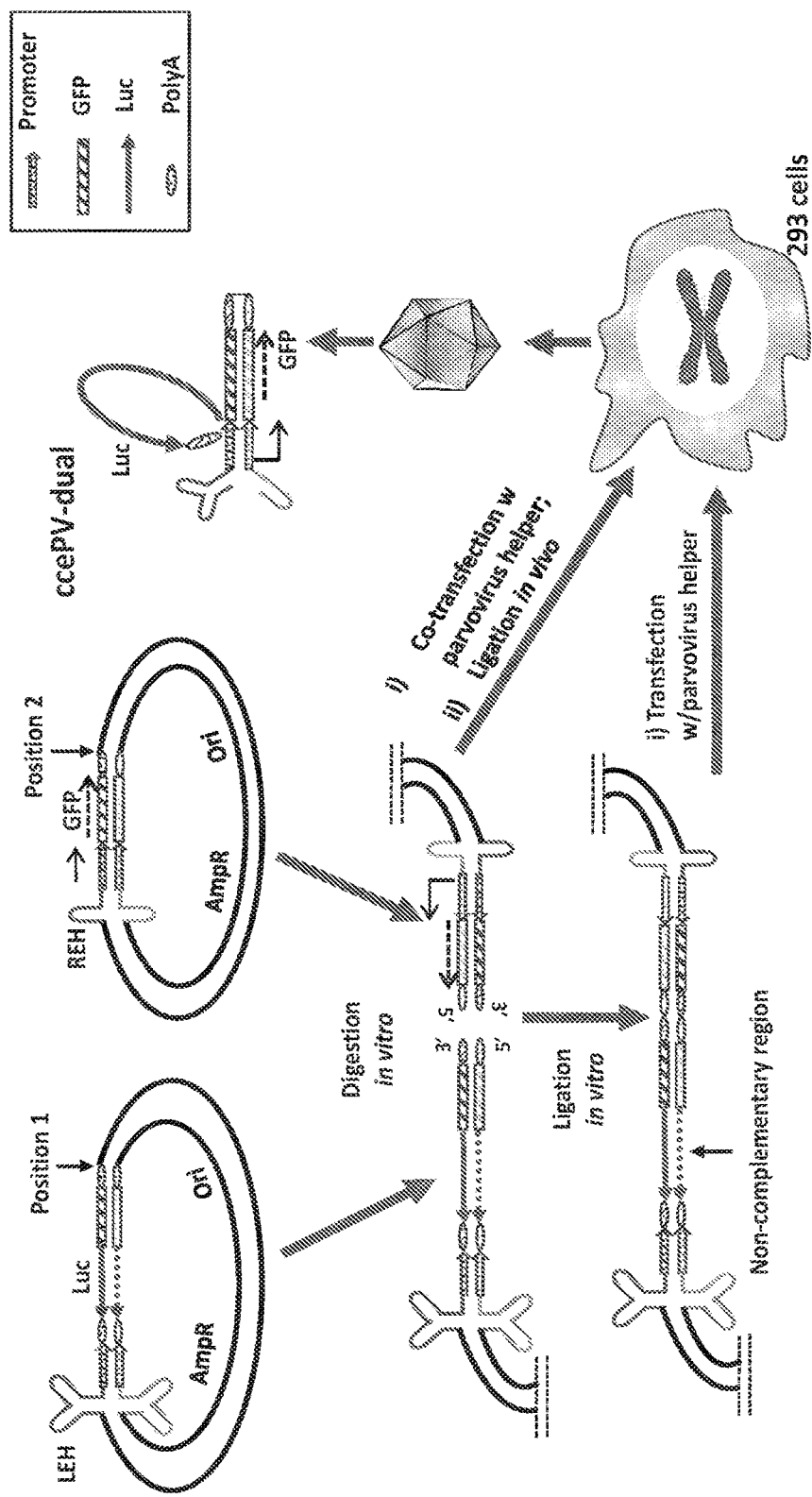
FIG. 15 illustrates another generalized digestion-ligation strategy to produce a ccePV-dual vector for using a single promoter to express two genes. Two different starting plasmids are utilized. The first plasmid (i.e., left-most plasmid shown) contains an LEH region comprising stem-loops structures on opposite strands followed by a promoter in the 5'-3' direction, which is then followed by an expression cassette for the first gene (i.e., luciferase, Luc) in a 3'-5' orientation. Further, the second strand covering the Luc region comprises a non-complementary region. The first plasmid is cut with a first enzyme at position 1, while a second plasmid (i.e., the right-most plasmid) containing a GFP expression cassette is cut with a second enzyme at position 2. The plasmids can be: (1) digested in vitro, ligated in vitro, and then co-transfected with parvovirus helper genes into PV producer cells; (2) digested in vitro, and transfected with parvovirus helper genes into PV producer cells, where the digested plasmids are ligated in vivo, or (3) the plasmids can be directly transfected with parvovirus helper genes into PV producer cells for in vivo digestion and in vivo ligation (not shown). The resulting PV genome packaged into PV particles comprises a non-complementary loop region corresponding to the cDNA (ccePV-dual, top right). The PV genome therefore has a duplex DNA region with the promoter directing the expression of two genes (exemplified by Luc and GFP) with separate poly A sites downstream of each gene. A major feature is that the promoter can turn on the transcription of two genes simultaneously. This can be used to turn off the expression of the second gene when the PV genome undergoes conversion to the duplex form, which places the second transgene (e.g., Luc) in an opposite orientation downstream of the promoter. This is an example of using a PV vector as a genetic switch. Non-symmetric digestion can be employed using seamless cloning or other directional cloning techniques to eliminate undesired self-ligation, which may instead lead to the formation of symmetrical ligation products from the first or second plasmids.
Figure 16:
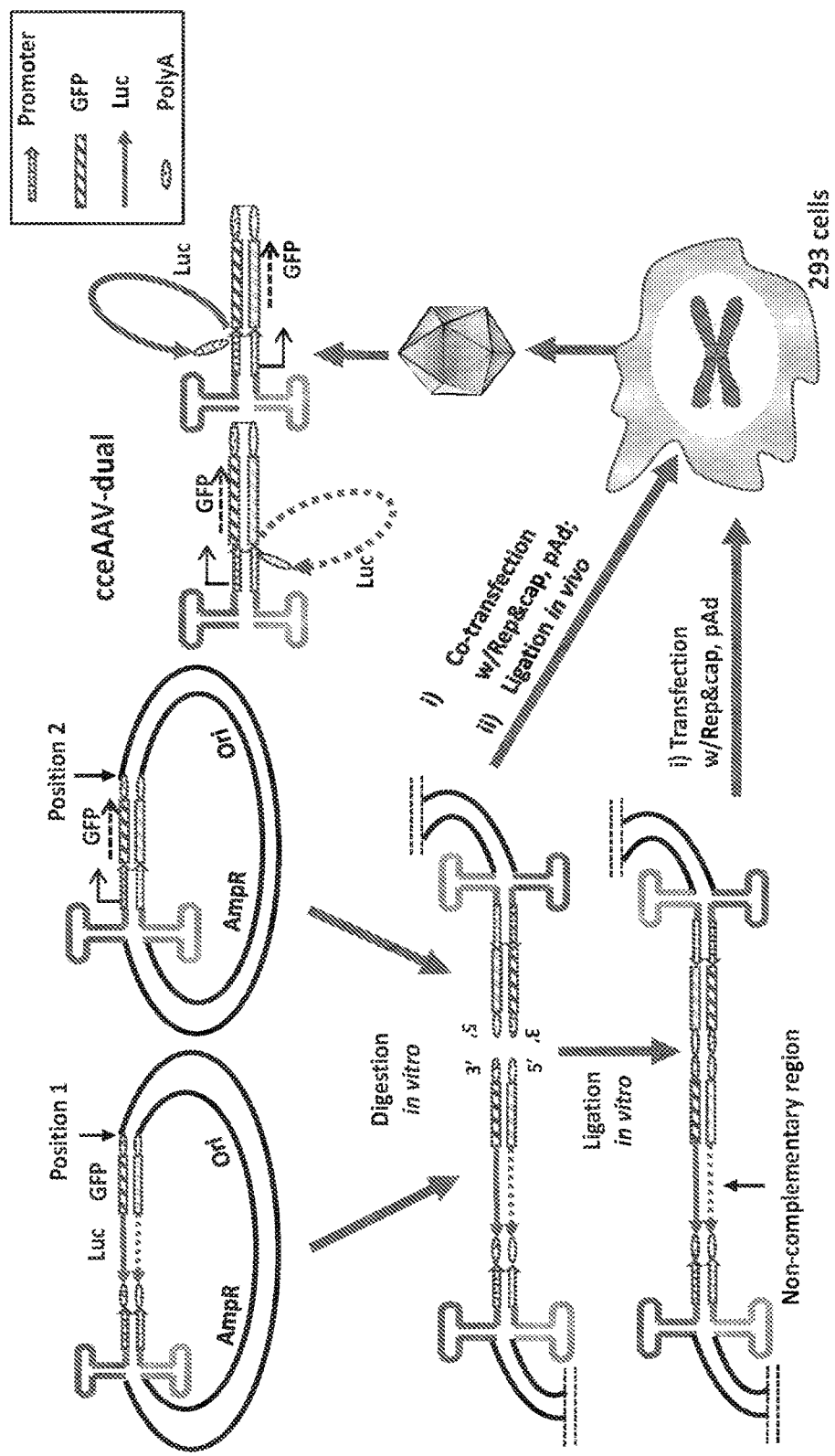
FIG. 16 illustrates an exemplary digestion-ligation strategy to produce a cceAAV-dual vector for using a single promoter to express two genes. Two different starting plasmids are utilized. The first plasmid (i.e., left-most plasmid shown) contains an AAV ITR comprising stem-loops structures on opposite strands followed by a promoter in the 5'-3' direction, which is then followed by an expression cassette for the first gene (i.e., luciferase, Luc) in a 3'-5' orientation. Further, the second strand covering the Luc region comprises a non-complementary region. The first plasmid is cut with a first enzyme at position 1, while a second plasmid (i.e., the right-most plasmid) containing a GFP expression cassette is cut with a second enzyme at position 2. The plasmids can be: (1) digested in vitro, ligated in vitro, and then co-transfected with Rep, Cap, and pAd into AAV producer cells; (2) digested in vitro, and transfected into AAV producer cells, where the digested plasmids are ligated in vivo, or (3) the plasmids can be directly transfected into AAV producer cells with Rep, Cap, and pAd for in vivo digestion and in vivo ligation (not shown). The structures formed thereof comprise two different AAV genomes (top right), each comprising a promoter driving the expression of two genes, where one comprising a non-complementary loop region corresponding to one of the genes (Luc), wherein the other gene (GFP) is encoded in the double-stranded stem upstream of the CCE domain. Both of the genomes are packaged into AAV particles. The AAV genomes formed thereof have a configuration of duplex DNA region with full promoter activity driving expression of two genes, one from the single-stranded region, the other from the double-stranded region. A major feature is that the promoter can turn on the transcription of two genes simultaneously once it releases the genome into host cells after infection. In addition, this can be used to turn off the expression of the second gene when AAV genome undergo the conversion to the duplex, which put the second genome (luc) being in the opposite orientation downstream of the promoter. This is an example of using AAV as a genetic switch. Non-symmetric digestion can be employed using seamless cloning or other directional cloning techniques to eliminate undesired self-ligation, which may instead lead to the formation of symmetrical ligation products from the first or second plasmids.

Compared to a self-complementary adeno-associated virus (scAAV) containing an mTR or shDNA in the CCE domain, which is solely required for viral production, the CCE domain in a cceAAV of the present application can be fully utilized. The CCE domain may contain any sequences and be part of a regulatory element, such as intron, promoter, gene coding region, or an element encoding functional RNA molecules, such as miRNA, antisense RNA, ribozymes, guide DNA. The CCE domain may also encode functional DNA molecules, such as single stranded DNA template for gene editing, guide DNA for DNA-guided endonuclease or DNA aptamers. In some embodiments, the CCE domain further encodes a shDNA that is separated from the DS domain by a single stranded DNA region of at least 10 nucleotides on both ends of the shDNA. In some embodiments, the CCE domain contains a promoter that drives the expression of two different expression cassettes. In other embodiments, the cceAAV or ccePV can be developed as a genetic switch to turn on and off gene expression (FIGS. 14-16).

The ccePVs described herein have the advantage of bypassing the requirement for annealing of positive and negative strands and second strand DNA synthesis, thereby providing enhanced vector genome stabilization and improved gene expression.

Because of the existence of the self-complementary region in the genome of the ccePV of the present application, the ccePV of the present application has enhanced performance in vivo. The genomes the ccePV of the present application are more stable than single-stranded DNA parvovirus vectors. In embodiments where an aptamer/DNAzyme is introduced into the CCE domain of the cce genome, the aptamer is more stable because the aptamer regions are connected to the self-complementary DS domain of the cce genome.

Figure 4:
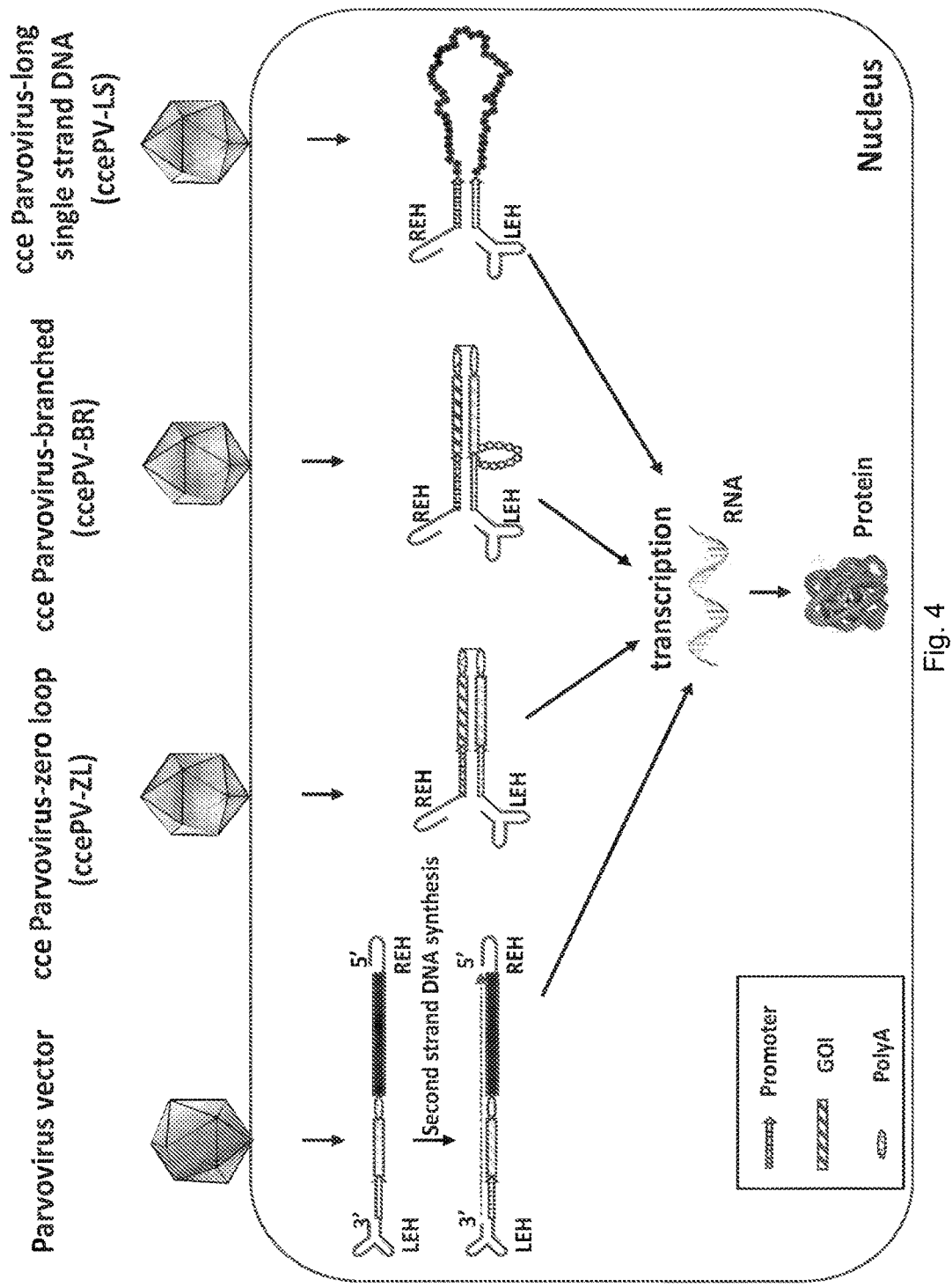
FIG. 4 depicts several parvovirus vectors, including conventional parvovirus vectors and different cce-parvovirus vector embodiments. Panel (A) depicts a conventional parvovirus with a single stranded (ss) DNA genome. Panel (B) depicts a cce-parvovirus with a complementary double stranded (ds) genome. Panel (C) depicts a cce-parvovirus with a ss loop region on one strand of the ds template. Panel (D) depicts a cce-parvovirus with an extended ss loop region 3' of the gene of interest (GOI), which defines the CCE domain and comprises a non-complementary region. The non-complementary ss sequence can include any DNA sequence, such as an aptamer/deoxyribozymes encoded sequence, a polypeptide encoded sequence, an miRNA encoded sequence, an shRNA encoding sequence, a polyadenylation signal, an insulator sequence etc. An aptamer may be stabilized through its linkage/attachment to the flanking complementary DNA sequences adjacent thereto. The single stranded DNA in ccePV-LS is an efficient template for gene editing or DNA repair applications.

As shown in FIG. 4, ccePVs with no non-matched nucleotides in the DS region, bulged loops or stems in the DS region, or a single-stranded loop at the CCE domain have enhanced gene expression efficiency, because the cce genome of the present application bypass the need for second stranded DNA synthesis. This is especially advantageous for ccePVs carrying a DNA aptamer in its genome, since many parvoviruses comprise negative-sense DNAs and are packaged in a 3'-to-5' direction; when there is only one polarity, the DNA aptamer in the ccePV genome has no complementary strand and the effects of the aptamers are not adversely affected by the complementary strand.

This invention allows the self-complimentary vectors to be made without a mutant ITR. The rescue of mutant ITR is inefficient, which also allow package of undesired sequences. This new invention not only improves the vector yield, but also improves the vector quality.

In this new invention, the production materials actually have two ITRs as normal vector, which is very efficient. In addition, due to the self-complementary nature of the sequence, such DNA cannot be made in a bacteria because of its instability in bacteria. In addition, the nuclease in vivo digestion for cceAAV and ccePV is very efficient.

This invention avoids using the palindromic sequences or hairpin DNA for rescue. These are similar advantages to the mutant ITR.

This invention allows other control of gene expression in the host cells through DNA template change arising from second stranded DNA synthesis or annealing. The second strand DNA synthesis can cause the template of function to be generated or eliminated. Many configurations of AAV genomes can only be made by this invention. Parvovirus vector can be used to express dsRNA with a single promoter.

In order to produce dsRNA in a parvovirus vector, it may be necessary to use two promoters in the vector, one in negative strand and one in positive strand. However, this method reduces the vector capacity and the molecules have to be annealed to form dsRNA. In the current invention, the dsRNA is in one single RNA transcript and only one promoter is required.

Methods for Making ccePVs

Another aspect of the present application relates to methods for producing the ccePVs of the present application. One major problem for producing ccePV or cceAAV vectors by conventional methods is that the immediate template molecules containing ccePV and cceAAV genome are not stable and compatible for propagation in the bacteria host cells because of the long stretches of DNA repeats. Conventional scAAV vector plasmids avoid this problem by incorporating mTR or shDNA sequences in conjunction with self-complementary regions in the process of AAV production. However, this method has certain disadvantages. For example, a scAAV vector genome is perfectly complimentary in the stem region (corresponding to the DS domain of the ccePV genome of the present application). It is not possible to have bulged regions in the double-stranded stem. In addition, a scAAV has a mTR or shDNA at the end of the stem region (corresponding to the CCE domain of the ccePV genome of the present application). The presence of the mTR or shDNA reduces the capacity of scAAV vectors to accept further insertions into the scAAV vector. The methods of the present application eliminate the requirement for an mTR or shDNA in the CCE domain. When used in the conventional sense, mITRs or shDNAs are inefficient in converting the input DNA (i.e., plasmid duplex) to a direct DNA template compatible for replication and encapsidation during scAAV production and often lead to contaminants with short vector genomes.

Figure 17:
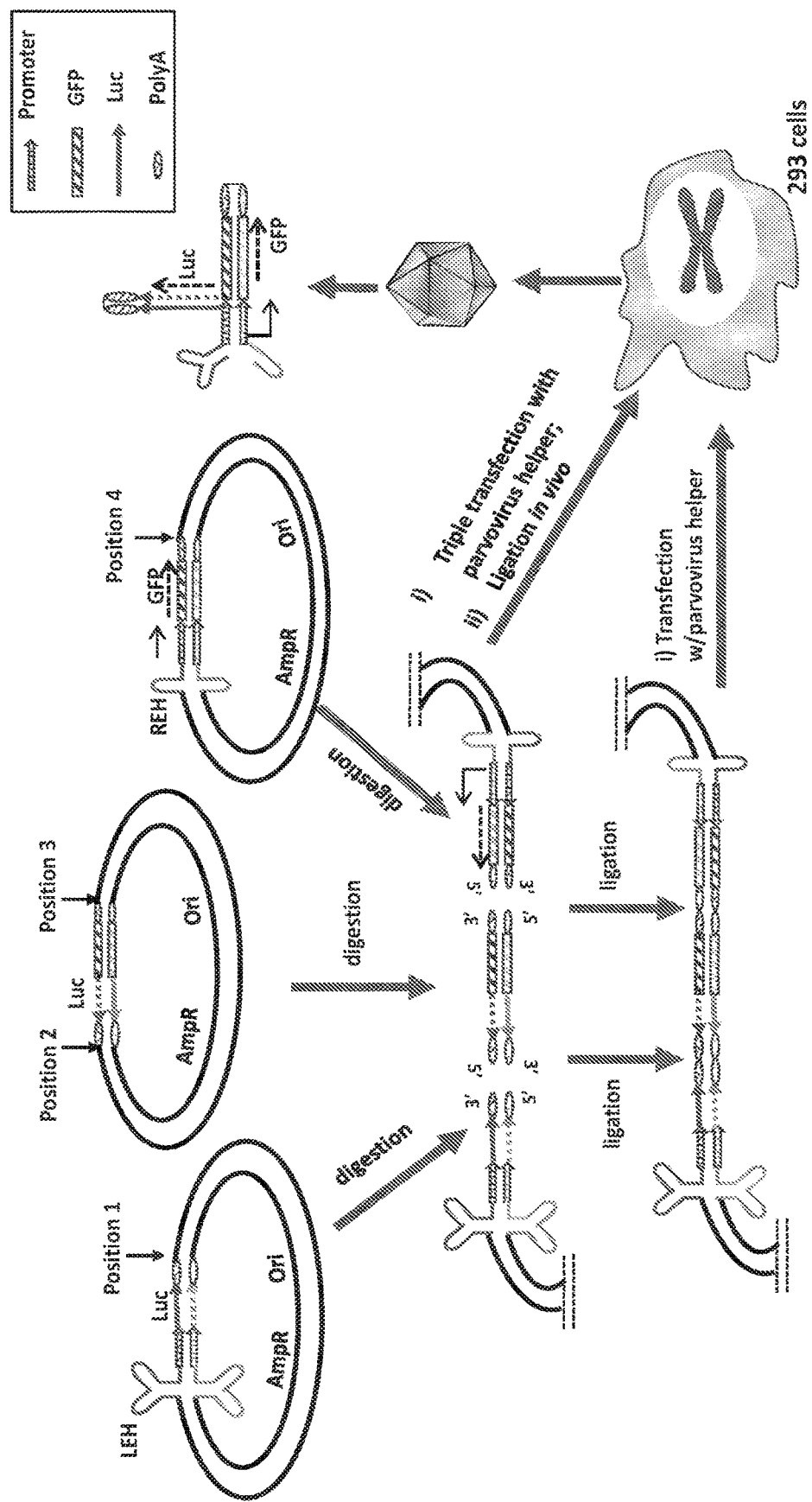
FIG. 17 illustrates a generalized digestion-ligation strategy to produce another ccePV vector comprising a single promoter to express two genes. Three different starting plasmids are utilized. A first plasmid (i.e., the left-most plasmid shown) contains a LEH sequence and an expression cassette for the first gene (e.g., Luc) in a 5'-3' direction that is cut with an enzyme at position 1. A second plasmid (i.e., middle plasmid) contains poly A sites flanking a tandem head to tail arrangement of GFP-Luc coding regions in the 3'-5' direction, which is cut with a second enzyme at positions 2 and 3. A third plasmid contains a REH sequence upstream of a GFP expression cassette, which is cut by a third enzyme at position 4. In this method, the enzymes may be the same or different. The plasmids can be: (1) digested in vitro, ligated in vitro, and then co-transfected with parvovirus helper genes into PV producer cells; (2) digested in vitro, and transfected with parvovirus helper genes into PV producer cells, where the digested plasmids are ligated in vivo, or (3) the plasmids can be directly transfected into PV producer cells with parvovirus helper genes for in vivo digestion and in vivo ligation (not shown). The resulting PV genome packaged into PV particles (top right) comprises a complementary branched region encoding Luc and a duplex DNA region encoding GFP, whereby the single promoter directs the expression of each gene with separate poly A sites downstream of each gene. Thus, a major feature of this arrangement is that the promoter can drive transcription of two genes simultaneously. Moreover, because of this arrangement, the two genes will continue to be expressed even after folding back of the strands into the duplex formation depicted.
Figure 18:
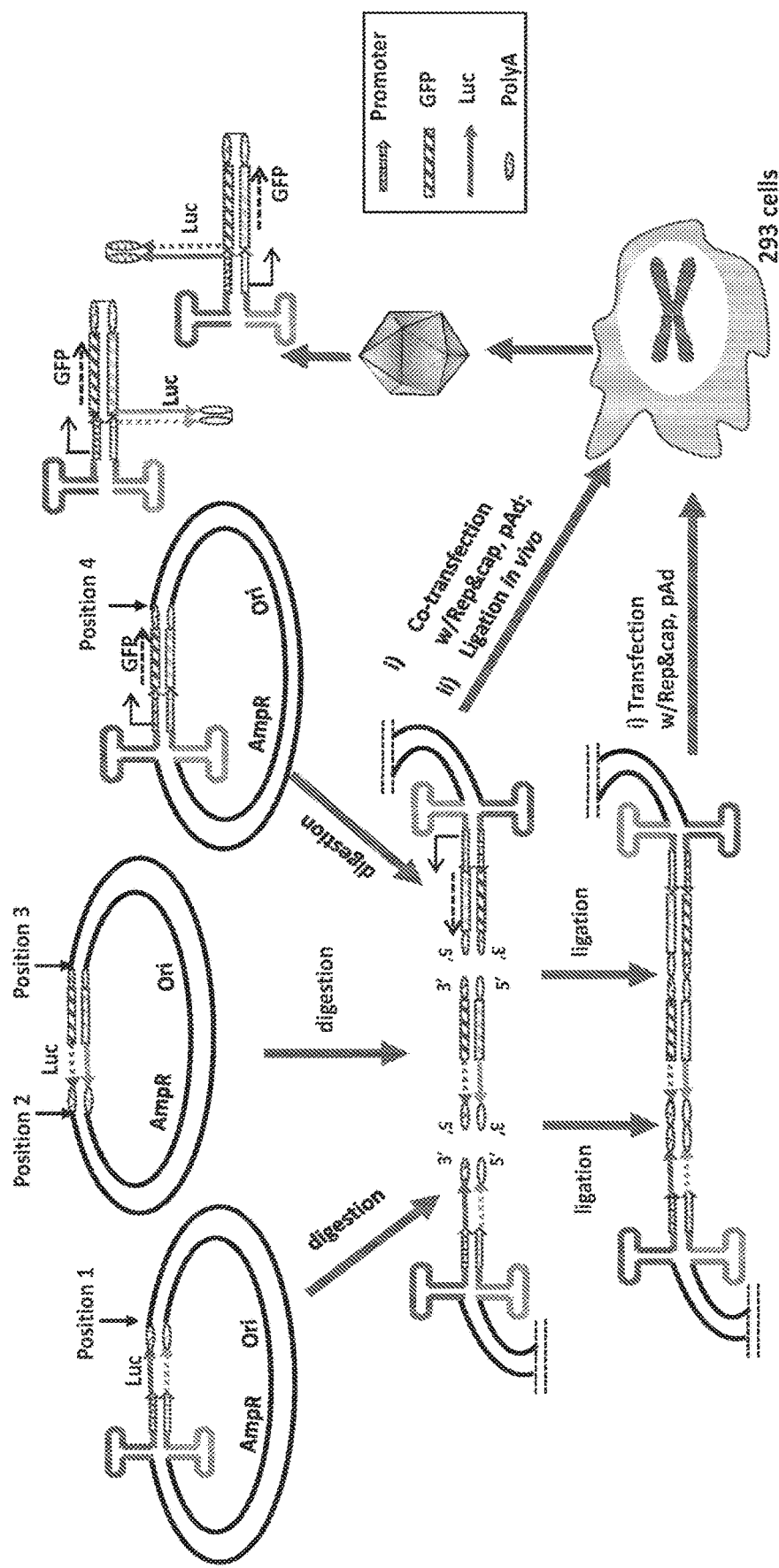
FIG. 18 illustrates an exemplary digestion-ligation strategy to produce a cceAAV vector comprising a single promoter to express two genes, based on the general approach outlined in FIG. 17. Three different starting plasmids are utilized. A first plasmid (i.e., the left-most plasmid shown) contains an AAV ITR and an expression cassette for the first gene (e.g., Luc) in a 5'-3' direction that is cut with an enzyme at position 1. A second plasmid (i.e., middle plasmid) contains poly A sites flanking a tandem head to tail arrangement of GFP-Luc coding regions in the 3'-5' direction, which is cut with a second enzyme at positions 2 and 3. A third plasmid contains an AAV ITR upstream of a GFP expression cassette, which is cut by a third enzyme at position 4. In this method, the enzymes may be the same or different. The plasmids can be: (1) digested in vitro, ligated in vitro, and then co-transfected with parvovirus helper genes into AAV producer cells; (2) digested in vitro, and transfected into AAV producer cells, where the digested plasmids are ligated in vivo, or (3) the plasmids can be directly transfected into AAV producer cells with parvovirus helper genes for in vivo digestion and in vivo ligation (not shown). As a result of either of these three pathways, two different AAV genomes are packaged into AAV particles (top right). Each genome comprises a complementary branched region encoding Luc and a duplex DNA region encoding GFP, whereby the single promoter directs the expression of each gene with separate poly A sites downstream of each gene. Thus, a major feature of this arrangement is that the promoter can drive transcription of two genes simultaneously. Moreover, because of this arrangement, the two genes will continue to be expressed even after folding back of the strands into the duplex formation depicted.

The starting material(s) for making a ccePV or cceAAV comprise one or more template vector(s) in the form of a plasmid, yeast shuttle vector, virus and/or chemical synthesized template. In one embodiment, the starting material(s) include one or more plasmid(s), at least one of which comprises a parvovirus ITR, LEH or REH followed by a DS domain and one or more endonuclease cleavage site(s). The restriction site can be designed to avoid leaving any unnecessary sequences in the vector. Digestion of the template(s) generates one or more DNA fragment(s) containing the ITR and the DS domain. In some embodiments, including the embodiment exemplified in FIG. 17, one or more of the plasmids do not include a parvovirus ITR, LEH or REH or a DS domain as described herein.

In order to produce a ccePV or cceAAV virus particle in accordance with the present application for nucleic acid transfer applications, ccePV DNA template molecules for replication are first prepared (by recombinant DNA technology), followed by extracellular digestion and/or ligation, intracellular digestion and/or ligation, or a combination thereof, and then transfected or stably integrated into suitable PV producer cells as depicted in FIGS. 5-22.

In a particular embodiment, a method for producing a ccePV or cceAAV particle of the present application (as described herein) comprises the steps of: introducing a PV template molecule into a suitable host cell under conditions permitting parvovirus replication; maintaining the cell under conditions sufficient to produce a ccePV vector particle; and harvesting the ccePV from the cultured host cell.

To provide conditions suitable for parvovirus replication, parvovirus helper gene expression plasmids encoding e.g., PV rep and cap genes may be transiently or stably transfected into host cells suitable for PV production, including but not limited to 293 cells. Alternatively, a suitable helper virus may be introduced into host cells to provide necessary helper virus functions for PV production.

In some embodiments, ccePV template molecule(s) may be transiently or stably transfected into host cells suitable for PV production, including but not limited to 293 cells. Alternatively, the ccePV template molecule(s) may be introduced into host cell by infection with a suitable carrier virus, such as a vaccinia virus, adenovirus, herpesvirus, baculovirus, etc.

In some embodiments, an in vivo method for gene transfer of ccePV virus particles for expression of one or more proteins and/or delivery of one or more non-coding sequences comprises the steps of administering to the host an effective amount of ccePV virus particles so that the one or more proteins are expressed in the host cell or so the one or more non-coding sequences are delivered to the host cell for their intended purpose or a combination thereof. In preferred embodiments, the host is a mammal. In some embodiments, the ccePV virus particles contain a nucleic acid comprising an expression cassette encoding a therapeutic protein or therapeutic RNA in a subject in need thereof.

1. In Vitro Digestion and In Vitro Ligation of a Single DNA Template

Figure 5:
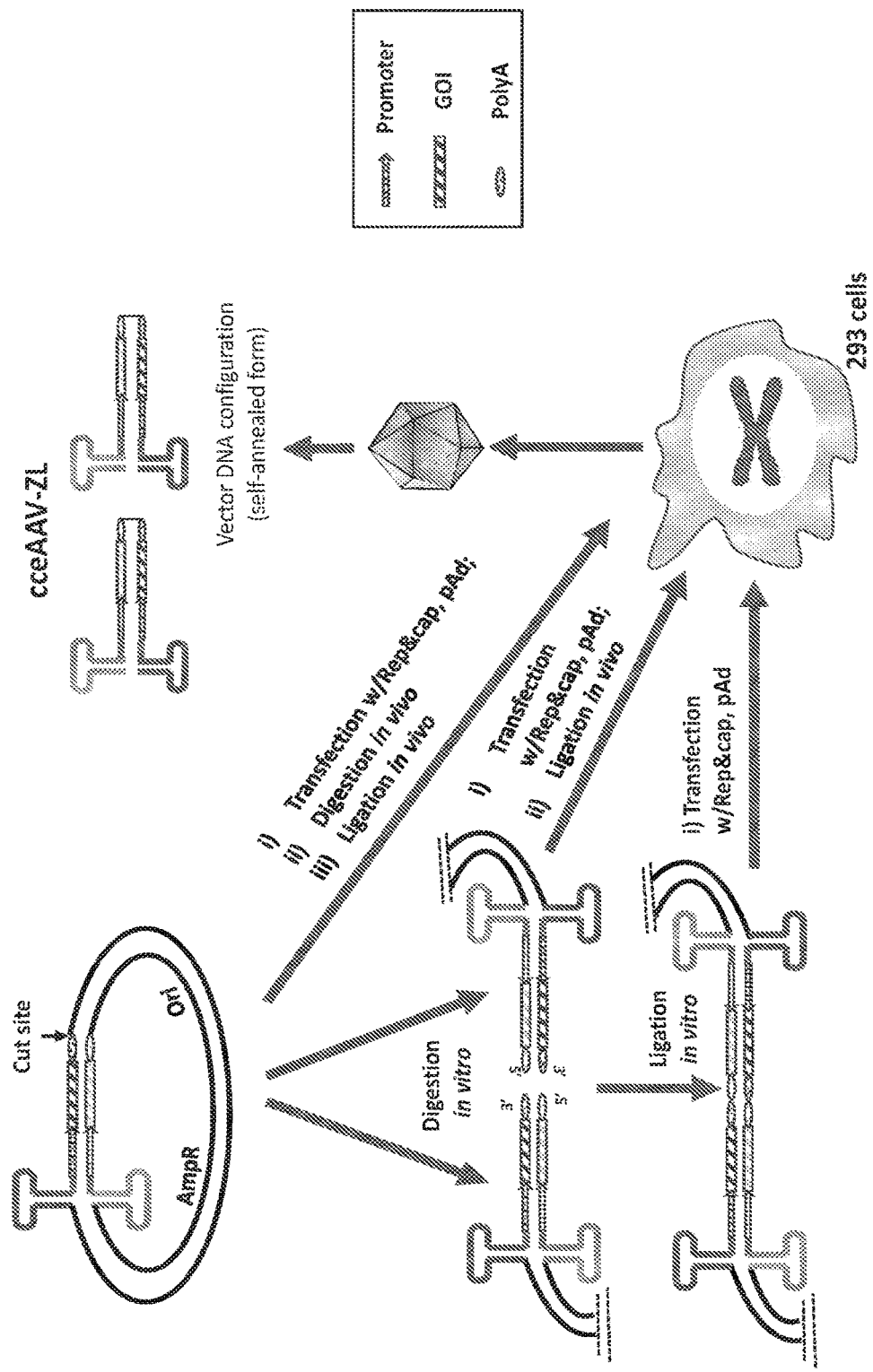
FIG. 5 illustrates an exemplary ligation strategy to produce a cceAAV-ZL vector. First, a starting plasmid with an AAV ITR and an expression cassette encoding a gene of interest (GOI) is engineered to include a recognition sequence at the 3' end of the expression cassette to facilitate digestion (or linearization) by an enzyme of interest. The resulting fragment can be subject to three different pathways for producing cceAAV-ZL particles containing two ITRs with a 3' CCE domain. The starting plasmid can be: (1) digested (i.e., linearized) in vitro, ligated in vitro and then transfected in AAV producing cells (e.g., 293, or any other cells with complementary genes supplied) transfected with Rep, Cap and pAd (with additional adenovirus helper genes not supplied in the producing cell line; (2) digested (i.e., linearized) in vitro, transfected with Rep, Cap and pAd in AAV producing cells, and ligated in vivo; or (3) directly transfected in with Rep, Cap and pAd in AAV producing cells, where the starting plasmid is digested in vivo and ligated in vivo. As a result, cceAAV-ZL genomic DNA (top right) is produced and packaged into virus particles. The illustration here is for AAV produced in 293 cells using an adenovirus helper. Other helper systems that can be utilized for the proposed digestion/ligation methods include herpes virus, vaccinia virus and baculovirus based systems. The vector plasmids can also be present in the host cells in stable episomal forms prior to the digestion/ligation steps to form the template molecules corresponding to the ccePV and cceAAV vectors produced.
Figure 6:
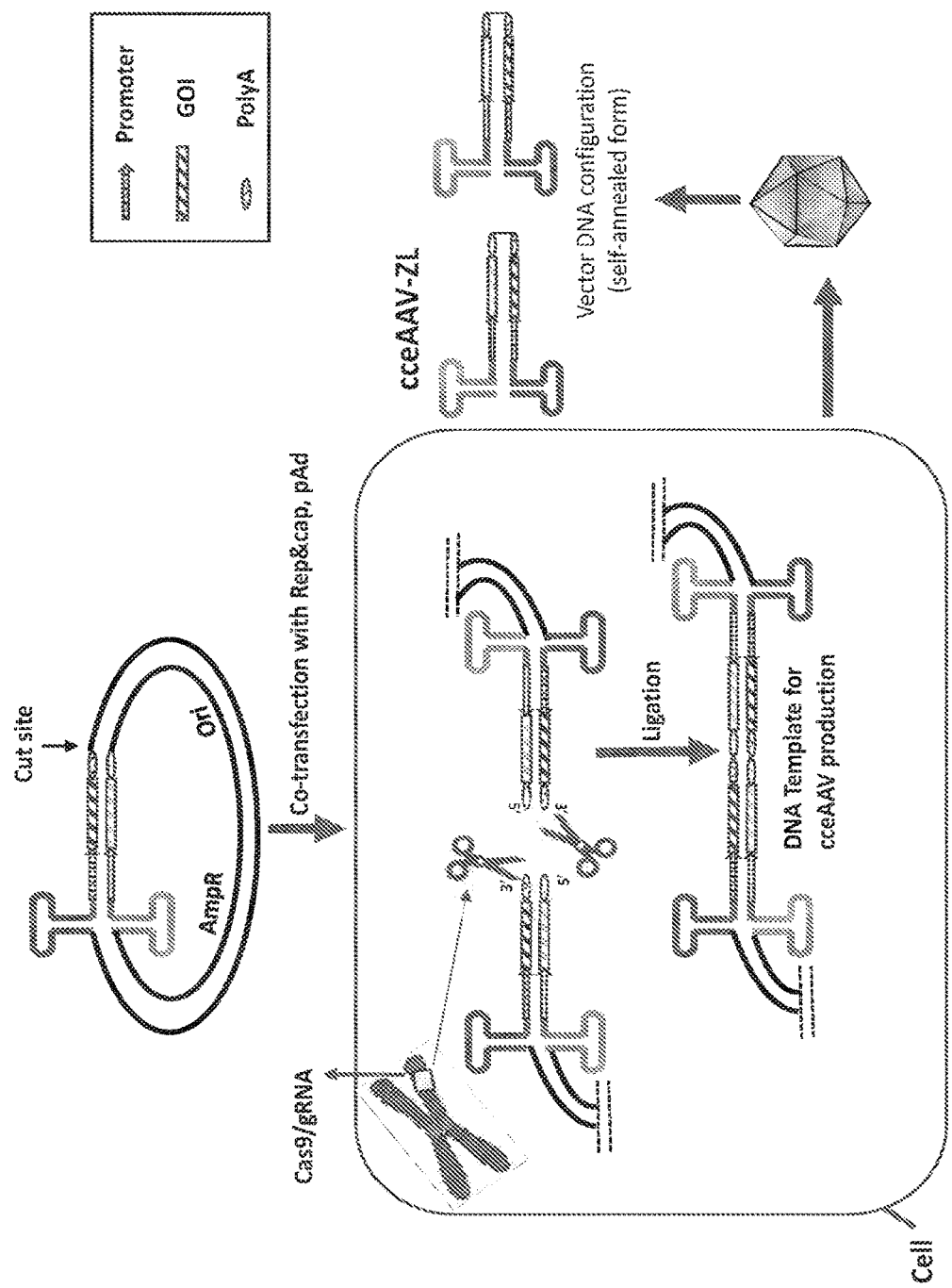
FIG. 6 further illustrates an exemplary in vivo digestion-ligation strategy to produce a cceAAV-ZL vector. The starting plasmid includes an AAV ITR and an expression cassette encoding a gene of interest (GOI) is engineered to include a recognition sequence at the 3' end of the expression cassette to facilitate in vivo digestion (or linearization) by an enzyme of interest. The plasmid is co-transfected with Rep, Cap, and pAd into an AAV producer cell (e.g., 293) with the enzyme for the linearization reaction. The enzyme can be delivered by a viral vector or stably integrated into the AAV producer cell genome.
Figure 7:
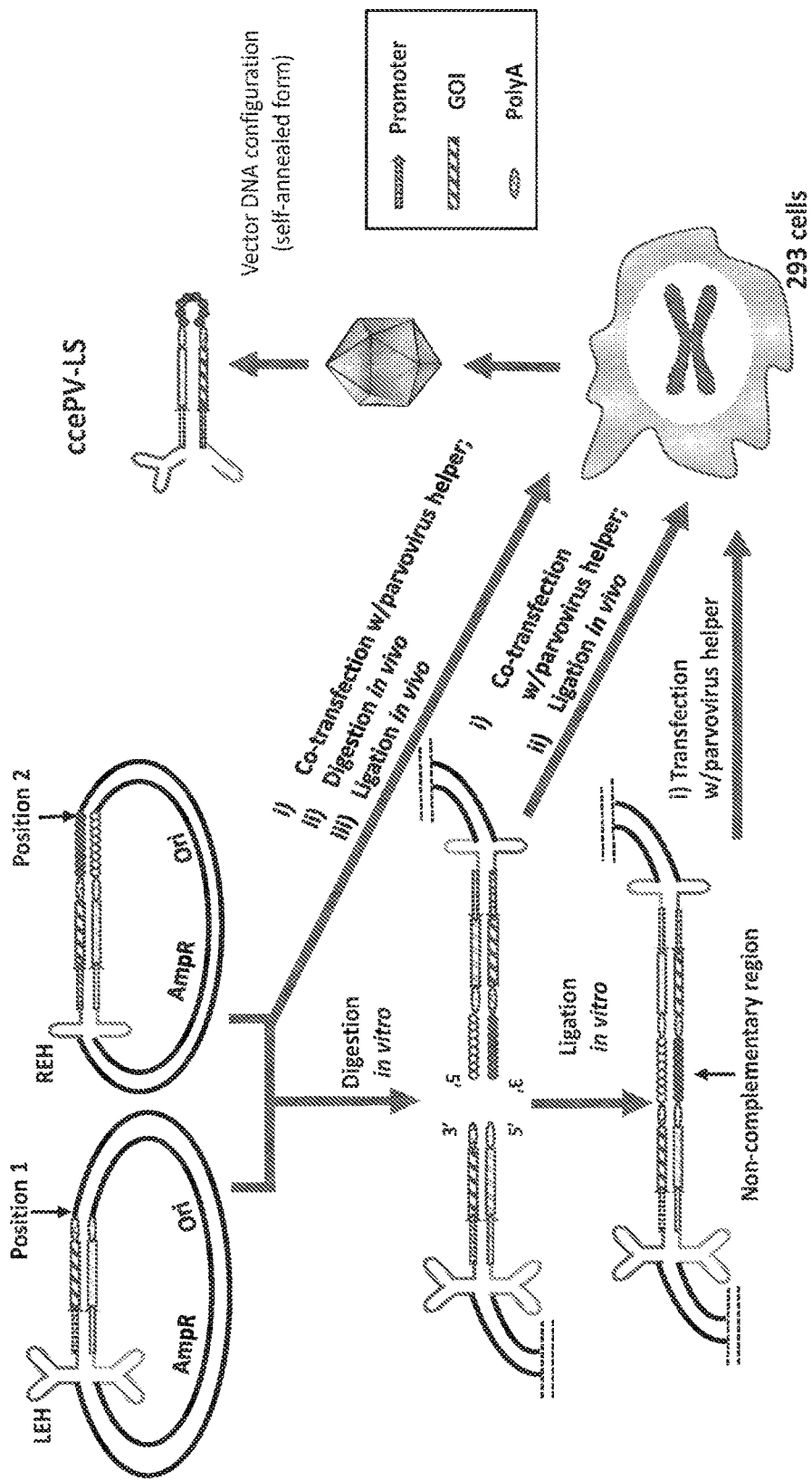
FIG. 7 illustrates an exemplary generalized digestion-ligation strategy for production of a ccePV-LS vector. Two different starting plasmids are utilized. A first plasmid (i.e., left-most plasmid shown) containing a parvovirus (PV) left-end hairpin (LEH), a PV right-end hairpin (REH) and an expression cassette therebetween is cut at position 1 with an enzyme at the 3' end of the expression cassette, while a second plasmid (i.e., the right-most plasmid) containing an additional non-complementary region 3' of the expression cassette is similarly cut downstream of the non-complementary region at position 2. The second plasmid may be cut with the same or different enzyme. The plasmids may be: (1) digested in vitro, ligated in vitro, and co-transfected with parvovirus helper genes into PV producer cells, such as the 293 cell line (or any other cell line compatible with the specific parvovirus vector); (2) digested in vitro, co-transfected with parvovirus helper genes into producer cells, and ligated in the producer cells in vivo; or (3) directly transfected with parvovirus helper genes in PV producing cells, where the starting plasmid is digested in vivo and ligated in vivo. As a result of either of these three pathways, a replication template is produced with LEH and REH sequences flanking the gene of interest (GOI) as shown, including the non-complementary region therebetween for PV vector production in the PV producing cells. Because the ligated fragment includes a non-complementary region, the CCE domain will form an extended single-stranded loop or bulged region as shown in the right top portion of the figure. Non-symmetric digestion can be employed using seamless cloning or other directional cloning techniques to eliminate undesired self-ligation, which may instead lead to the formation of ccePV-ZL. The digestion site in the second plasmid does not need to be at the beginning or the end of the non-complementary region, however; it can be in the anywhere in the middle of non-complementary region. In contrast, when the ends of the first plasmid and the second plasmid are identical or near identical, the resulting vector, ccePV-ZL is produced, which does not have a significant loop at the closed end. The ccePV may package both polarities of vectors or just one polarity. The illustration here only shows one polarity.
Figure 8:
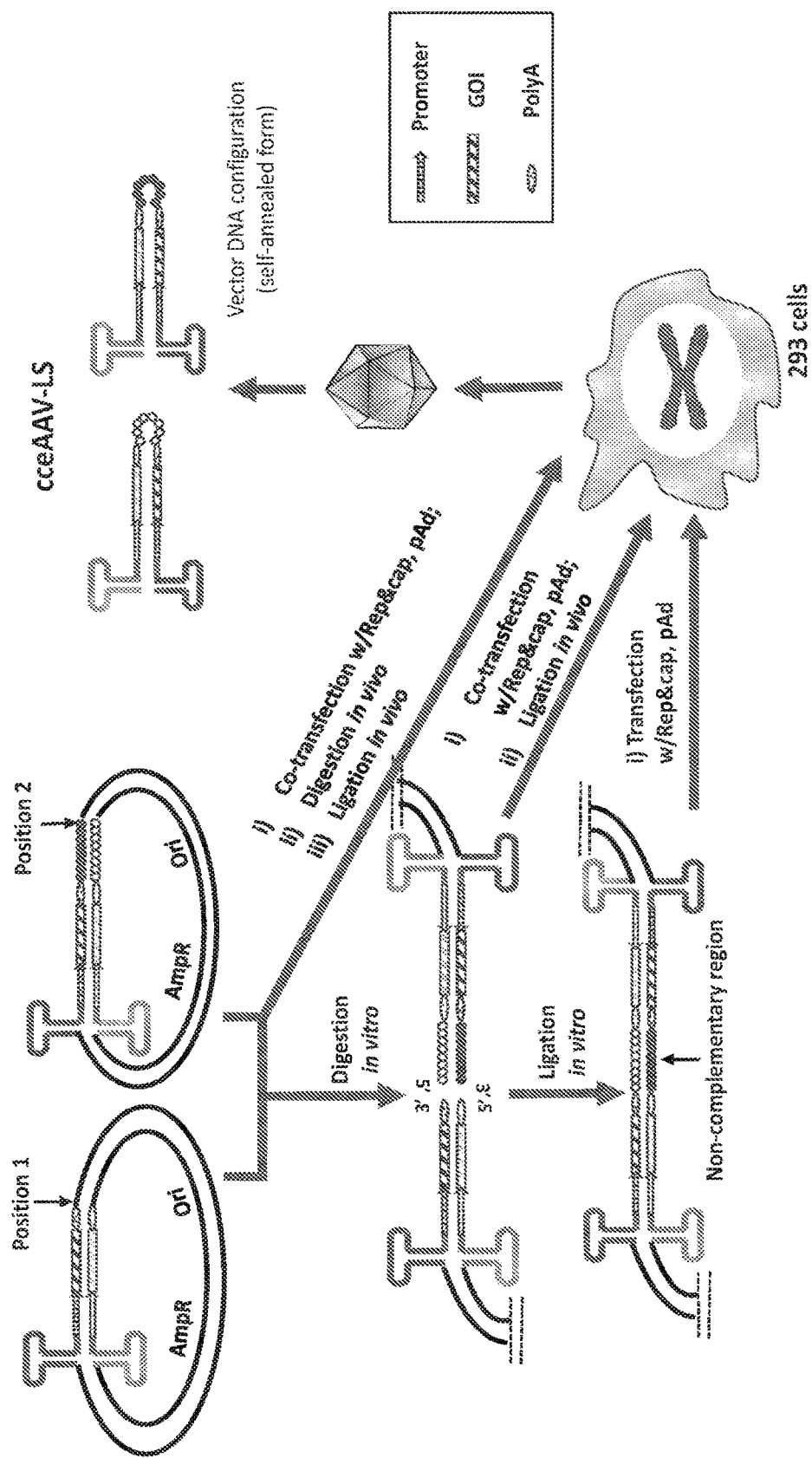
FIG. 8 illustrates an exemplary digestion-ligation strategy to produce a cceAAV-LS vector, based on the general approach outlined in FIG. 7. Two different starting plasmids are utilized. A first plasmid (i.e., left-most plasmid shown) containing an AAV ITR and an expression cassette is cut at position 1 with an enzyme at the 3' end of the expression cassette, while a second plasmid (i.e., the right-most plasmid) containing an additional non-complementary region 3' of the expression cassette is similarly cut downstream of the non-complementary region at position 2. The second plasmid may be cut with the same or different enzyme. The plasmids may be: (1) digested in vitro, ligated in vitro, and co-transfected with Rep, Cap and pAd into AAV producer cells, such as the 293 cell line or other AAV cell lines; (2) digested in vitro, co-transfected with Rep, Cap and pAd into producer cells, and ligated in the producer cells in vivo; or (3) directly transfected in with Rep, Cap and pAd in AAV producing cells, where the starting plasmid is digested in vivo and ligated in vivo. As a result of either of these three pathways, a replication template is produced with ITRs flanking the gene of interest (GOI) as shown, including the non-complementary region therebetween for AAV vector production in the AAV producing cells. Because the ligated fragment includes a non-complementary region, the CCE domain will form an extended single-stranded loop or bulged region as shown in the right top portion of the figure. Non-symmetric digestion can be employed using seamless cloning or other directional cloning techniques to eliminate undesired self-ligation, which may instead lead to the formation of cceAAV-ZL. The digestion site in the second plasmid does not need to be at the beginning or the end of the non-complementary region, however; it can be in the anywhere in the middle of non-complementary region. In contrast, when the ends of the first plasmid and the second plasmid are identical or near identical, the resulting vector cceAAV-ZL is produced, which does not have a significant loop at the closed end. Furthermore, multiple fragment ligations and/or DNA assembly techniques can be used to generate the template molecules for production of cceAAV or ccePV.
Figure 9:
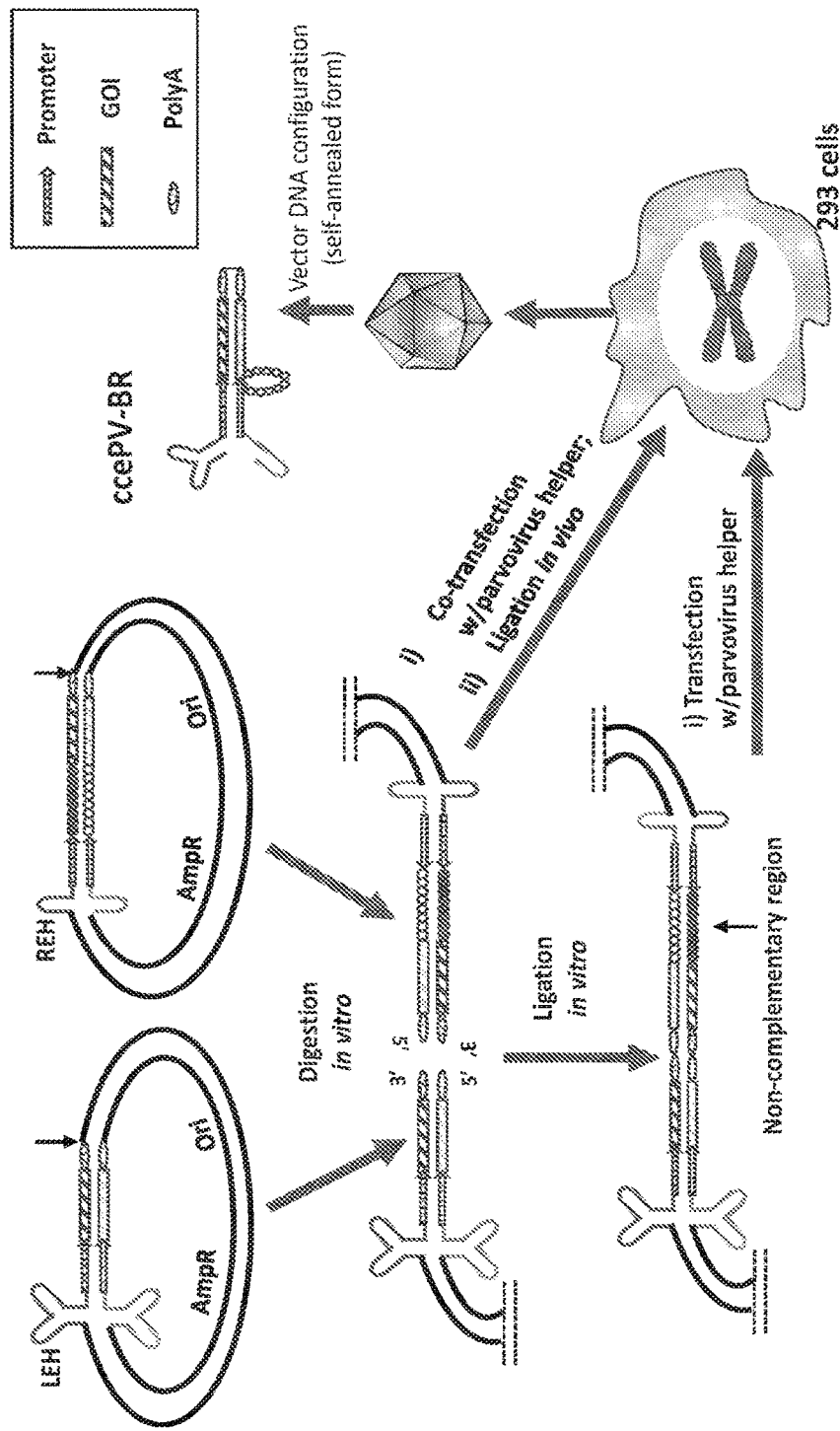
FIG. 9 illustrates a generalized digestion-ligation strategy to produce a ccePV-BR vector. Two different starting plasmids are utilized. A first plasmid (i.e., left-most plasmid shown) containing a PV LEH upstream of an expression cassette containing a GOI is cut at position 1 with an enzyme at the 3' end of the expression cassette, while a second plasmid (i.e., the right-most plasmid) containing an REH, an expression cassette, and an additional non-complementary region between the promoter and the GOI is cut downstream of the expression cassette at position 2. The second plasmid may be cut with the same or different enzyme. The plasmids may be: (1) digested in vitro, ligated in vitro, and co-transfected with parvovirus helper genes into PV producer cells, such as the 293 cell line; (2) digested in vitro, co-transfected with parvovirus helper genes into producer cells, and ligated in the producer cells in vivo; or (3) directly transfected in with parvovirus helper genes in PV producing cells, where the starting plasmid is digested in vivo and ligated in vivo (not shown). As a result of either of these three pathways, a replication template is produced (ccePV-BR, top right) with LEH/REH sequences upstream of a promoter driving expression of the gene of interest (GOI) as shown, as well as a non-complementary region there between. Because the ligated fragment includes a non-complementary region, the CCE domain will form an extended single-stranded loop or bulged region as shown in the right top portion of the figure, which can accommodate additional sequences, such as an aptamer sequence etc. Non-symmetric digestion can be employed using seamless cloning or other directional cloning techniques to eliminate undesired self-ligation, which may instead lead to the formation of symmetrical ligation production from the first and second plasmids. A ccePV-BR with multiple ss loop structures can be formed by including additional non-complimentary sequences. The ss loop(s) in ccePV-BR may comprise an aptamer-encoding region or a single stranded DNA template for gene editing. The nature of parvovirus packaging with a defined polarity means that constructs containing an aptamer sequence, for example, will result in replication templates that are not affected by the complementary strand. The aptamer activity can be maintained until the vector genome is degraded/converted by the host cells.
Figure 10:
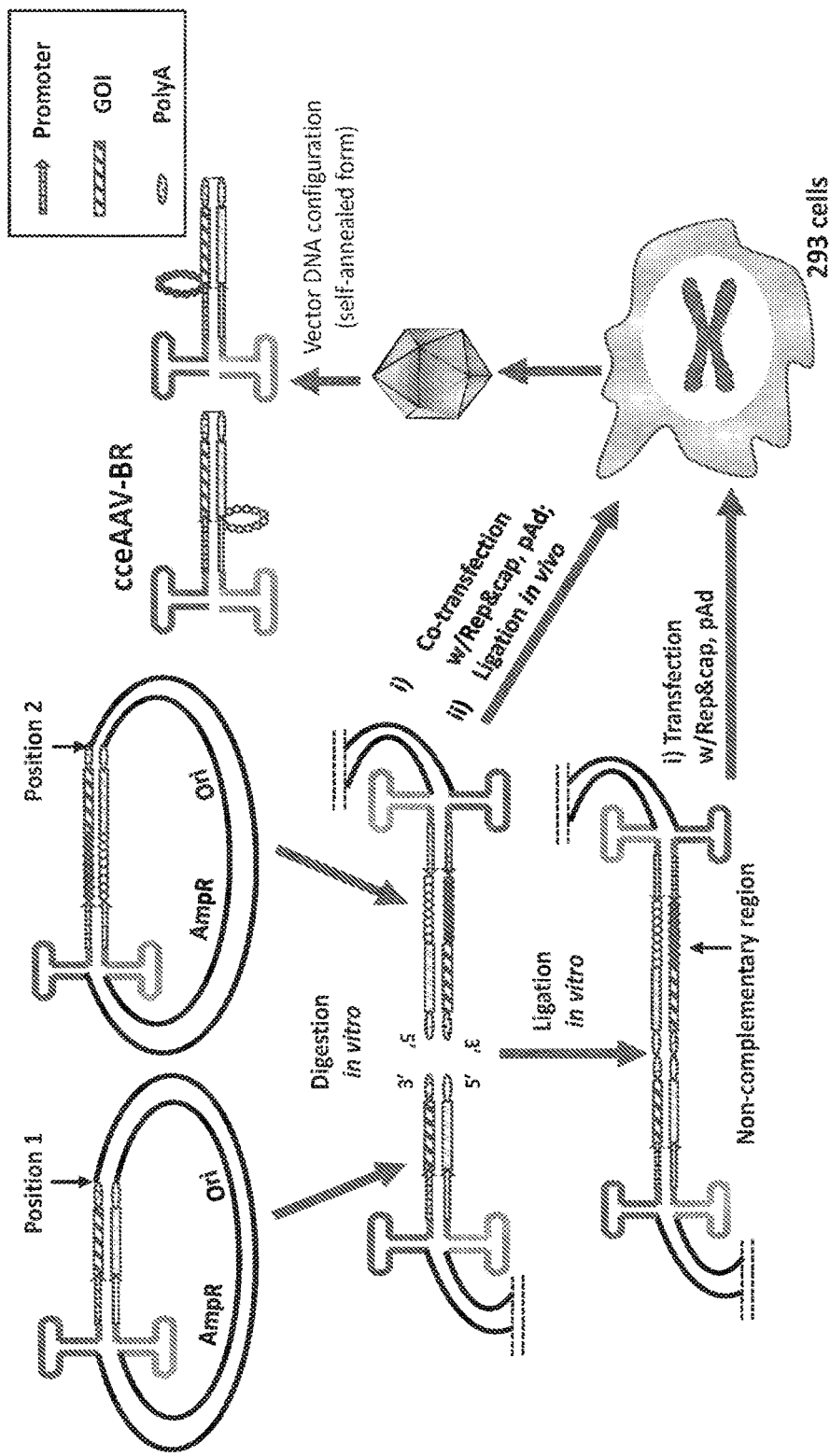
FIG. 10 illustrates an exemplary digestion-ligation strategy to produce a cceAAV-BR vector, based on the general approach outlined in FIG. 9. Two different starting plasmids are utilized. A first plasmid (i.e., left-most plasmid shown) containing an AAV ITR and an expression cassette is cut at position 1 with an enzyme at the 3' end of the expression cassette, while a second plasmid (i.e., the right-most plasmid) containing an additional non-complementary region between the promoter and the GOI is cut downstream of the otherwise identical expression cassette at position 2. The second plasmid may be cut with the same or different enzyme. The plasmids may be: (1) digested in vitro, ligated in vitro, and co-transfected with Rep, Cap and pAd into AAV producer cells, such as the 293 cell line or other compatible cells; (2) digested in vitro, co-transfected with Rep, Cap and pAd into producer cells, and ligated in the producer cells in vivo; or (3) directly transfected with Rep, Cap and pAd in AAV producing cells, where the starting plasmid is digested in vivo and ligated in vivo (not shown). As a result of either of these three pathways, a replication template is produced (cceAAV-BR, top right) with an AAV ITR upstream of a promoter driving expression of the gene of interest (GOI) as shown, as well as a non-complementary region therebetween. Because the ligated fragment includes a non-complementary region, the CCE domain will form an extended single-stranded loop or bulged region as shown in the right top portion of the figure, which can accommodate additional sequences, such as an aptamer sequence etc. Non-symmetric digestion can be employed using seamless cloning or other directional cloning techniques to eliminate undesired self-ligation, which may instead lead to the formation of symmetrical ligation production from the first and second plasmids. A cceAAV-BR with multiple ss loop structures can be formed by including additional non-complimentary sequences. The AAV vector here can be produced in any current AAV production system, including herpes virus, vaccinia virus or baculovirus based AAV production systems.
Figure 11:
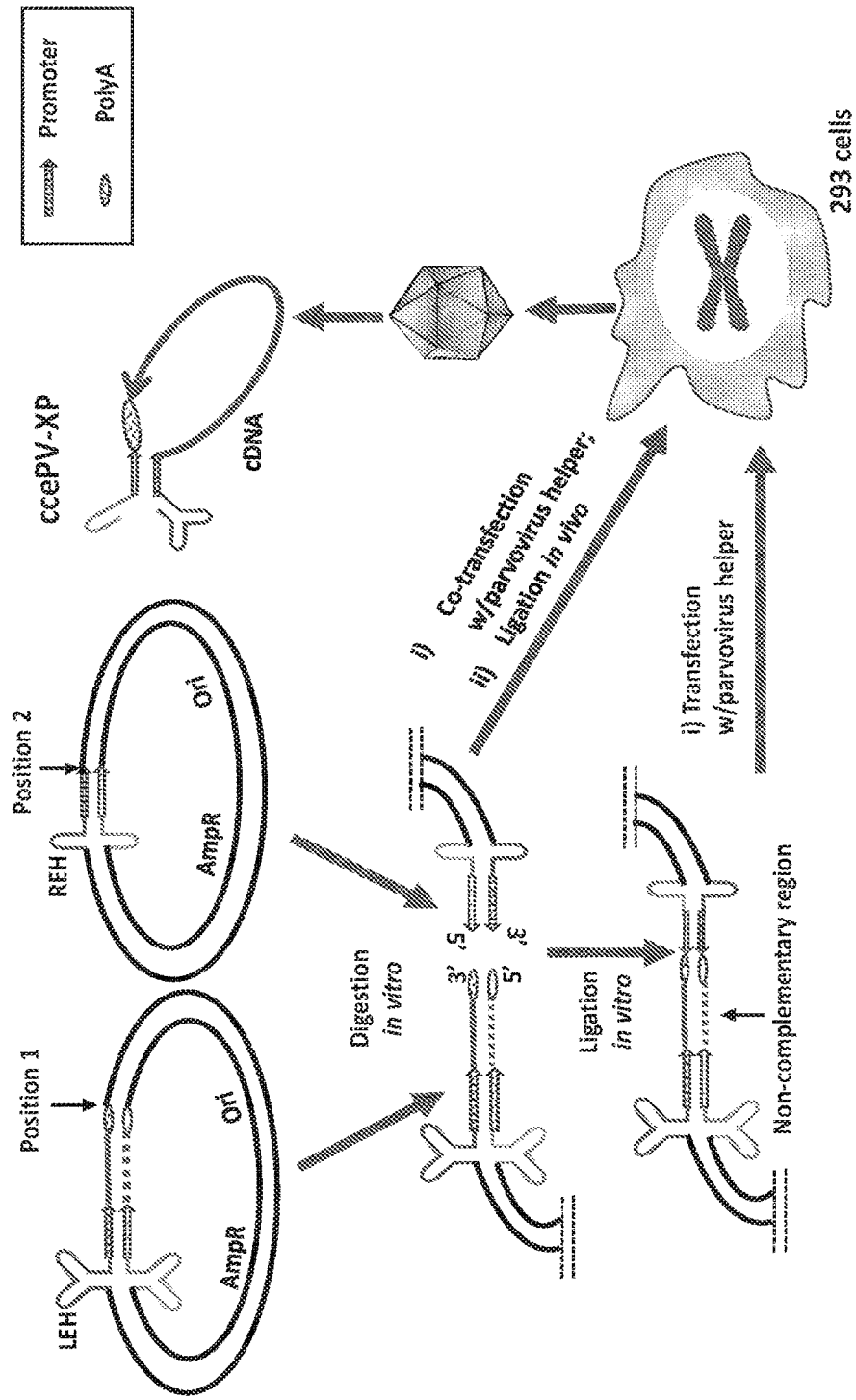
FIG. 11 illustrates a generalized digestion-ligation strategy to produce ccePV-XP vectors for extra packaging capacity. Two different starting plasmids are utilized. A first plasmid (i.e., left-most plasmid shown) containing a PV LEH upstream of an expression cassette is cut at position 1 with an enzyme at the 3' end of the expression cassette containing a cDNA, while a second plasmid (i.e., the right-most plasmid) containing a PV REH upstream of a promoter only (without the cDNA) is cut downstream of the promoter at position 2. The plasmids can be: (1) digested in vitro, ligated in vitro and then co-transfected with parvovirus helper genes; (2) digested in vitro, co-transfected with parvovirus helper genes into PV producer cells and ligation in vivo; or (3) directly co-transfected into host cells for in vivo digestion and in vivo ligation (not shown). The structures formed thereof comprise PV genomes (ccePV-XP, top right), each comprising a non-complementary loop region corresponding to a cDNA, which is packaged into a PV particle. The PV genomes therefore have a configuration of duplex DNA region with promoter activity operatively linked to a single stranded cDNA (loop) region with the coding sequences and polyadenylation signal. Non-symmetric digestion can be employed using seamless cloning or other directional cloning techniques to eliminate undesired self-ligation, which may instead lead to the formation of symmetrical ligation products from the first or second plasmids.
Figure 12:
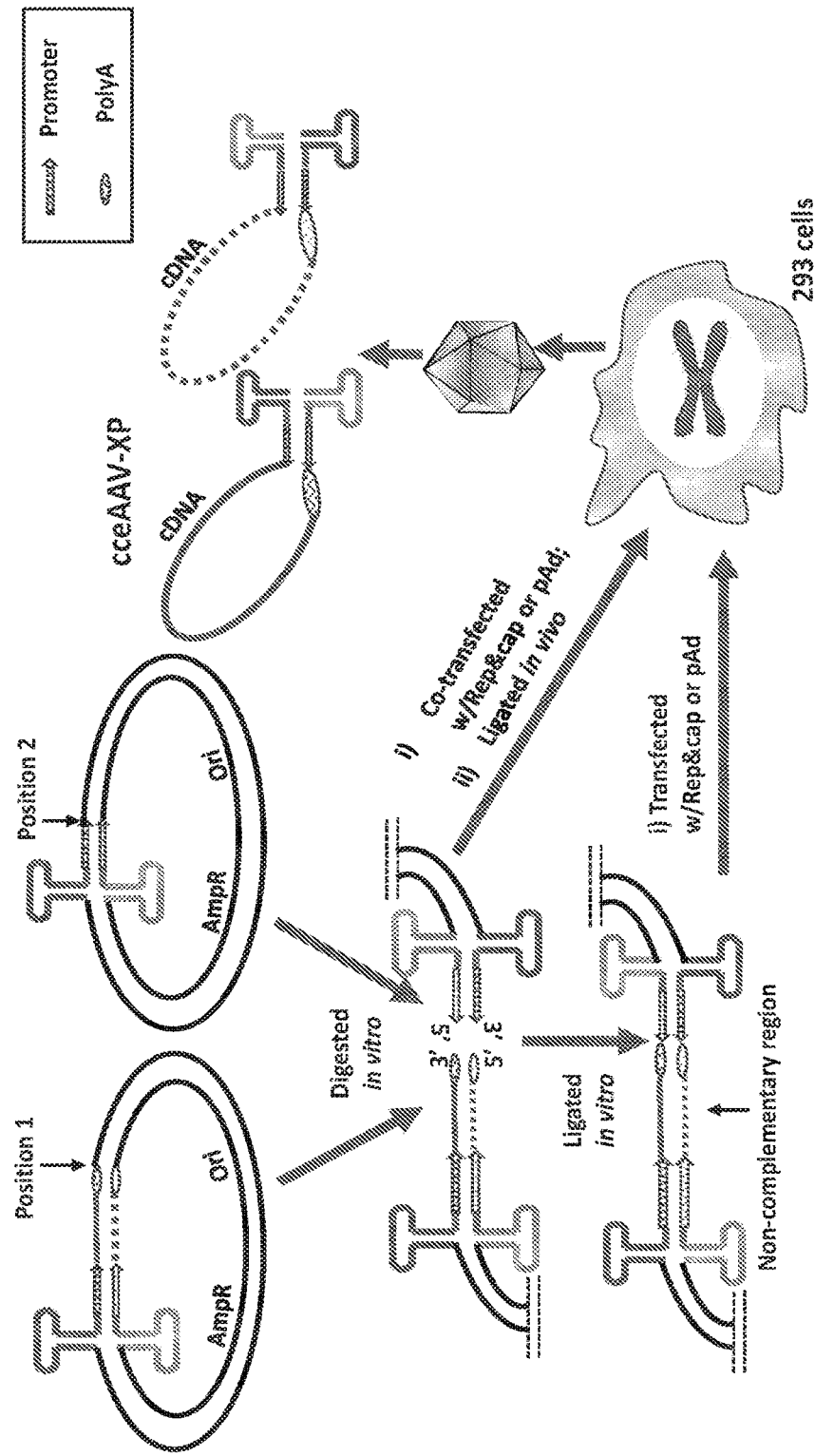
FIG. 12 illustrates an exemplary digestion-ligation strategy to produce a cceAAV-XP vector for extra packaging capacity, based on the general approach outlined in FIG. 11. Two different starting plasmids are utilized. A first plasmid (i.e., left-most plasmid shown) containing a 5'AAV ITR and an expression cassette is cut at position 1 with an enzyme at the 3' end of the expression cassette containing a cDNA, while a second plasmid (i.e., the right-most plasmid) containing a 5'AAV ITR and promoter only (without the cDNA) is cut downstream of the promoter at position 2. The plasmids can be: (1) digested in vitro, ligated in vitro and then co-transfected with AAV helper genes; (2) digested in vitro, co-transfected with parvovirus helper genes into AAV producer cells; or (3) directly co-transfected into host cells for in vivo digestion and in vivo ligation (not shown). The structures formed thereof comprise AAV genomes (cceAAV-XP, top right), each comprising a non-complementary loop region corresponding to a cDNA, both of which are packaged into AAV particles, wherein only one of the genomes (plus strand) is capable of expressing the cDNA. The AAV positive strand genomes therefore have a configuration of duplex DNA region with full promoter activity and the single-stranded cDNA region with the coding sequences and polyadenylation signal. In contrast, the negative strand is able to express the cDNA after the conversion to the duplex format. Non-symmetric digestion can be employed using seamless cloning or other directional cloning techniques to eliminate undesired self-ligation, which may instead lead to the formation of symmetrical ligation products from the first or second plasmids.
Figure 13:
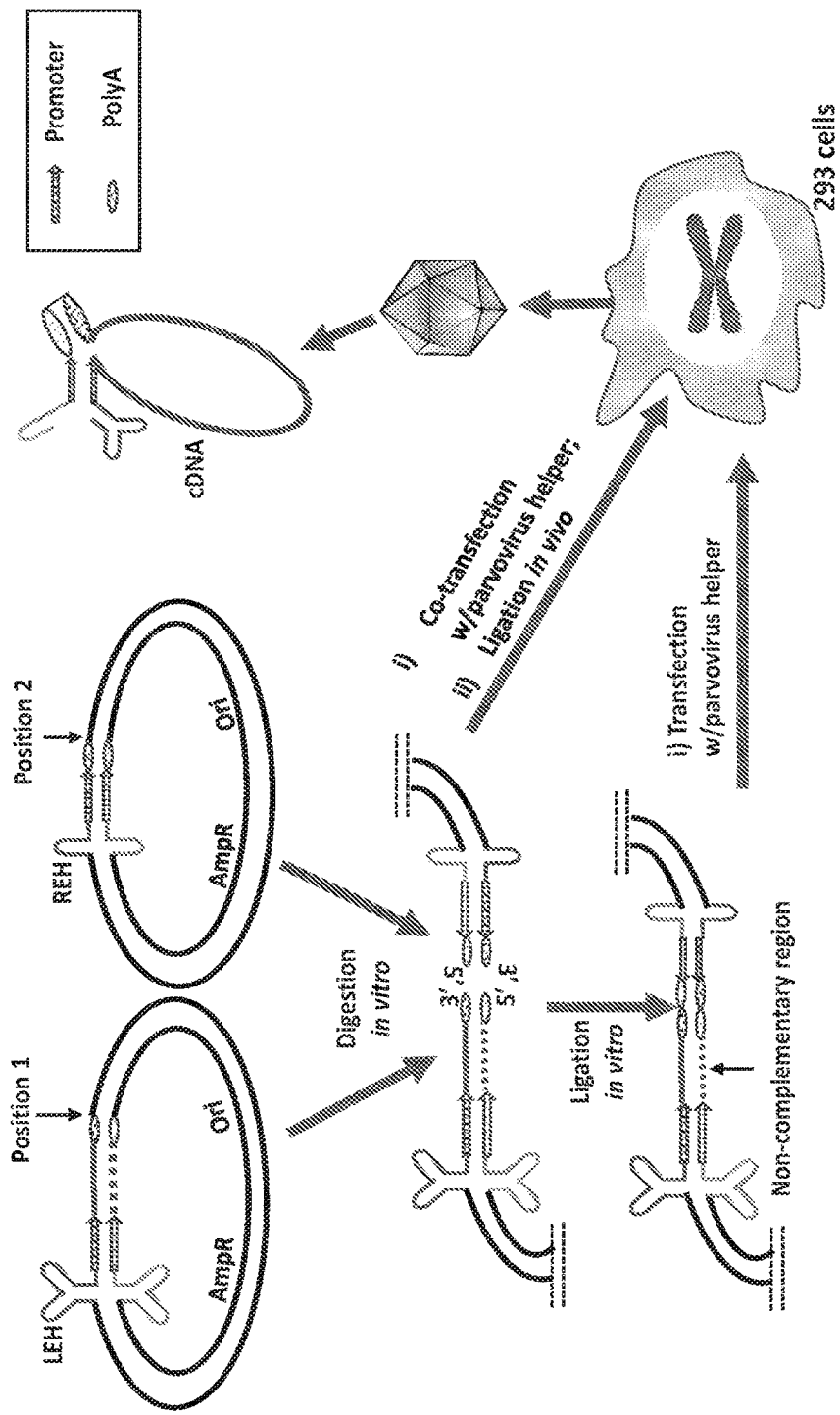
FIG. 13 illustrates another generalized digestion-ligation strategy to produce a ccePV vector for extra packaging capacity. Two different starting plasmids are utilized. A first plasmid (i.e., left-most plasmid shown) containing a PV LEH and an expression cassette comprising a promoter, cDNA and polyadenylation site is cut at position 1 with an enzyme 3' of the polyadenylation site, while a second plasmid (i.e., the right-most plasmid) containing a PV REH and an expression cassette comprising a promoter, cDNA and poly A site cut at position 2 with an enzyme 3' of the poly A site. The plasmids can be: (1) digested in vitro, ligated in vitro, and then co-transfected with parvovirus helper genes into PV producer cells; (2) digested in vitro, and transfected into PV producer cells, where the digested plasmids are ligated in vivo, or (3) the plasmids can be directly transfected into PV producer cells with parvovirus helper genes for in vivo digestion and in vivo ligation (not shown). The resulting PV genomes packaged into PV particles comprise a non-complementary loop region corresponding to the cDNA. The PV genomes therefore have a duplex DNA region with the promoter and poly A site upstream of a single long stranded DNA region encoding the cDNA. Inclusion of the poly A in the second plasmid prevents the production of antisense DNA that could reduce transgene expression when the PV genome undergoes second strand DNA synthesis. Alternatively, or in addition, a DNA insulator sequence may be incorporated to further reduce this outcome and effectively segregate the transcription units from one another. This can be important, since the self-complementary region includes enhancer sequences, which can function in opposite orientation as well. Non-symmetric digestion can be employed using seamless cloning or other directional cloning techniques to eliminate undesired self-ligation, which may instead lead to the formation of symmetrical ligation products from the first or second plasmids.

In one embodiment, a single ccePV or cceAAV template molecule is digested and ligated extracellularly prior to transfection into PV producer cells as illustrated in FIGS. 5-6. The digested fragment(s) can be self-ligated in vitro with a DNA ligase. This can generate DNA template molecules for producing a ccePV or cceAV with zero loop (ZL) sequences (see e.g., FIGS. 5-6)

DNA templates for PV replication contain a PV or AAV ITR, a DS domain, and one or more endonuclease cleavage sites cut by one or more nucleases. The cleavage site(s) may be cut with a restriction enzyme, meganuclease, transcription activator-like effector nuclease (TALEN), zinc finger nucleases (ZFN), guide RNA-based CRISPR/Cas9 nuclease, other nuclease, or combination thereof. The fragments may be then ligated with a DNA ligase. The resulting fragment may be used for parvovirus production with or without amplification. The amplification methods may be in vitro using PCR and rolling cycle phi29 type polymerases.

Transfection of the self-ligated fragment into a PV producer cell compatible for PV or AAV vector particle production results in the formation of ccePVs or cceAAVs in accordance with the inventive subject matter described herein. Other cis or trans functions that are required for parvovirus/AAV vector production are supplied by transfection, viral vector delivery or stable integration of helper genes into host cells.

2. In Vitro Digestion and In Vitro Ligation of Two or More DNA Template Molecules In some embodiments, the method for producing a ccePV or cceAAV comprises the use of two or more DNA template molecules, including at least one DNA template molecule containing at least one AAV ITR and one DS domain are cleaved with a restriction enzyme, meganuclease, transcription activator-like effector nuclease (TALEN), zinc finger nuclease (ZFN), guide RNA-based CRISPR/Cas9 nuclease, other nuclease or combination thereof as depicted in FIGS. 8-18. The use of two or more template molecules allows for the production of PV or AAV particles with genomes comprising one or more extended bulged, looped or branched structures in the CCE domain.

To generate ccePVs or cceAAVs with branches or loops, two or more starting plasmids are typically utilized. This can be a combination of plasmids, viral vectors or synthesized DNA fragments. The designated sites in two starting plasmids can be identical or completely different. To avoid self-ligation which would lead the contaminated cce vectors, non-symmetrical enzyme digestion or clustered regularly interspaced short palindromic repeats (CRISPR)/Cas9 digestion will be utilized. The asymmetric nature and recognition sequence length can efficiently block undesired self-ligation.

As there are two fragments from the plasmids used for ligation, it is essential to use common molecular biology techniques to create DNA ends that will not undergo self-ligation (an asymmetric digestion with restriction enzyme and CRISPR/Cas9 enzyme will achieve this goal). The fragments may be ligated with a DNA ligase. The fragments used for ligation are different. The resulting fragment may be used for parvovirus production with or without amplification. The amplification methods may be in vitro using PCR and rolling cycle phi29 type polymerases.

3. In Vitro Digestion of a Single DNA Template without In Vitro Ligation

In another embodiment, a single DNA template, such as a plasmid, is digested in vitro and the digested fragment is transfected with one or more parvovirus helper genes, such as Rep, Cap and pAd (mini adenovirus providing additional helper genes) into a host cell suitable for AAV production. The host cell may be transiently or stably transformed with one or more these helper genes. The transfected fragments are then ligated intracellularly in vivo using the host's cellular ligation enzymes.

The plasmid carrying at least one AAV ITR and one DS domain is cleaved by a restriction enzyme, meganuclease, transcription activator-like effector nuclease (TALEN), zinc finger nuclease (ZFN), guide RNA based CRISPR/Cas9 nuclease, other nuclease, or combination thereof. The resulting fragments will be transfected into host cells for parvovirus production. The host cellular ligase will facilitate the ligation to generate the vector DNA sequence for vector production.

4. In Vitro Digestion of Two or More DNA Templates without In Vitro Ligation

Two plasmids carrying at least one AAV ITR and one DS domain are cleaved with a restriction enzyme, or other meganuclease, Transcription activator-like effector nucleases (TALEN), Zinc finger nuclease, or guide RNA based CRISPR/Cas9 nucleases. As there are two fragments from the plasmids used for ligation, it is essential to use common molecular biology techniques to create DNA ends that will not undergo self-ligation (an asymmetric digestion with restriction enzyme and CRISPR/Cas9 enzyme will achieve this goal). The resulting fragments will be transfected into host cells for parvovirus production. The host cellular ligase will facilitate the ligation to generate the vector DNA sequence for vector production.

5. In Vivo Digestion and In Vivo Ligation of a Single DNA Template

In yet another embodiment, a single DNA template molecule, such the template depicted in FIGS. 5-6, is transfected into host cells followed by in vivo digestion and in vivo ligation of the DNA template therein. The enzymes that cut the designated sites are co-transfected into host cells. Alternatively, the enzyme can be delivered by viral vector, such as vaccinia, herpes virus vector, adenovirus vector or other common viral and non-viral vectors. The enzyme may be delivered to host cells by physical methods or integrated in host cells. When the plasmid is ligated in vivo, it is common to observe some insertions or deletions in the site of digestions. Generally, the small deletions or insertions will not affect the performance of the vectors.

Figure 19:
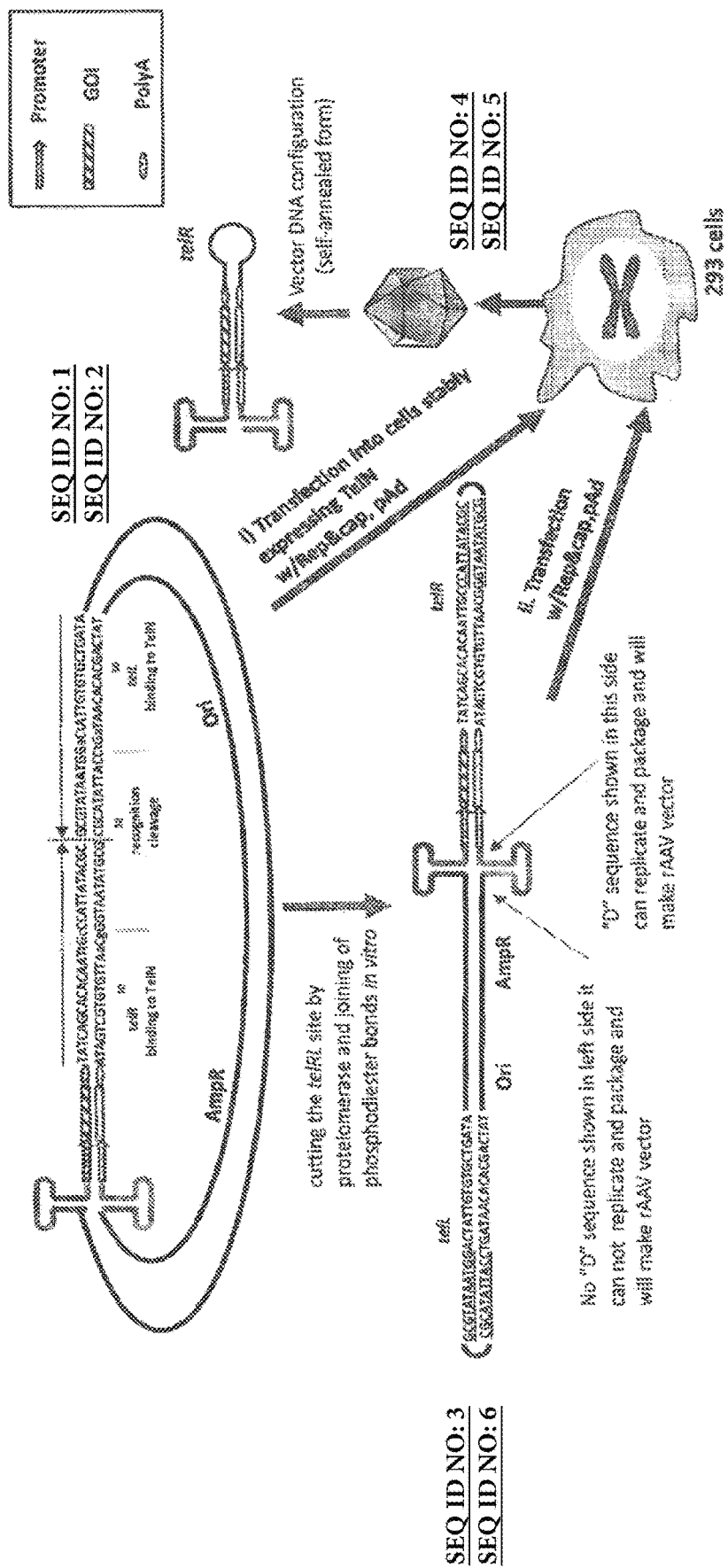
FIG. 19 illustrates an exemplary method for producing a cceAAV vector using a single plasmid operative with the TelN/telRL system. The plasmid contains an AAV ITR forming stem-loop structures on both strands, an expression cassette comprising a nucleic acid of interest (NAOI or GOI), and a downstream poly A site, which is followed by a telRL site for the TelN enzyme. Cleavage and ligation of the plasmid by the TelN enzyme results in the formation of an intermediate double stranded closed end molecule, which is the template molecule for packaging the cceAAV vector depicted in FIG. 19 when transfected into AAV producing cells. Because the AAV packaging signal comprising the "D" sequence is configured 3' of the ITR in the intermediate, and not 5' of the ITR, only the right side of the intermediate will be compatible for replication and encapsidation so as to form the cceAAV vector depicted in the upper right of the figure. The TelN enzyme can be delivered using a viral vector, such as adenovirus or expressed from AAV producing cells to avoid the need to do the TelN reaction in vitro. This design can be further extended production of a ccePV vector comprising identical ITRs in the 5'end or 3' ends. The scAAV with shDNA can be produced using this approach as well when shDNA sequences are matching the protelomerase recognition or compatible sites.
Figure 20:
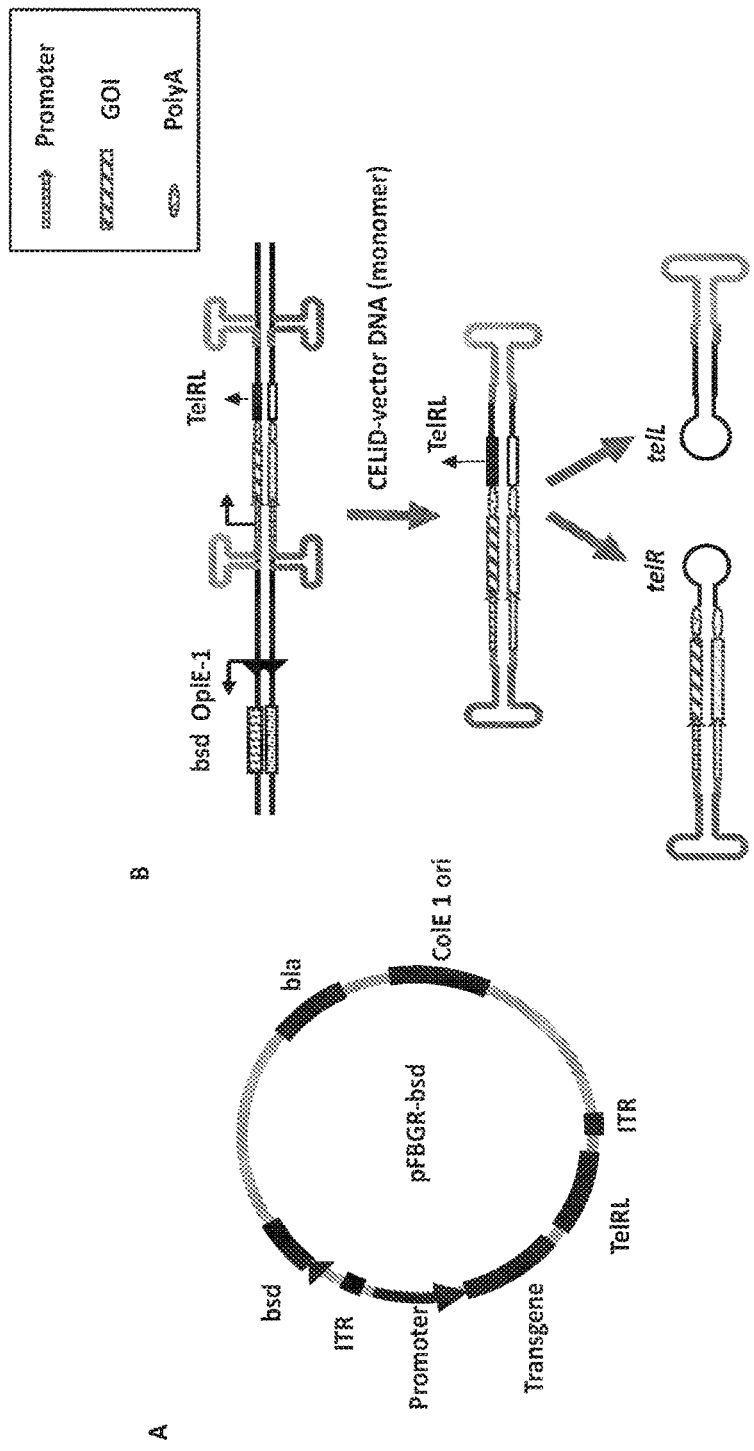
FIG. 20 illustrates an exemplary method for producing cceAAV vectors using the CELiD-vector DNA. The starting CELiD-vector DNA as published can carry a designed TelRL or resT site. Upon incubation with a TelN or resT enzyme, two linear plasmids are formed that can be used for producing cceAAV when transfected to the AAV producing cells. The no end substrate with only one ITR can be used directly as pharmaceutical products, such as DNA vaccine. This strategy can also be extended to produce the ccePV when the ITRs are identical. The process of using baculovirus for producing the linear molecules using pFBGR-bsd or CELiD vector are described in the literature.
Figure 21:
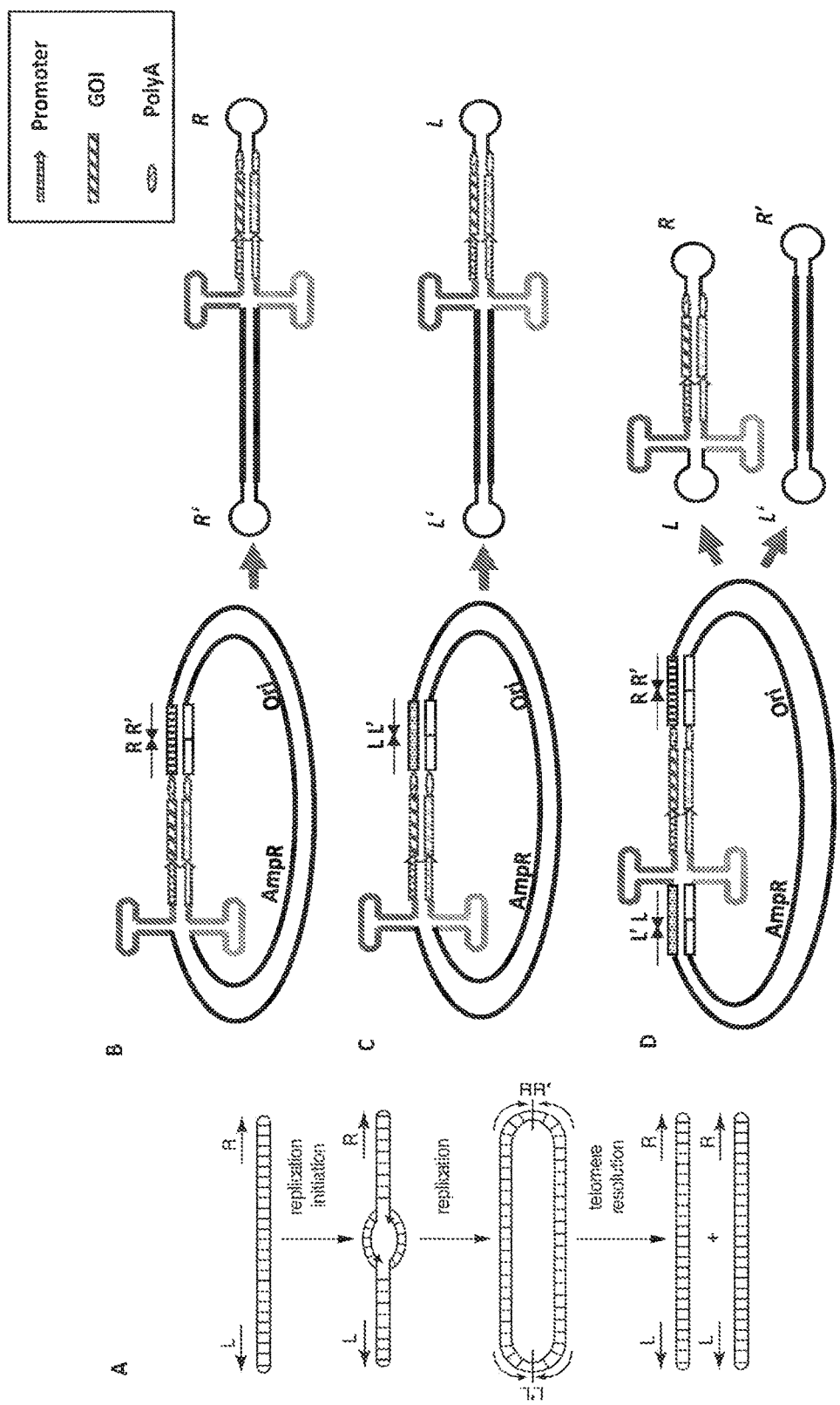
FIG. 21 illustrates an exemplary method for producing cceAAV vector template molecules using the telomere resolvase enzyme, ResT. The starting plasmid includes an AAV ITR and a double-stranded domain (DS domain) comprising an expression cassette containing LL or RR cleavage sites cut by the enzyme, ResT. This leads to the formation of a linear plasmid that can be used for producing cceAAV when transfected to the AAV producing cells. The ResT can be delivered using a viral vector, such as an adenovirus or expressed from AAV producing cells. The left panel shows the replication of a linear molecule results in the formation of dimer junctions or replicated telomeres (L'L, RR') that are processed by telomere resolution, a unique type of DNA breakage and reunion reaction. Telomere resolution results in the formation of hairpin telomeres at the ends of the linear DNA molecule and separates the dimer replication intermediate into monomeric products of DNA replication. The B. burgdorferi enzyme, ResT (Resolvase of Telomeres) is an example.
Figure 22:
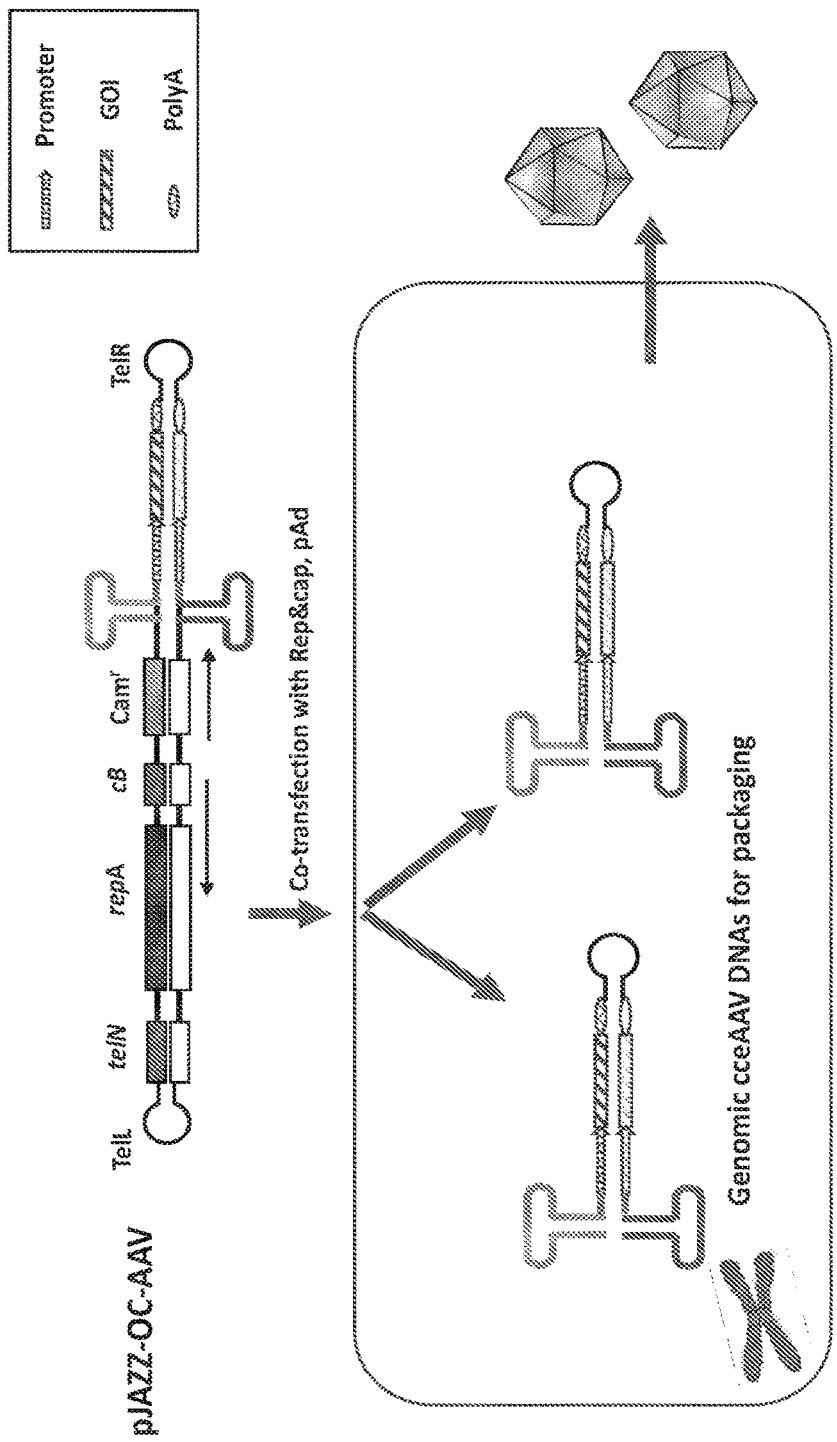
FIG. 22 illustrates an exemplary method for producing cceAAV vector template molecules using a linear plasmid containing an AAV ITR and a DS domain cloned in close proximity to TelR and TelL binding sequences. This linear plasmid can be produced in mass in the bacteria or in vitro by Loop mediated isothermal amplification (LAMP) method. The resulting linear plasmids are compatible for production of cceAAV vector in AAV producer host cells.

In a particular embodiment, a method for producing a ccePV or cceAAV with a symmetrical genome comprises the use of a telomere resolvase, such as ResT, delivered into host cells with cce DNA molecules carrying a parvovirus ITR and a DS domain, as illustrated in FIG. 19. Use of a telomere resolvase can promote formation of template molecules for cceAAV or ccePV production, which can be transfected into a parvovirus or AAV producer cell line so that ccePVs and cceAAVs can be produced. Alternatively the DNA molecules with a parvovirus ITR, a DS domain, and a telomere resolvase site can be transfected to host cells, or delivered to host cells by a viral vector or stably integrated into host cells so that telomere resolvase can be expressed in vivo. The telomere resolvase will then work on the starting DNA molecule to generate molecules for ccePV or cceAAV production.

The plasmid or viral vectors carrying at least one AAV ITR and one DS domain are transfected or infected into host cells. The restriction enzymes, or other meganuclease, Transcription activator-like effector nucleases (TALEN), Zinc finger nucleases, or guide RNA based CRISPR/Cas9 nucleases are co-transfected to the host cell, or carried by viral vectors or integrated into host cells will be used to digest the plasmid at the desired sites. The resulting fragments will be ligated by the host cellular ligase to generate the vector DNA sequence for vector production.

6. In Vivo Ligation or Two or More DNA Template Molecules

The two plasmids or viral vectors carrying at least one AAV ITR and one DS domain are transfected or infected into host cells. The restriction enzymes, or other meganuclease, transcription activator-like effector nucleases (TALENs), zinc finger nucleases (ZFNs), or guide RNA based CRISPR/Cas9 nucleases can be co-transfected into host cells, delivered by viral vectors or stably integrated into host cells where they can digest the plasmid at the desired sites. As there are two fragments from the plasmids used for ligation, it is essential to use common molecular biology techniques to create DNA ends that will not undergo self-ligation (an asymmetric digestion with restriction enzyme and CRISPR/Cas9 enzyme will achieve this goal). The resulting fragments will be ligated by the host cellular ligase to generate the vector DNA sequence for vector production.

7. In Vivo Digestion and In Vivo Ligation of One or More Integrated DNA Template Molecules In this method, two DNA fragments are integrated to the host chromosome at proximity. A CRISPR/Cas9 mediated digestion will remove the space between them and allow the production of the required vectors.

In one embodiment, the parvovirus ITR or AAV ITR along with a DS domain and designated digestion site are delivered by a viral vector, such as adenovirus vector, herpes viral vector etc. The enzymes that digested the template molecules can be transfected to cells, delivered by a viral vector or stably integrated into host cells. Upon provided other essential elements for parvovirus or AAV vectors, ccePV or cceAAV can then be produced.

The enzymes used for digesting the designated sites can be common restriction nucleases (ref. The Restriction Enzyme Database (REBASE), zinc finger nucleases, transcription activator-like (TAL) effector nucleases (TALEN), meganucleases and hybrid meganucleases (A large bank containing several tens of thousands of protein units has been created. These units can be combined to obtain chimeric meganucleases that recognize the target site), the clustered regularly interspaced short palindromic repeats (CRISPR)/Cas9) system.

In some embodiments, one or more ccePV template molecules are introduced into the host cell and integrated into the host cell chromosome. In some embodiments, the 5' ITR, the first strand of the DS region and designated digestion site is integrated in one site of host cell chromosome. Downstream, the designated site, the second strand of the DS domain and the 3' ITR is integrated in the same chromosome. Digestion by a suitable nuclease enzyme, such as the guide RNA-based CRISPR/Cas9 system will remove the spacer sequences between the two regions, which will be compatible for rescue and production of the ccePV.

Methods for Making scAAVs with mTR and shDNA Sequences

The above described methods can also be used to produce scAAVs with mTRs or shDNAs. The conventional method for producing a scAAV relies on inclusion of a mTR or shDNA to provide a mechanism in which a complementary strand can be generated during the rAAV genome rescue step in vivo. This conversion efficiency is relatively inefficient and often leads to the formation of byproducts that reduce the vector production and results in the production of defective interfering particles or vectors with short genomes.

Figure 23:
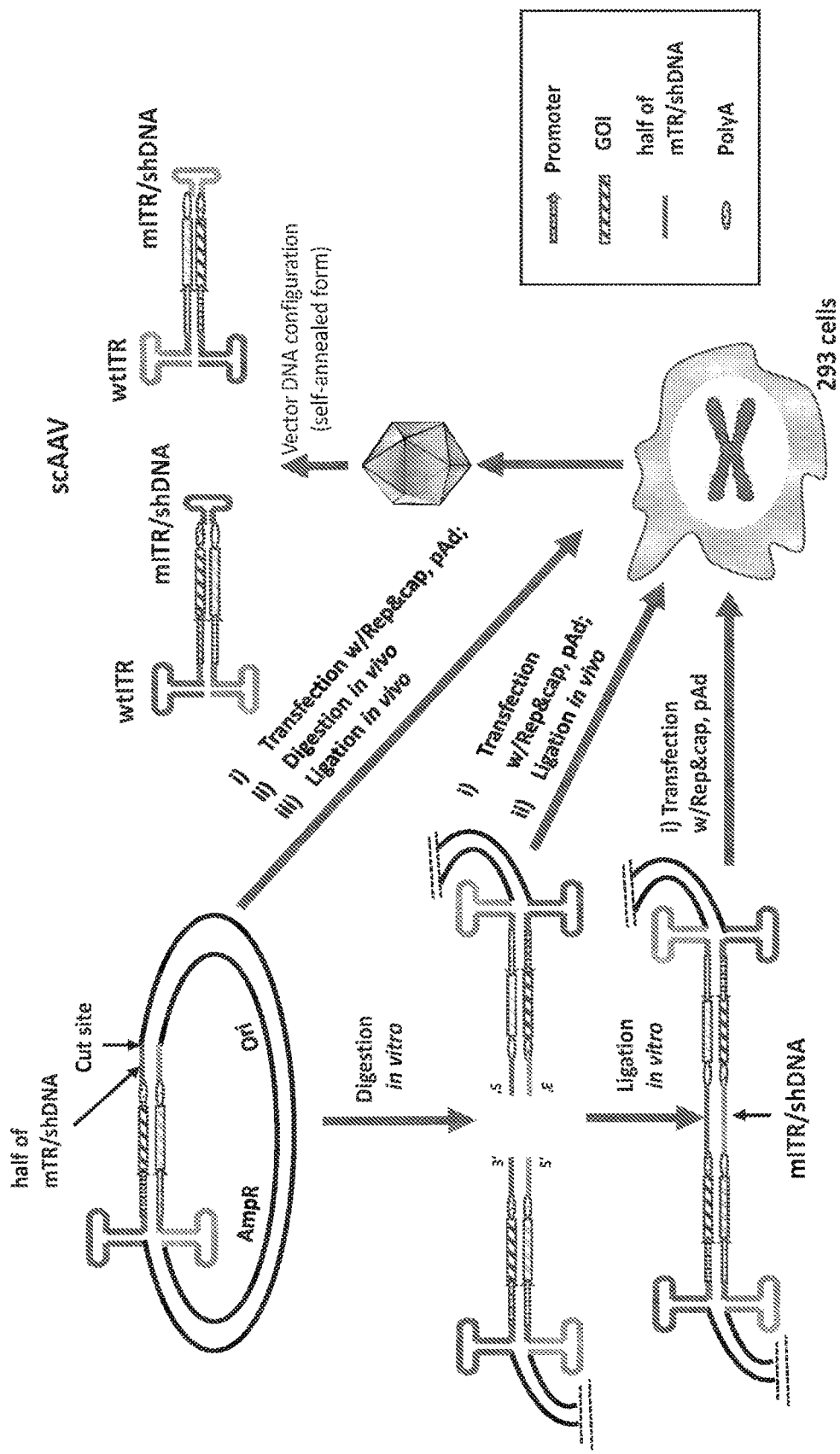
FIG. 23 illustrates an exemplary ligation strategy to produce a scAAV with a mTR or shDNA close end vector. First, a starting plasmid with an AAV ITR and at least half of mTR and shDNA is digested so the fragment will have half of the mTR or shDNA sequences. The self-ligation will generate a molecule templated for scAAV with mTR or shDNA. The resulting fragment can be subject to three different pathways for producing the corresponding scAAV particles. The starting plasmid can be: (1) digested (i.e., linearized) in vitro, ligated in vitro and then transfected in AAV producing cells (e.g., 293, or any other cells with complementary genes supplied) transfected with Rep, Cap and pAd (with additional adenovirus helper genes not supplied in the producing cell line; (2) digested (i.e., linearized)

The above methods for producing cceAAV or ccePV can also be used to produce scAAV vector using the digestion/ligation strategies outlined herein or using the telomere resolvase approach as described. As described above, digestion/ligation approach is advantageous over the conventional scAAV production methodologies utilizing template molecules for scAAV production involving an mTR or shDNA, since the presently described methods already have two fully functional ITRs. For example, the present application further provides an improved method for producing scAAVs with an mTR or shDNA by creating a molecules with the desired closed end for transfection directly. This can be achieved by direct ligation of a fragment with a closed end. Alternatively, the closed end can be produced using a telomere resolvase or protelomerase. Such molecules provide more efficient substrates for producing a scAAV vector with a mTR or shDNA (see FIGS. 23-25 and their accompanying figure legends).

Methods of Using the ccePVs and cceAAVs of the Present Application

Another aspect of the present application relates to methods of treating a therapeutic condition with the ccePV or cceAAV of the present application comprising the steps of administering to a subject in need of such treatment an effective amount of the ccePV of the present application, wherein the ccePV expresses one or more products having a therapeutic benefit for treatment of the therapeutic condition.

Other Embodiments

In some embodiments, the present application relates to a vector having a DNA genome that comprises, in the 5' to 3' direction in single stranded form: (1) a parvovirus terminal repeat at the 5' end, (2) a first regulatory region comprising (a) a promoter region, or (b) a poly A or poly T sequence, or both (a) and (b), (3) a first heterologous nucleotide sequence, (4) a covalently closed end (CCE) domain, (5) a second heterologous nucleotide sequence, (6) a first regulatory region comprising (a) a promoter region, or (b) a poly A or poly T sequence, or both (a) and (b), and (7) a parvovirus terminal repeat at the 3' end; wherein the first regulatory sequence is complementary to the second heterologous sequence and forms a double-stranded region (DS-domain) in the vector genome, wherein the CCE domain is (a) a single covalent bond connecting the first heterologous nucleotide sequence and the second nucleotide sequence, or (b) a single stranded DNA region, and wherein the vector DNA genome is capable of producing a double-stranded (DS)-RNA molecule from the DS-domain of the vector genome.

In some embodiments, the DS-domain is not contiguous with a self-annealed stem portion comprising more than 20 contiguous nucleotide base pairs from a mutant inverted terminal repeat (mTR) sequence or a short hairpin RNA (shRNA) coding sequence.

In some embodiments, the CCE domain does not contain an mTR sequence, or a shRNA coding sequence, or both.

The following paragraphs enumerated consecutively from 1 through 47 provide for various aspects and/or embodiments of the present invention.

1. A duplexed parvovirus particle comprising: a parvovirus capsid; and a vector genome comprising in the 5' to 3' direction: (a) a parvovirus terminal repeat at the 5' end; (b) a parvovirus terminal repeat at the 3' end; (c) a double stranded (DS) DNA domain between the terminal repeats in (a) and (b), the DS-DNA domain comprising a self-complementary first heterologous nucleotide sequence annealed to second heterologous nucleotide sequence; and (d) a single stranded covalently closed end (SS-CCE) domain between the first heterologous nucleotide sequence and the second heterologous nucleotide sequence, the SS-CCE domain comprising a looped structure; wherein the DS domain is not contiguous with a self-annealed stem portion comprising more than 20 contiguous nucleotide base pairs from a mutant inverted terminal repeat (mTR) sequence or a short hairpin DNA (shDNA) sequence, and wherein the vector genome is capable of being replicated to form the duplexed parvovirus particle when introduced into a host cell expressing helper functions sufficient for producing the duplexed parvovirus particle.

2. The parvovirus particle of paragraph 1, wherein the SS-CCE domain does not comprise more than 20 contiguous nucleotides from a mutant inverted terminal repeat (mTR) or a short hairpin DNA (shDNA) sequence.

3. The parvovirus particle of paragraph 1 or 2, wherein the SS-CCE domain comprises between 3 and 4,000 nucleotides, between 50 and 4,000 nucleotides, between 1,000 and 4,000 nucleotides, between 3 and 2,000 nucleotides, between 50 and 2,000 nucleotides, between 250 and 2,000 nucleotides, or between 500 and 2,000 nucleotides.

4. The parvovirus particle of any one of paragraphs 1 to 3, wherein the SS-CCE domain comprises a sequence encoding a protein or RNA.

5. The parvovirus particle of paragraph 4, wherein the sequence encoding the protein or RNA further comprises a downstream polyadenylation signal operatively linked thereto.

6. The parvovirus particle of any one of paragraphs 1 to 5, the first heterologous nucleotide sequence has more than 95%, more than 99%, or 100% inverse complementarity to the second heterologous nucleotide sequence.

7. The parvovirus particle of any one of paragraphs 1 to 6, wherein the DS domain comprises a promoter operatively linked to nucleic acid encoding a protein or RNA.

8. The parvovirus particle of paragraph 7, wherein the DS domain further comprises a polyadenylation signal operatively linked to the nucleic acid encoding the protein or RNA.

9. The parvovirus particle of any one of paragraphs 1 to 5, wherein the DS domain is interrupted by a looped or branched single stranded DNA.

10. The parvovirus particle of paragraph 9, wherein the looped or branched single stranded DNA comprises nucleotide encoding a protein or RNA.

11. The parvovirus particle of paragraph 10, wherein the sequence encoding the protein or RNA further comprises a downstream polyadenylation signal operatively linked thereto.

12. The parvovirus particle of any one of paragraphs 1 to 11, wherein the parvovirus terminal repeat in (a) comprises a left-end hairpin (LEH) and the terminal repeat in (b) comprises a right-end hairpin (REH).

13. The parvovirus particle of any one of paragraphs 1 to 11, wherein the parvovirus terminal repeat comprises an adeno-associated virus (AAV) inverted terminal repeat (ITR).

14. A method for making the parvovirus particle of paragraph 1, comprising: (a) providing a plasmid comprising a fragment comprising in a 5' to 3' direction: (i) a parvovirus terminal repeat comprising a left-end hairpin (LEH) or an inverted terminal repeat (ITR); (ii) a promoter operatively linked to a nucleic acid encoding a protein or RNA; and (iii) a nuclease cut site in the plasmid; (b) providing a host cell comprising one or more helper genes sufficient for replicating a nucleic acid comprising parvovirus terminal repeats flanking a nucleic acid of interest; (c) digesting the plasmid with a nuclease enzyme specific for the nuclease cut site under conditions sufficient for linearizing the plasmid, wherein the plasmid is digested in vitro or is digested in the host cell; (d) ligating the plasmid to itself with a DNA ligase, wherein the plasmid is ligated in vitro or is ligated in the host cell; (e) culturing the host cell comprising the plasmid treated according to steps (c) and (d) under conditions suitable for producing parvovirus particles following completion of step (d); and (f) recovering the parvovirus particles produced in step (f).

15. The method of paragraph 14, wherein the fragment comprises a parvovirus LEH.

16. The method of paragraph 14, wherein the fragment comprises an AAV ITR.

17. The method of any one of paragraphs 14 to 16, wherein the plasmid further comprises a subfragment downstream of the fragment, wherein the subfragment comprises in a 5' to 3' direction: (i) a telR binding site; (b) a TelN nuclease recognition cleavage site; and (iii) a tell binding site, and wherein the plasmid is digested and self-ligated with TelN enzyme; and wherein the plasmid is digested and self-ligated in vitro or is digested and self-ligated in the host cell.

18. A method for making the parvovirus particle of paragraph 1, comprising: (a) providing a first plasmid comprising a first fragment comprising in a 5' to 3' direction: (i) a parvovirus terminal repeat comprising a left-end hairpin (LEH) or an inverted terminal repeat (ITR); (ii) a promoter operatively linked to nucleic acid encoding a protein or RNA; and (iii) a first nuclease cut site in the first plasmid; (b) providing a second plasmid comprising a second fragment comprising in a 5' to 3' direction: (i) a parvoviral terminal repeat comprising a right-end hairpin (REH) or an ITR; (ii) a promoter; (iii) a nucleic acid encoding a protein or RNA; and (iv) a second nuclease cut site in the second plasmid, wherein the second fragment is identical to the first fragment with the exception that the second fragment further comprises one or more contiguous nucleotide base pairs absent in the first fragment; (c) providing a host cell comprising one or more helper genes sufficient for replicating a nucleic acid comprising parvovirus terminal repeats flanking a nucleic acid of interest; (d) digesting the first plasmid with a nuclease enzyme specific for the nuclease cut site in (a)(iii) under conditions sufficient for linearizing the first plasmid, wherein the first plasmid is digested in vitro or is digested in the host cell; (e) digesting the second plasmid with a nuclease enzyme specific for the nuclease cut site in (b)(iv) under conditions sufficient for linearizing the second plasmid, wherein the second plasmid is digested in vitro or is digested in the host cell; (f) ligating the first and second plasmids digested in steps (d) and (e) with a DNA ligase, wherein the digested first and second plasmids are ligated in vitro or are ligated in the host cell; (g) culturing the host cell comprising the first and second plasmids treated according to steps (d) to (f) under conditions suitable for producing parvovirus particles following completion of step (f); and (h) recovering the parvovirus particles produced in step (g).

19. The method of paragraph 18, wherein the first fragment comprises a parvovirus LEH and the second fragment comprises a parvovirus REH.

20. The method of paragraph 18, wherein each of the first and second fragments comprises an AAV ITR.

21. The method of any one of paragraphs 18 to 20, wherein the second fragment comprises a subfragment between (b)(iii) and (b)(iv).

22. The method of paragraph 21, wherein the subfragment is between 3 to 4,000 base pairs in length, between 50 to 4,000 base pairs in length, between 1,000 to 4,000 base pairs in length, between 3 to 2,000 base pairs in length, between 50 to 2,000 base pairs in length, between 250 to 2,000 base pairs in length, or between 500 to 2,000 base pairs in length.

23. The method of any one of paragraphs 18 to 20, wherein the second fragment comprises a subfragment between (b)(ii) and (b)(iii).

24. The method of paragraph 23, wherein the subfragment is between 3 to 4,000 base pairs in length, between 50 to 4,000 base pairs in length, between 1,000 to 4,000 base pairs in length, between 3 to 2,000 base pairs in length, between 50 to 2,000 base pairs in length, between 250 to 2,000 base pairs in length, or between 500 to 2,000 base pairs in length.

25. A method for making the parvovirus particle of paragraph 1, comprising: (a) providing a first plasmid comprising a first fragment comprising in a 5' to 3' direction: (i) a parvovirus terminal repeat comprising a left-end hairpin (LEH) or an inverted terminal repeat (ITR); (ii) a promoter; (iii) a nucleic acid encoding a protein or RNA; (iv) a polyadenylation signal; and (v) a first nuclease cut site in the first plasmid; (b) providing a second plasmid comprising a second fragment comprising in a 5' to 3' direction: (i) a parvoviral terminal repeat comprising a right-end hairpin (REH) or an ITR; (ii) a promoter; and (iii) a second nuclease cut site in the second plasmid; (c) providing a host cell comprising one or more helper genes sufficient for replicating a nucleic acid comprising parvovirus terminal repeats flanking a nucleic acid of interest; (d) digesting the first plasmid with a nuclease enzyme specific for the nuclease cut site in (a)(v) under conditions sufficient for linearizing the first plasmid, wherein the first plasmid is digested in vitro or is digested in the host cell; (e) digesting the second plasmid with a nuclease enzyme specific for the nuclease cut site in (b)(iii) under conditions sufficient for linearizing the second plasmid, wherein the second plasmid is digested in vitro or is digested in the host cell; (f) ligating the first and second plasmids digested in steps (d) and (e) with a DNA ligase, wherein the digested first and second plasmids are ligated in vitro or are ligated in the host cell; (g) culturing the host cell comprising the first and second plasmids treated according to steps (d) to (f) under conditions suitable for producing parvovirus particles following completion of step (f); and (h) recovering the parvovirus particles produced in step (g).

26. The method of paragraph 25, wherein the first fragment comprises a parvovirus LEH and the second fragment comprises a parvovirus REH.

27. The method of paragraph 25, wherein each of the first and second fragments comprises an AAV ITR.

28. The method of any one of paragraphs 25 to 27, wherein the nucleic acid encoding the protein or RNA in (a)(iii) is between 3 to 4,000 base pairs in length, between 50 to 4,000 base pairs in length, between 1,000 to 4,000 base pairs in length, between 3 to 2,000 base pairs in length, between 50 to 2,000 base pairs in length, between 250 to 2,000 base pairs in length, or between 500 to 2,000 base pairs in length.

29. A method for making the parvovirus particle of paragraph 1, comprising: (a) providing a first plasmid comprising a first fragment comprising in a 5' to 3' direction: (i) a parvovirus terminal repeat comprising a left-end hairpin (LEH) or an inverted terminal repeat (ITR); (ii) a promoter; (iii) a first polyadenylation signal; (iv) an inversely complementary nucleic acid encoding a first protein or first RNA, each of the first protein and first RNA having a right to left polarity; (v) a nucleic acid encoding a second protein or second RNA, each of the second protein and second RNA having a left to right polarity; (vi) a second polyadenylation signal; and (vii) a first nuclease cut site in the first plasmid; (b) providing a second plasmid comprising a second fragment comprising in a 5' to 3' direction: (i) a parvoviral terminal repeat comprising a right-end hairpin (REH) or an ITR; (ii) the promoter in (a)(ii); (iii) a nucleic acid encoding the second protein or second RNA, each of the second protein and second RNA having a left to right polarity; (iv) a polyadenylation signal; and (v) a second nuclease cut site is in the second plasmid; (c) providing a host cell comprising one or more helper genes sufficient for replicating a nucleic acid comprising parvovirus terminal repeats flanking a nucleic acid of interest; (d) digesting the first plasmid with a nuclease enzyme specific for the nuclease cut site in (a)(vii) under conditions sufficient for linearizing the first plasmid, wherein the first plasmid is digested in vitro or is digested in the host cell; (e) digesting the second plasmid with a nuclease enzyme specific for the nuclease cut site in (b)(v) under conditions sufficient for linearizing the second plasmid, wherein the second plasmid is digested in vitro or is digested in the host cell; (f) ligating the first and second plasmids digested in steps (d) and (e) with a DNA ligase, wherein the digested first and second plasmids are ligated in vitro or are ligated in the host cell; (g) culturing the host cell comprising the first and second plasmids treated according to steps (d) to (f) under conditions suitable for producing parvovirus particles following completion of step (f); and (h) recovering the parvovirus particles produced in step (g).

30. The method of paragraph 29, wherein the first fragment comprises a parvovirus LEH and the second fragment comprises a parvovirus REH.

31. The method of paragraph 29, wherein each of the first and second fragments comprises an AAV ITR.

32. The method of any one of paragraphs 29 to 31, wherein the nucleic acid encoding the protein or RNA in (a)(iv), (a)(v), or both is between 3 to 4,000 base pairs in length, between 50 to 4,000 base pairs in length, between 1,000 to 4,000 base pairs in length, between 3 to 2,000 base pairs in length, between 50 to 2,000 base pairs in length, between 250 to 2,000 base pairs in length, or between 500 to 2,000 base pairs in length.

33. The method of any one of paragraphs 29 to 31, wherein the nucleic acid encoding the protein or RNA in (b)(iii) is between 3 to 4,000 base pairs in length, between 50 to 4,000 base pairs in length, between 1,000 to 4,000 base pairs in length, between 3 to 2,000 base pairs in length, between 50 to 2,000 base pairs in length, between 250 to 2,000 base pairs in length, or between 500 to 2,000 base pairs in length.

34. A method for making the parvovirus particle of paragraph 1, comprising: (a) providing a first plasmid comprising a first fragment comprising in a 5' to 3' direction: (i) a parvovirus terminal repeat comprising a left-end hairpin (LEH) or an inverted terminal repeat (ITR); (ii) a promoter having a left to right polarity; (iii) a nucleic acid encoding a first protein or first RNA having a left to right polarity; (iv) a polyadenylation signal having a left to right polarity, and (v) a first nuclease cut site in the first plasmid; (b) providing a second plasmid comprising a second fragment comprising in a 5' to 3' direction: (i) a first nuclease cut site; (ii) a first polyadenylation signal having a right to left polarity; (iii) a nucleic acid encoding the first protein or first RNA in (a)(iii), the first protein or first RNA having a right to left polarity; (iv) a nucleic acid encoding a second protein or second RNA, each of the second protein and second RNA having a left to right polarity; (v) a second polyadenylation signal; and (vi) a second nuclease cut site, wherein the cut site in (b)(i) and the cut site in (a)(v) are the same; (c) providing a third plasmid comprising a third fragment comprising in a 5' to 3' direction: (i) a parvovirus terminal repeat comprising a left-end hairpin (LEH) or an inverted terminal repeat (ITR); (ii) the promoter in (a)(ii) having a left to right polarity; (iii) a nucleic acid encoding the second protein or second RNA in (b)(iv), each of the second protein and second RNA having a left to right polarity; (iv) a polyadenylation signal having a left to right polarity, and (v) a third nuclease cut site unique to the third plasmid, wherein the cut site in (b)(iv) and the cut site in (c)(v) are the same; (d) providing a host cell comprising one or more helper genes sufficient for replicating a nucleic acid comprising parvovirus terminal repeats flanking a nucleic acid of interest; (e) digesting the first plasmid with a nuclease enzyme specific for the nuclease cut site in (a)(v) under conditions sufficient for linearizing the first plasmid, wherein the first plasmid is digested in vitro or is digested in the host cell; (f) digesting the second plasmid with a nuclease enzyme specific for the nuclease cut site in (b)(i) and digesting the second plasmid with a nuclease enzyme specific for the nuclease cut site in (b)(vi)

under conditions sufficient for digesting the second plasmid, wherein the second plasmid is digested in vitro or is digested in the host cell; (g) digesting the third plasmid with a nuclease enzyme specific for the nuclease cut site in (c)(v) under conditions sufficient for linearizing the third plasmid, wherein the third plasmid is digested in vitro or is digested in the host cell; (h) ligating together the linearized first plasmid fragment, the second fragment, and the linearized third plasmid fragment with a DNA ligase, wherein the ligation is carried out in vitro or in the host cell; (i) culturing the host cell comprising the first, second and third plasmids treated according to steps (e) to (h) under conditions suitable for producing parvovirus particles following completion of step (h); and (j) recovering the parvovirus particles produced in step (i).

35. The method of paragraph 34, wherein the first fragment comprises a parvovirus LEH and the third fragment comprises a parvovirus REH.

36. The method of paragraph 34, wherein each of the first and third fragments comprises an AAV ITR.

37. The method of any one of paragraphs 34 to 36, wherein the nucleic acid encoding the first protein or first RNA in (a)(iii), (b)(ii), or both, is between 3 to 4,000 base pairs in length, between 50 to 4,000 base pairs in length, between 1,000 to 4,000 base pairs in length, between 3 to 2,000 base pairs in length, between 50 to 2,000 base pairs in length, between 250 to 2,000 base pairs in length, or between 500 to 2,000 base pairs in length.

38. The method of any one of paragraphs 34 to 36, wherein the nucleic acid encoding the second protein or second RNA in (b)(iv), (c)(iii), or both, is between 3 to 4,000 base pairs in length, between 50 to 4,000 base pairs in length, between 1,000 to 4,000 base pairs in length, between 3 to 2,000 base pairs in length, between 50 to 2,000 base pairs in length, between 250 to 2,000 base pairs in length, or between 500 to 2,000 base pairs in length.

39. A method for making a self-complementary AAV, comprising: (a) providing a plasmid comprising a fragment comprising in a 5' to 3' direction: (i) a parvovirus terminal repeat comprising an AAV ITR; (ii) a promoter operatively linked to a nucleic acid encoding a protein or RNA; (iii) at least half of a mutant inverted terminal repeat (mITR) or at least half of a short hairpin DNA (shDNA); and (iv) a nuclease cut site; (b) providing a host cell comprising one or more helper genes sufficient for replicating a nucleic acid comprising parvovirus terminal repeats flanking a nucleic acid of interest; (c) digesting the plasmid with a nuclease enzyme specific for the nuclease cut site under conditions sufficient for linearizing the plasmid, wherein the plasmid is digested in vitro or is digested in the host cell; (d) ligating the plasmid to itself with a DNA ligase, wherein the plasmid is ligated in vitro or is ligated in the host cell so that a hairpin comprising mTR or shDNA sequences is formed; (e) culturing the host cell comprising the plasmid treated according to steps (c) and (d) under conditions suitable for producing parvovirus particles following completion of step (d); and (f) recovering the parvovirus particles produced in step (f).

40. A method for making a self-complementary AAV, comprising: (a) providing a first plasmid comprising a fragment comprising in a 5' to 3' direction: (i) a parvovirus terminal repeat comprising an AAV ITR; (ii) a promoter operatively linked to a nucleic acid encoding a protein or RNA; (iii) a partial mTR or partial shDNA; and (iv) a nuclease cut site; (b) providing a second plasmid comprising a fragment comprising in a 5' to 3' direction: (i) a parvovirus terminal repeat comprising an AAV ITR; (ii) a promoter operatively linked to a nucleic acid encoding a protein or RNA; (iii) a partial mTR or partial shDNA; and (iv) a nuclease cut site; (c) providing a host cell comprising one or more helper genes sufficient for replicating a nucleic acid comprising parvovirus terminal repeats flanking a nucleic acid of interest; (d) digesting the first plasmid with a nuclease enzyme specific for the nuclease cut site in (a)(iii) under conditions sufficient for linearizing the first plasmid, wherein the first plasmid is digested in vitro or is digested in the host cell; (e) digesting the second plasmid with a nuclease enzyme specific for the nuclease cut site in (b)(iv) under conditions sufficient for linearizing the second plasmid, wherein the second plasmid is digested in vitro or is digested in the host cell; (f) ligating the first and second plasmids digested in steps (d) and (e) with a DNA ligase, wherein the digested first and second plasmids are ligated in vitro or are ligated in the host cell so that a hairpin comprising mTR or shDNA sequences is formed; (g) culturing the host cell comprising the first and second plasmids treated according to steps (d) to (f) under conditions suitable for producing parvovirus particles following completion of step (f); and (h) recovering the parvovirus particles produced in step (g).

41. A method for making a self-complementary AAV, comprising: (a) providing a plasmid comprising a fragment comprising in a 5' to 3' direction: (i) a parvovirus terminal repeat comprising an AAV ITR; (ii) a promoter operatively linked to a nucleic acid encoding a protein or RNA; and (iii) a nuclease cut site in the plasmid; (b) providing a DNA fragment comprising at least half of a mITR or at least half of a shDNA; (c) providing a host cell comprising one or more helper genes sufficient for replicating a nucleic acid comprising parvovirus terminal repeats flanking a nucleic acid of interest; (d) digesting the plasmid with a nuclease enzyme specific for the nuclease cut site under conditions sufficient for linearizing the plasmid, wherein the plasmid is digested in vitro or is digested in the host cell; (e) ligating the plasmid to the DNA fragment with a DNA ligase, wherein the plasmid is ligated in vitro or is ligated in the host cell so that a hairpin comprising mTR or shDNA sequences is formed; (f) culturing the host cell comprising the plasmid treated according to steps (d) and (t) under conditions suitable for producing parvovirus particles following completion of step (e); and (g) recovering the parvovirus particles produced in step (f).

42. A vector genome comprising in the 5' to 3' direction: (1) a parvovirus terminal repeat at the 5' end, (2) a first regulatory region comprising (a) a promoter region, or (b) a poly A or poly T sequence, or both (a) and (b), (3) a first heterologous nucleotide sequence, (4) a covalently closed end (CCE) domain, (5) a second heterologous nucleotide sequence, (6) a first regulatory region comprising (a) a promoter region, or (b) a poly A or poly T sequence, or both (a) and (b), and (7) a parvovirus terminal repeat at the 3' end; wherein the first regulatory sequence is complementary to the second heterologous sequence and forms a double-stranded region (DS-domain) in the vector genome, wherein the CCE domain is (a) a single covalent bond connecting the first heterologous nucleotide sequence and the second nucleotide sequence, or (b) a single stranded DNA region, and wherein the vector genome is capable of producing a double-stranded (DS)-RNA molecule from the DS-domain of the vector genome.

43. The vector genome of paragraph 42, wherein the DS-domain is not contiguous with a self-annealed stem portion comprising more than 20 contiguous nucleotide base pairs from a mutant inverted terminal repeat (mTR) sequence or a short hairpin RNA (shRNA) coding sequence.

44. The vector genome of paragraph 42, wherein the CCE domain does not contain an mTR sequence, or a shRNA coding sequence, or both.

45. The vector genome of paragraph 42, wherein the CCE domain comprises 0-50 nucleotides.

46. The vector genome of paragraph 42, wherein the CCE domain comprises 51-4000 nucleotides.

47. A method for producing dsRNA molecules, comprising: (1) growing host production cells, (2) introducing the vector genome of paragraph 42 to the host production cells, (3) introducing helper genes to the host production cells, (4) incubating the host production cells for at least 12 hours, wherein the vector genome expresses dsRNA molecules.

EXAMPLES

Example 1, cceAAV-CB-FIX Production Method Comparison cceAAV-CB-FIX was constructed to express FIX under the control of a CB promoter. It has the configuration of cceAAV-ZL. cceAAV-CB-FIX was constructed using scAAV-CB-FIX as the starting material. First, the mutant ITR was removed from scAAV-CB-FIX and replaced with a fragment containing I-sceI, Not I site and CR1 (cas9 site using guide RNA gCR1) to obtain plasmid pre-cceAAV-CB-FIX. The cceAAV-CB-FIX was produced using the following methods. Their yield was then measured and their performances was compared with scAAV-CB-FIX.

Direction ligation, pre-cceAAV-CB-FIX was digested with Not I and EcoRV and the fragment containing ITR was used for ligation. The resulting ligated fragment was used to co-transfect 293 cells along with adenovirus plasmid and pRepCap (AAV helper plasmid). The vectors were harvested 96 hours posttransfection and follow the standard protocol for purification.

In vivo ligation with I-sceI, plasmid pre-cceAAV-CB-FIX was used to transfect 293-i-sceI cells along with adenovirus plasmid and pRepCap (AAV helper plasmid). The vectors were harvested 96 hours posttransfection and follow the standard protocol for purification. 293-i-sceI is a cell line expressing I-sceI nuclease stably in 293 cell line.

Cas9 assisted production, pre-cceAAV-CB-FIX was used to transfect 293 cells along with pRepCap (AAV helper plasmid. It was then infected with Adenovirus carrying cas9 nuclease and gRNA gCR1. The vectors were harvested 48 hours post adenovirus infection and follow the standard protocol for purification.

| | Vector yield using scAAV made by transfection as 100% | Quality (short genome packaged) | In vivo factor IX expression level 8 weeks after injection in |
|---|---|---|---|
| Direct ligation | ~200-900% | 0.1-5% | ~250-1000% |
| In vivo ligation | ~300%-1000% | 1-5% | ~300-1000% |
| Cas9 digestion and ligation | ~50%-500% | 2-5% | ~200-600% |
| scAAV by transfection | 100% | 100% | 100% |

Example 2, cceAAV for dsRNA Expression

The cceAAV-dsRNA expression is shown in FIG. 26. Noticeably the poly A site is at the antisense strand. The poly A or poly A function equivalent elements (transcription terminator) can be placed anywhere in the negative strand (for example, it may be before the promoter or after the promoter or in the middle of the antisense strand). When AAV is in self-complimentary configuration, no dsRNA is expressed. The promoter for dsRNA can be any promoter including Class I, Class II, and Class II promoters. After AAV DNA undergoes second strand DNA synthesis or annealing of the positive strand and negative strand, dsRNA is expressed. dsRNA can be used to induce cellular responses or modulate target gene expression. To make cceAAV-GFP-dsRNA, we removed the poly A sequence from pAAV-CB-EGFP and then cloned the poly A sequence at the beginning of CB promoter in the reverse orientation to obtain pAAV-antisense-poly A-CB-GFP. To make AAV vector for expressing dsRNA of GFP, the pAAV-antisense-poly A-CB-GFP was digested by Not I and EcoRV to obtain the fragment with ITR-antisense-poly A-CB-GFP and then used to transfect 293 cells along AAV helper and adenovirus helper plasmids, the vector cce-AAV-CB-GFP-dsRNA was harvested at 96 posttransfection. The resulting vectors were then tested for dsRNA expression. We observed dsRNA expressing by qPCR at 48 hours post-infection. When the dsRNA vector was coinfected with regular GFP vector, GFP expression was reduced 10%-99% depending on the ratio of these two vectors.

Example 3, cceAAV for Delivering Single Stranded DNA Template for Gene Editing

The basic configuration is as illustrated in FIG. 3. To make cce-AAV-ssGFP, we prepared two fragments for ligation. One fragment contains ITR, 300 bp sense strand, ssDNA cassette (1300 bp) for gene editing. The other fragment contains ITR, 300 bp sense strand, (no ssDNA cassette). Then these two fragments were ligated before transfection to make AAV vectors. cce-AAV-ssGFP was then confirmed by sequencing. cce-AAV-GFP were tested in Cas9-gRNA for gene editing. There were 5-100 fold improvement observed depending on the MOI of cce-AAV-ssGFP.

Example 4, cceAAV for Expressing dsRNA and Delivering ssDNA at the Same Time

The illustration for the prototype of cceAAV for expressing dsRNA and delivering ssDNA at the same time is illustrated in FIG. 27. The single stranded DNA is more stable because the franking regions are duplex. This scheme is achieved by ligating one fragment containing ITR, poly A in antisense orientation, CB promoter, GFP sense strand and 800 bp single stranded DNA region and another fragment containing ITR, poly A in antisense orientation, CB promoter, and GFP sense strand. The vectors are made by co-transfection with AAV helper and mini-adenovirus plasmid. The dsRNA expression is confirmed in cells infected with vectors produced.

Example 5, cceAAV Based on TelN cceAAV-CB-GFP-miRNA was constructed to express miRNA under the control of CB promoter. It has the configuration of cceAAV-ZL. cceAAV-CB-GFP-miRNA was constructed using scAAV-CB-GFP as the starting material. First, the mutant ITR was removed from scAAV-CB-GFP and replaced with a miRNA expressing fragment containing I-sceI, Not I site, TelRL and CR1 (cas9 site using guide RNA gCR1) to obtain plasmid pre-cceAAV-CB-GFP-miRNA. The cceAAV-CB-GFP-miRNA were produced using the following the methods as described example 1 when utilizing I-sceI, Not I site, and CR1. When utilizing TelRL site, the precursor plasmid is incubated with TelN (New England Biolabs) for an hour before transfection. The resulting eceAAV-CB-GFP-miRNA yield from the new methods are 5-10 fold better than typical scAAV expressing miRNA. The contaminant level is 5-10 folder lower than typical vector production methods.

Example 6, cceAAV Carrying DNAzyme

The construct cceAAV-DNAzyme is constructed using the configuration of cceAAV-LS (FIG. 3). The DNAzyme tested including 8-17 and 10-23 DNAzyme (Santoro S W, Joyce G F (April 1997). "A general purpose RNA-cleaving DNA enzyme". Proceedings of the National Academy of Sciences of the United States of America. 94 (9): 4262-6. doi:10.1073/pnas.94.9.4262. PMC 20710. PMID 9113977.). The 10-23 DNAzyme contains a 15-nucleotide catalytic core that is flanked by two substrate recognition domains. This DNAzyme cleaves complementary RNAs efficiently in a sequence specific manner between an unpaired purine and a paired pyrimidine. The 10-23 DNAzyme is cloned into one fragment for ligation. The configuration of one fragment is 1. ITR, CB-GFP, poly A, -flexible DNA linker (50 bp), 10-23 DNAzyme, the other fragment is ITR, CB-GFP, poly A, -flexible DNA linker (50 bp). The ligation of the create a cceAAV genome with 10-23 DNAzyme in the single stranded DNA region (unpaired). The function of 10-23 DNA zyme is characterized following standard protocol that has been published by Joyce's group.

Example 7, ccePV with Two Different ITRs (LEH and REH)

We made three version human bocavirus virus-1 (HBoV1) vectors. The first one is cceHBoV-LEH2-CB-GFP. It is constructed through self-ligation of LEH-CB-GFP fragment, it is self-complementary with two copies of LEH. The second one is cceHBoV-REH2-CB-GFP. It is constructed through self ligation of REH-CB-GFP fragment, it is self-complementary with two copies of REH. The third one is cceHBoV-REH2-CB-GFP. It is constructed through REH-CB-GFP fragment and LEH-CB-GFP, it is self-complementary in transgene cassette but with one REH and one LEH. The resulting plasmid was cotranfected with HBoV1 helper and adenovirus helper and other reagents facilitate replication. The resulting vector was confirmed by southern blot and qPCR and tested for infectivity on 293 cells.

Example 8, Expressing dsRNA with AAV after AAV 2nd Synthesis or Annealing of Plus and Minus Polarity The vector was constructed by ligation of two fragments, the first fragment contains AAV-ITR, CB promoter, GFP sequence, and the second fragment contains complementary GFP sequence, poly A sequence and AAV ITR. Ligation of this fragment leads to a molecular configuration of AAV-ITR, CB promoter, GFP sequence, complementary GFP sequence, poly A sequence and AAV ITR (this plasmid cannot be made as plasmid because of its instability in host cells). This generates GFP sequences as dsRNA upon infection. The control of dsRNA of GFP expressed without 2nd DNA synthesis are made by ligation the following the first fragment containing AAV-ITR, complementary poly A sequence, CB promoter, and GFP sequence (in order) and the second fragment containing complementary GFP sequence, complementary CB promoter sequence, poly A sequence, and AAV-ITR (in order, it is essentially the first fragment). The final molecular configuration is AAV-ITR, complementary poly A sequence, CB promoter, GFP sequence, complementary GFP sequence, complementary CB promoter sequence, poly A sequence and AAV-ITR. The control AAV vector has reduced capacity of dsRNA since extra-complimentary sequences for poly A and promoter. However, it has the advantage of simplified ligation since it uses self-ligation.

The above description is for the purpose of teaching a person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The invention claimed is:

1. A duplexed parvovirus particle comprising:
   a parvovirus capsid; and
   a vector genome comprising in the 5' to 3' direction:
   (a) a parvovirus terminal repeat at the 5' end;
   (b) a parvovirus terminal repeat at the 3' end
   (c) a double stranded (DS) DNA domain between the terminal repeats in (a) and (b), the DS-DNA domain comprising a self-complementary first heterologous nucleotide sequence annealed to second heterologous nucleotide sequence; and
   (d) a single stranded covalently closed end (SS-CCE) domain between the first heterologous nucleotide sequence and the second heterologous nucleotide sequence, the SS-CCE domain comprising a looped structure;
   wherein the DS-DNA domain is not contiguous with a self-annealed stem portion comprising more than 20 contiguous nucleotide base pairs from a mutant inverted terminal repeat (mTR) sequence or a short hairpin DNA (shDNA) sequence, and
   wherein the vector genome is capable of being replicated to form the duplexed parvovirus particle when introduced into a host cell expressing helper functions sufficient for producing the duplexed parvovirus particle,
   wherein the SS-CCE domain comprises a sequence encoding a protein or RNA and wherein the sequence encoding the protein or RNA further comprises a downstream polyadenylation signal operatively linked thereto.

2. The parvovirus particle of claim 1, wherein the SS-CCE domain does not comprise more than 20 contiguous nucleotides from a mutant inverted terminal repeat (mTR) or a short hairpin DNA (shDNA) sequence.

3. The parvovirus particle of claim 1, wherein the SS-CCE domain comprises between 3 and 4,000 nucleotides, between 50 and 4,000 nucleotides, between 1,000 and 4,000 nucleotides, between 3 and 2,000 nucleotides, between 50 and 2,000 nucleotides, between 250 and 2,000 nucleotides, or between 500 and 2,000 nucleotides.

4. The parvovirus particle of claim 1, wherein the first heterologous nucleotide sequence has more than 95%, more than 99%, or 100% inverse complementarity to the second heterologous nucleotide sequence.

5. The parvovirus particle of claim 1, wherein the DS-DNA domain comprises a promoter operatively linked to nucleic acid encoding a protein or RNA.

6. The parvovirus particle of claim 5, wherein the DS-DNA domain further comprises a polyadenylation signal operatively linked to the nucleic acid encoding the protein or RNA.

7. The parvovirus particle of claim 1, wherein the DS-DNA domain is interrupted by a looped or branched single stranded DNA.

8. The parvovirus particle of claim 7, wherein the looped or branched single stranded DNA comprises nucleotide encoding a protein or RNA.

9. The parvovirus particle of claim 1, wherein the parvovirus terminal repeat in (a) comprises a left-end hairpin (LEH) and the terminal repeat in (b) comprises a right-end hairpin (REH).

10. The parvovirus particle of claim 1, wherein the parvovirus terminal repeat comprises an adeno-associated virus (AAV) inverted terminal repeat (ITR).

11. A duplexed parvovirus particle comprising:
a parvovirus capsid; and
a vector genome comprising in the 5' to 3' direction:
  (a) a parvovirus terminal repeat at the 5' end;
  (b) a parvovirus terminal repeat at the 3' end
  (c) a double stranded (DS) DNA domain between the terminal repeats in (a) and (b), the DS-DNA domain comprising a self-complementary first heterologous nucleotide sequence annealed to second heterologous nucleotide sequence; and
  (d) a single stranded covalently closed end (SS-CCE) domain between the first heterologous nucleotide sequence and the second heterologous nucleotide sequence, the SS-CCE domain comprising a looped structure;
wherein the DS-DNA domain is not contiguous with a self-annealed stem portion comprising more than 20 contiguous nucleotide base pairs from a mutant inverted terminal repeat (mTR) sequence or a short hairpin DNA (shDNA) sequence,
wherein the vector genome is capable of being replicated to form the duplexed parvovirus particle when introduced into a host cell expressing helper functions sufficient for producing the duplexed parvovirus particle,
wherein the DS-DNA domain is interrupted by a looped or branched single stranded DNA,
wherein the looped or branched single stranded DNA comprises nucleotide encoding a protein or RNA, and
wherein the sequence encoding the protein or RNA further comprises a downstream polyadenylation signal operatively linked thereto.

* * * * *